(12) United States Patent
Schulze et al.

(10) Patent No.: US 9,388,177 B2
(45) Date of Patent: Jul. 12, 2016

(54) METHOD FOR PREPARING SUBSTITUTED TRIAZOLOPYRIDINES

(71) Applicant: BAYER PHARMA AKTIENGESELLSCHAFT, Berlin (DE)

(72) Inventors: Volker Schulze, OT Bergfelde (DE); Franz-Josef Mais, Düsseldorf (DE)

(73) Assignee: BAYER PHARMA AKTIENGESELLSCHAFT, Berlin (DE)

(*) Notice: Subject to any disclaimer, the term of this patent is extended or adjusted under 35 U.S.C. 154(b) by 0 days.

(21) Appl. No.: 14/414,164

(22) PCT Filed: Jul. 3, 2013

(86) PCT No.: PCT/EP2013/064017
§ 371 (c)(1),
(2) Date: Jan. 12, 2015

(87) PCT Pub. No.: WO2014/009219
PCT Pub. Date: Jan. 16, 2014

(65) Prior Publication Data
US 2015/0148542 A1    May 28, 2015

(30) Foreign Application Priority Data

| Jul. 10, 2012 | (EP) | 12175640 |
| Sep. 24, 2012 | (EP) | 12185590 |
| Jun. 5, 2013 | (EP) | 13170585 |

(51) Int. Cl.
*C07D 401/14* (2006.01)
*C07D 471/04* (2006.01)

(52) U.S. Cl.
CPC .................... *C07D 471/04* (2013.01)

(58) Field of Classification Search
CPC .................................................... C07D 401/14
USPC ............................................................ 546/119
See application file for complete search history.

(56) References Cited

U.S. PATENT DOCUMENTS

| 2012/0328610 | A1* | 12/2012 | Schulze | C07D 471/04 424/133.1 |
| 2013/0156756 | A1* | 6/2013 | Schulze | A61K 31/437 424/133.1 |
| 2014/0120087 | A1* | 5/2014 | Schulze | C07D 471/04 424/133.1 |
| 2015/0210683 | A1* | 7/2015 | Schulze | C07D 471/04 424/133.1 |

FOREIGN PATENT DOCUMENTS

WO    2011063907    *    6/2011

* cited by examiner

*Primary Examiner* — Niloofar Rahmani

(57) ABSTRACT

The present invention relates to methods of preparing substituted triazolopyridine compounds of general formula (I) as described and defined herein, as well as to intermediate compounds useful in the preparation of said compounds.

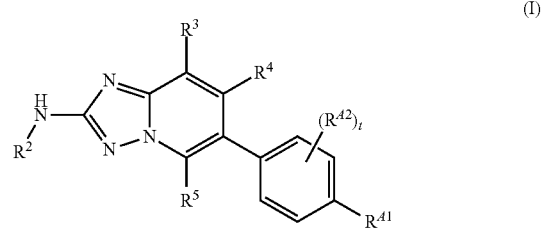

3 Claims, No Drawings

METHOD FOR PREPARING SUBSTITUTED TRIAZOLOPYRIDINES

The present invention relates to methods of preparing substituted triazolopyridine compounds of general formula (I) as described and defined herein, as well as to intermediate compounds useful in the preparation of said compounds.

BACKGROUND OF THE INVENTION

The present invention relates to methods of preparing special substituted triazolopyridine compounds that inhibit Mps-1 (Monopolar Spindle 1) kinase (also known as Tyrosine Threonine Kinase, UK). Mps-1 is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mol Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of a complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumorigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81].

Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Different compounds have been disclosed in prior art which show an inhibitory effect on Mps-1 kinase:

WO 2009/024824 A1 discloses 2-Anilinopurin-8-ones as inhibitors of Mps-1 for the treatment of proliferate disorders. WO 2010/124826 A1 discloses substituted imidazoquinoxaline compounds as inhibitors of Mps-1 kinase. WO 2011/026579 A1 discloses substituted aminoquinoxalines as Mps-1 inhibitors.

Substituted triazolopyridine compounds have been disclosed for the treatment or prophylaxis of different diseases:

WO 2008/025821 A1 (Cellzome (UK) Ltd) relates to triazole derivatives as kinase inhibitors, especially inhibitors of ITK or PI3K, for the treatment or prophylaxis of immunological, inflammatory or allergic disorders. Said triazole derivatives are exemplified as possessing an amide, urea or aliphatic amine substituent in position 2.

WO 2009/047514 A1 (Cancer Research Technology Limited) relates to [1,2,4]-triazolo-[1,5-a]-pyridine and [1,2,4]-triazolo-[1,5-c]-pyrimidine compounds which inhibit AXL receptor tyrosine kinase function, and to the treatment of diseases and conditions that are mediated by AXL receptor tyrosine kinase, that are ameliorated by the inhibition of AXL receptor tyrosine kinase function etc., including proliferative conditions such as cancer, etc. Said compounds are exemplified as possessing a substituent in the 5-position and a substituent in the 2-position.

WO 2009/010530 A1 discloses bicyclic heteroaryl compounds and their use as phosphatidylinositol (PI) 3-kinase. Among other compounds also substituted triazolopyridines are mentioned.

WO 2009/027283 A1 discloses triazolopyridine compounds and their use as ASK (apoptosis signal-regulating kinase) inhibitors for the treatment of autoimmune diseases and neurodegenerative diseases.

WO 2010/092041 A1 (Fovea Pharmaceuticals SA) relates to [1,2,4]-triazolo-[1,5-a]-pyridines, which are said to be useful as selective kinase inhibitors, to methods for producing such compounds and methods for treating or ameliorating kinase-mediated disorder. Said triazole derivatives are exemplified as possessing a 2-chloro-5-hydroxyphenyl substituent in the 6-position of the [1,2,4]-triazolo-[1,5-a]-pyridine.

WO 2011/064328 A1, WO 2011/063907 A1, WO 2011/063908 A1, and WO 2011/157688 A1 (Bayer Pharma AG) relate to [1,2,4]-triazolo-[1,5-a]-pyridines, methods for preparing said [1,2,4]-triazolo-[1,5-a]-pyridines, and their use for inhibition of Mps-1 kinase.

However, the state of the art described above neither discloses the triazolopyridine compounds of general formula (I) of the present invention, as described and defined herein, and as referred to in this text as "compounds of the present invention", nor the methods for preparing said compounds, as described and defined herein.

It was observed that the compounds of the present invention show a better performance in preclinical assessment than the compounds disclosed in prior art.

The objective of the present invention is to provide methods for preparing the compounds of the present invention.

SUMMARY OF THE INVENTION

The present invention is related to a method for preparing a compound of general formula (I):

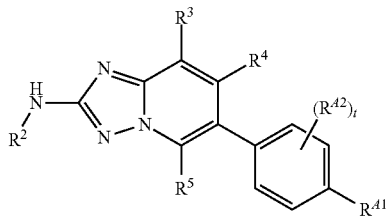

(I)

in which:
$R^{A1}$ represents a group selected from:
—N(H)C(=O)R$^6$, —C(=O)N(H)R$^6$;
each
$R^{A2}$ independently represents halo-, hydroxy-, nitro-, $C_1$-$C_6$-alkyl-, $C_1$-$C_6$-alkoxy-, hydroxy-$C_1$-$C_6$-alkyl-, —N(H)C(=O)R$^8$, —N(H)C(=O)NR$^8$R$^7$, —C(=O)N(H)R$^8$ or —N(H)S(=O)$_2$R$^8$;
$R^2$ represents a

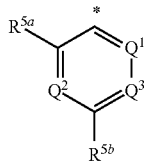

group;
wherein * indicates the point of attachment of said group with the rest of the molecule;
$R^3$ represents a hydrogen atom, a halogen atom, a hydroxy-, amino-, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or a halo-$C_3$-$C_6$-cycloalkyl-group;
$R^4$ represents a hydrogen atom, a halogen atom, a hydroxy-, amino-, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or a halo-$C_3$-$C_6$-cycloalkyl-group;
$R^5$ represents a hydrogen atom or a $C_1$-$C_3$-alkyl-group;
$R^{5a}$ represents a group selected from:
halo-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, R$^8$—($C_1$-$C_6$-alkoxy)-, R$^8$—O—, —NR$^8$R$^7$, R$^8$—S—, R$^8$—S(=O)—, R$^8$—S(=O)$_2$—, ($C_3$-$C_6$-cycloalkyl)-(CH$_2$)$_n$—O—;
$R^{5b}$ represents a group selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, R$^8$—($C_1$-$C_6$-alkyl)-, R$^8$—(CH$_2$)$_n$(CHOH)(CH$_2$)$_m$—, R$^8$—($C_1$-$C_6$-alkoxy)-, R$^8$—(CH$_2$)$_n$(CHOH)(CH$_2$)$_p$—O—, R$^8$—($C_1$-$C_6$-alkoxy-$C_1$-$C_6$-alkyl)-, R$^8$—($C_1$-$C_6$-alkoxy-$C_1$-$C_6$-alkyl)-O—, —O—(CH$_2$)$_n$—C(=O)NR$^8$R$^7$, R$^8$—O—, —C(=O)R$^8$, —C(=O)O—R$^8$, —OC(=O)—R$^8$, —N(H)C(=O)R$^8$, —N(R$^7$)C(=O)R$^8$, —N(R$^7$)C(=O)OR$^8$, —N(H)C(=O)NR$^8$R$^7$, —N(R$^7$)C(=O)NR$^8$R$^7$, —NR$^8$R$^7$, —NR$^7$R$^7$, —C(=O)N(H)R$^8$, —C(=O)NR$^8$R$^7$, R$^8$—S—, R$^8$—S(=O)—, R$^8$—S(=O)$_2$—, R$^7$—S(=O)$_2$—, —N(H)S(=O)R$^8$, —N(R$^7$)S(=O)R$^8$, —S(=O)N(H)R$^8$, —S(=O)NR$^8$R$^7$, —N(H)S(=O)$_2$R$^8$, —N(R$^7$)S(=O)$_2$R$^8$, —S(=O)$_2$N(H)R$^8$, —S(=O)$_2$NR$^8$R$^7$, —S(=O)(=NR$^8$)R$^7$, —S(=O)(=NR$^7$)R$^8$, —N=S(=O)(R$^8$)R$^7$;
$R^6$ represents a group selected from $C_3$-$C_6$-cycloalkyl-, 3- to 10-membered heterocyclyl-, aryl-, heteroaryl-, —(CH$_2$)$_q$—($C_3$-$C_6$-cycloalkyl), —(CH$_2$)$_q$-(3- to 10-membered heterocyclyl), —(CH$_2$)$_q$-aryl, or —(CH$_2$)$_q$-heteroaryl,
wherein said group is optionally substituted, one or more times, identically or differently, with a substituent selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —N(H)R$^8$; —N(R$^7$)R$^8$, N(H)(R$^8$)—$C_1$-$C_3$-alkyl-, N(R$^7$)(R$^8$)—$C_1$-$C_3$-alkyl-;
$R^7$ represents a hydrogen atom, a $C_1$-$C_6$-alkyl- or a $C_3$-$C_6$-cycloalkyl-group;
$R^8$ represents a hydrogen atom or a $C_1$-$C_6$-alkyl- or $C_3$-$C_6$-cycloalkyl-group, wherein said $C_1$-$C_6$-alkyl- or $C_3$-$C_6$-cycloalkyl-group is optionally substituted, one or more times, identically or differently, with a substituent selected from:
halo-, hydroxy-, $C_1$-$C_3$-alkyl-, $C_1$-$C_3$-alkoxy-, halo-$C_1$-$C_3$-alkoxy-;
or
$R^7$ and $R^8$ together with the molecular fragment they are attached to represent a 4- to 6-membered heterocyclic ring, which is optionally substituted, one or more times, identically of differently, with a halogen atom, a $C_1$-$C_3$-alkyl-, halo-$C_1$-$C_3$-alkyl- or $C_1$-$C_3$-alkoxy-group;
$Q^1$ represents a group selected from:
N, CH, C—($C_1$-$C_6$-alkyl), C—($C_1$-$C_6$-alkoxy), C-halo;
$Q^2$ represents a group selected from: N, CH, CR$^{5b}$;
$Q^3$ represents a group selected from: N, CH, CR$^{5b}$;
n, m, p,
represent, independently from each other, an integer of 0, 1, 2 or 3;
q represents an integer of 1, 2 or 3;
and
t represents an integer of 0, 1 or 2;
the method being characterized in that an intermediate compound of general formula (In1):

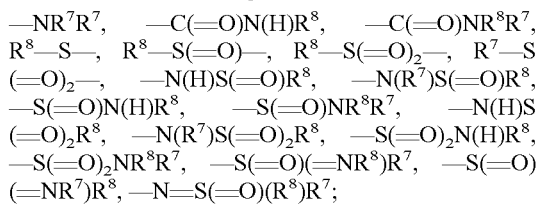

(In1)

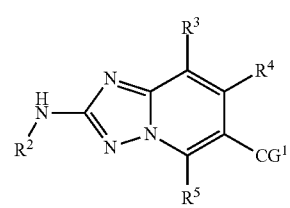

in which $R^2$, $R^3$, $R^4$, and $R^5$ are as defined for the compound of general formula (I), supra, and CG$^1$ is a group enabling palladium catalysed coupling reactions, including a leaving group, or a boronic acid or an ester or a derivative thereof;
is converted to a compound of general formula (I), supra.
The present invention further relates to intermediate compounds useful in the preparation of the compounds of formula (I), supra, in particular to intermediate compounds of formula (In1), supra, intermediate compounds of formula (In2), intermediate compounds of formula (In3), and intermediate compounds of formula (In4):

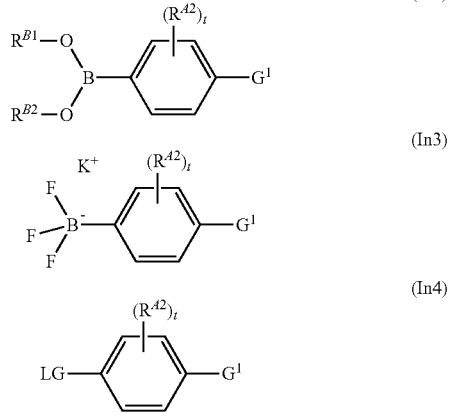

in which:
G¹ represents
  R^{A1}, wherein R^{A1} is as defined for general formula (I), supra, or
  —C(=O)OH, or a carboxylic acid ester, or
  —NH₂, or a protected amine;
R^{B1} and R^{B2}
  represent, independently from each other, a hydrogen atom or a $C_1$-$C_6$-alkyl- or $C_3$-$C_6$-cycloalkyl-group;
or
R^{B1} and R^{B2} together represent a $C_1$-$C_6$-alkylene group;
LG represents a leaving group, including chloro, bromo, iodo, trifluoromethylsulfonyloxy and the like;
and
R^{A2} and t are as defined for general formula (I), supra.

DETAILED DESCRIPTION OF THE INVENTION

The terms as mentioned in the present text have preferably the following meanings:
The term "halogen atom" or "halo-" is to be understood as meaning a fluorine, chlorine, bromine or iodine atom.
The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.
The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more of the hydrogen atoms is replaced, in identically or differently, by a halogen atom. Particularly, said halogen atom is F. Said halo-$C_1$-$C_6$-alkyl group is, for example, —CF₃, —CHF₂, —CH₂F, —CF₂CF₃, or —CH₂CF₃.

The term "$C_1$-$C_6$-alkoxy" is to be understood as preferably meaning a linear or branched, saturated, monovalent group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.
The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —OCF₃, —OCHF₂, —OCH₂F, —OCF₂CF₃, or —OCH₂CF₃.
The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.
The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —CH₂CH₂OCF₃, —CH₂CH₂OCHF₂, —CH₂CH₂OCH₂F, —CH₂CH₂OCF₂CF₃, or —CH₂CH₂OCH₂CF₃.
The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-inyl.

The term "$C_3$-$C_6$-cycloalkyl" is to be understood as preferably meaning a saturated, monovalent, mono-, or bicyclic hydrocarbon ring which contains 3, 4, 5 or 6 carbon atoms. Said $C_3$-$C_6$-cycloalkyl group is for example, a monocyclic hydrocarbon ring, e.g. a cyclopropyl, cyclobutyl, cyclopentyl, or cyclohexyl or a bicyclic hydrocarbon ring. Said cycloalkyl ring can optionally contain one or more double bonds e.g. cycloalkenyl, such as a cyclopropenyl, cyclobutenyl, cyclopentenyl or cyclohexenyl group, wherein the bond between said ring with the rest of the molecule may be to any carbon atom of said ring, be it saturated or unsaturated.

The term "heterocyclic ring", as used in the term "4-, 5- or 6-membered heterocyclic ring", or "4- to 6-membered heterocyclic ring" or "4- to 5-membered heterocyclic ring", for example, as used in the definition of compounds of general formula (I) as defined herein, is to be understood as meaning a saturated or partially unsaturated, monocyclic nitrogen atom-containing ring, said nitrogen atom being the point of attachment of said heterocyclic ring with the rest of the molecule. Said nitrogen atom-containing ring optionally further contains 1 or 2 heteroatom-containing groups selected from O and C(=O). Particularly, without being limited thereto, said nitrogen atom-containing ring can be a 4-membered ring, such as an azetidinyl ring, for example, or a 5-membered ring, such as a pyrrolidinyl ring or oxazolidinonyl ring, for example, or a 6-membered ring, such as a piperidinyl or morpholinyl ring, for example; it being reiterated that any of the above-mentioned nitrogen atom-containing rings can further contain 1 or 2 heteroatom-containing groups selected from O and C(=O).

As mentioned supra, said nitrogen atom-containing ring can be partially unsaturated, i.e. it can contain one or more double bonds, such as, without being limited thereto, a 2,5-dihydro-1H-pyrrolyl ring, for example.

The term "3- to 10-membered heterocycloalkyl" is to be understood as preferably meaning a saturated or partially unsaturated, monovalent, mono- or bicyclic hydrocarbon ring which contains 2, 3, 4, 5, 6, 7, 8, or 9 carbon atoms, and one or more heteroatom-containing groups selected from C(=O), O, S, S(=O), S(=O)$_2$, NH, NR", wherein R" represents a $C_1$-$C_6$-alkyl, $C_3$-$C_6$-cycloalkyl, —C(=O)—($C_1$-$C_6$-alkyl) or —C(=O)—($C_1$-$C_6$-cycloalkyl). Particularly, said ring can contain 2, 3, 4, or 5 carbon atoms, and one or more of the above-mentioned heteroatom-containing groups (a "3- to 6-membered heterocycloalkyl"), more particularly said ring can contain 4 or 5 carbon atoms, and one or more of the above-mentioned heteroatom-containing groups (a "5- to 6-membered heterocycloalkyl"). Said heterocycloalkyl ring is for example, a monocyclic heterocycloalkyl ring such as an oxyranyl, oxetanyl, aziridinyl, azetidinyl, tetrahydrofuranyl, pyrrolidinyl, imidazolidinyl, pyrazolidinyl, tetrahydropyranyl, piperidinyl, morpholinyl, dithianyl, thiomorpholinyl, piperazinyl, trithianyl, or chinuclidinyl group. Optionally, said heterocycloalkyl ring can contain one or more double bonds, e.g. 4H-pyranyl, 2H-pyranyl, 3H-diazirinyl, 2,5-dihydro-1 H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydro-1,3-oxazolyl, 4,4-dimethyl-4,5-dihydro-1,3-oxazolyl, or 4H-[1,4]thiazinyl group, or, it may be benzo fused.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group, or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group.

The term "heteroaryl" is understood as preferably meaning a monovalent, aromatic, mono- or bicyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and can be monocyclic, bicyclic, or tricyclic, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc. More particularly, heteroaryl is selected from pyridyl, benzofuranyl, benzisoxazolyl, indazolyl, quinazolinyl, thienyl, quinolinyl, benzothienyl, pyrazolyl, or furanyl.

The term "alkylene" is understood as preferably meaning an optionally substituted hydrocarbon chain (or "tether") having 1, 2, 3, 4, 5, 6, 7 or 8 carbon atoms, i.e. an optionally substituted —CH$_2$— ("methylene" or "single membered tether" or, for example —C(CH$_3$)$_2$—), —CH$_2$—CH$_2$— ("ethylene", "dimethylene", or "two-membered tether", for example —C(CH$_3$)$_2$—C(CH$_3$)$_2$—), —CH$_2$—CH$_2$—CH$_2$— ("propylene", "trimethylene", or "three-membered tether", for example —CH$_2$—C(H)(CH$_3$)—CH$_2$—, —CH$_2$—C (CH$_3$)$_2$—CH$_2$—), —CH$_2$—CH$_2$—CH$_2$—CH$_2$— ("butylene", "tetramethylene", or "four-membered tether"), —CH$_2$—CH$_2$—CH$_2$—CH$_2$—CH$_2$— ("pentylene", "pentamethylene" or "five-membered ether"), or —CH$_2$—CH$_2$—CH$_2$—CH$_2$—CH$_2$—CH$_2$— ("hexylene", "hexamethylene", or six-membered tether") group. Particularly, said alkylene tether has 1, 2, 3, 4, or 5 carbon atoms, more particularly 1 or 2 carbon atoms.

The term "C$_1$-C$_6$", as used throughout this text, e.g. in the context of the definition of "C$_1$-C$_6$-alkyl", "C$_1$-C$_6$-haloalkyl", "C$_1$-C$_6$-alkoxy", or "C$_1$-C$_6$-haloalkoxy" is to be understood as meaning an alkyl group having a finite number of carbon atoms of 1 to 6, i.e. 1, 2, 3, 4, 5, or 6 carbon atoms. It is to be understood further that said term "C$_1$-C$_6$" is to be interpreted as any sub-range comprised therein, e.g. C$_1$-C$_6$, C$_2$-C$_5$, C$_3$-C$_4$, C$_1$-C$_2$, C$_1$-C$_3$, C$_1$-C$_4$, C$_1$-C$_5$, C$_1$-C$_6$; particularly C$_1$-C$_2$, C$_1$-C$_3$, C$_1$-C$_4$, C$_1$-C$_5$, C$_1$-C$_6$; more particularly C$_1$-C$_4$; in the case of "C$_1$-C$_6$-haloalkyl" or "C$_1$-C$_6$-haloalkoxy" even more particularly C$_1$-C$_2$.

Similarly, as used herein, the term "C$_2$-C$_6$", as used throughout this text, e.g. in the context of the definitions of "C$_2$-C$_6$-alkenyl" and "C$_2$-C$_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "C$_2$-C$_6$" is to be interpreted as any sub-range comprised therein, e.g. C$_2$-C$_6$, C$_3$-C$_5$, C$_3$-C$_4$, C$_2$-C$_3$, C$_2$-C$_4$, C$_2$-C$_5$; particularly C$_2$-C$_3$.

Further, as used herein, the term "C$_3$-C$_6$", as used throughout this text, e.g. in the context of the definition of "C$_3$-C$_6$-cycloalkyl", is to be understood as meaning a cycloalkyl group having a finite number of carbon atoms of 3 to 6, i.e. 3, 4, 5 or 6 carbon atoms. It is to be understood further that said term "C$_3$-C$_6$" is to be interpreted as any sub-range comprised therein, e.g. C$_3$-C$_6$, C$_4$-C$_5$, C$_3$-C$_5$, C$_3$-C$_4$, C$_4$-C$_6$, C$_5$-C$_6$; particularly C$_3$-C$_6$.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

As used herein, the term "carboxylic acid ester" refers to a group of the formula —C(=O)OR$^E$ in which R$^E$ is e.g. a C$_1$-C$_6$-alkyl- or C$_3$-C$_6$-cycloalkyl-group.

As used herein, the term "protective group" is a group attached to a e.g. nitrogen atom or an oxygen atom in intermediates used for the preparation of compounds of the general formula (I). Such groups are introduced in order to obtain chemoselectivity in a subsequent chemical reaction.

As used herein, the term "protected amine" is an amino group in which a protective group is introduced by chemical modification of said amino group in order to obtain chemoselectivity in a subsequent chemical reaction. Protective groups for amino groups are described for example in T. W. Greene and P. G. M. Wuts in *Protective Groups in Organic Synthesis*, 3$^{rd}$ edition, Wiley 1999. Particularly, the term "protected amine" refers to a group of the formula —N(H)PG$^2$ in which PG$^2$ refers to a protective group for amino groups e.g. a Boc group as described for example in T. W. Greene and P. G. M. Wuts in *Protective Groups in Organic Synthesis*, 3rd edition, Wiley 1999 (Boc=tert-butyloxycarbonyl).

As used herein, the term "PG$^1$" refers to a protective group for hydroxy groups e.g. a TMS group or TBDPS group as described for example in T. W. Greene and P. G. M. Wuts in *Protective Groups in Organic Synthesis*, 3$^{rd}$ edition, Wiley 1999 (TMS=trimethylsilyl, TBDPS=tert-butyldiphenylsilyl).

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

The compounds of this invention contain one or more asymmetric centre, depending upon the location and nature of the various substituents desired. Asymmetric carbon atoms may be present in the (R) or (S) configuration. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, viz.:

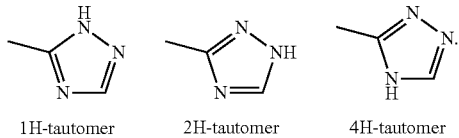

1H-tautomer  2H-tautomer  4H-tautomer

The present invention includes all possible tautomers of the compounds of the present invention as single tautomers, or as any mixture of said tautomers, in any ratio.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers a method for preparing a compound of general formula (I):

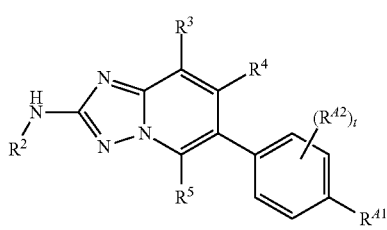

in which:
$R^{A1}$ represents a group selected from:
—N(H)C(=O)R$^6$, —C(=O)N(H)R$^6$;
each
$R^{A2}$ independently represents halo-, hydroxy-, nitro-, $C_1$-$C_6$-alkyl-, $C_1$-$C_6$-alkoxy-, hydroxy-$C_1$-$C_6$-alkyl-, —N(H)C(=O)R$^8$, —N(H)C(=O)NR$^8$R$^7$, —C(=O)N(H)R$^8$ or —N(H)S(=O)$_2$R$^8$;

$R^2$ represents a

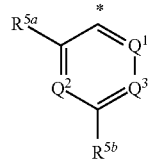

group;
wherein * indicates the point of attachment of said group with the rest of the molecule;
$R^3$ represents a hydrogen atom, a halogen atom, a hydroxy-, amino-, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or a halo-$C_3$-$C_6$-cycloalkyl-group;
$R^4$ represents a hydrogen atom, a halogen atom, a hydroxy-, amino-, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or a halo-$C_3$-$C_6$-cycloalkyl-group;
$R^5$ represents a hydrogen atom or a $C_1$-$C_3$-alkyl-group;
$R^{5a}$ represents a group selected from:
halo-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, R$^8$—($C_1$-$C_6$-alkoxy)-, R$^8$—O—, —NR$^8$R$^7$, R$^8$—S—, R$^8$—S(=O)—, R$^8$—S(=O)$_2$—, ($C_3$-$C_6$-cycloalkyl)-(CH$_2$)$_n$—O—;
$R^{5b}$ represents a group selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, R$^8$—($C_1$-$C_6$-alkyl)-, R$^8$—(CH$_2$)$_n$(CHOH)(CH$_2$)$_m$—, R$^8$—($C_1$-$C_6$-alkoxy)-, R$^8$—(CH$_2$)$_n$(CHOH)(CH$_2$)$_p$—O—, R$^8$—($C_1$-$C_6$-alkoxy-$C_1$-$C_6$-alkyl)-, R$^8$—($C_1$-$C_6$-alkoxy-$C_1$-$C_6$-alkyl)-O—, —O—(CH$_2$)$_n$—C(=O)NR$^8$R$^7$, R$^8$—O—, —C(=O)R$^8$, —C(=O)O—R$^8$, —OC(=O)—R$^8$, —N(H)C(=O)R$^8$, —N(R$^7$)C(=O)R$^8$, —N(R$^7$)C(=O)OR$^8$, —N(H)C(=O)NR$^8$R$^7$, —N(R$^7$)C(=O)NR$^8$R$^7$, —NR$^8$R$^7$, —NR$^7$R$^7$, —C(=O)N(H)R$^8$, —C(=O)NR$^8$R$^7$, R$^8$—S—, R$^8$—S(=O)—, R$^8$—S(=O)$_2$—, R$^7$—S(=O)$_2$—, —N(H)S(=O)R$^8$, —N(R$^7$)S(=O)R$^8$, —S(=O)N(H)R$^8$, —S(=O)NR$^8$R$^7$, —N(H)S(=O)$_2$R$^8$, —N(R$^7$)S(=O)$_2$R$^8$, —S(=O)$_2$N(H)R$^8$, —S(=O)$_2$NR$^8$R$^7$, —S(=O)(=NR$^8$)R$^7$, —S(=O)(=NR$^7$)R$^8$, —N=S(=O)(R$^8$)R$^7$;
$R^6$ represents a group selected from $C_3$-$C_6$-cycloalkyl-, 3- to 10-membered heterocyclyl-, aryl-, heteroaryl-, —(CH$_2$)$_q$—($C_3$-$C_6$-cycloalkyl), (CH$_2$)$_q$-(3- to 10-membered heterocyclyl), —(CH$_2$)$_q$-aryl, or —(CH$_2$)$_q$-heteroaryl,
wherein said group is optionally substituted, one or more times, identically or differently, with a substituent selected from:
halo-, hydroxy-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$- alkoxy-$C_1$-$C_6$-alkyl-, —N(H)$R^8$; —N($R^7$)$R^8$, N(H)($R^8$)—$C_1$-$C_3$-alkyl-, N($R^7$)($R^8$)—$C_1$-$C_3$-alkyl-;

$R^7$ represents a hydrogen atom, a $C_1$-$C_6$-alkyl- or a $C_3$-$C_6$-cycloalkyl-group;

$R^8$ represents a hydrogen atom or a $C_1$-$C_6$-alkyl- or $C_3$-$C_6$-cycloalkyl-group, wherein said $C_1$-$C_6$-alkyl- or $C_3$-$C_6$-cycloalkyl-group is optionally substituted, one or more times, identically or differently, with a substituent selected from: halo-, hydroxy-, $C_1$-$C_3$-alkyl-, $C_1$-$C_3$-alkoxy-, halo-$C_1$-$C_3$-alkoxy-;

or $R^7$ and $R^8$ together with the molecular fragment they are attached to represent a 4- to 6-membered heterocyclic ring, which is optionally substituted, one or more times, identically of differently, with a halogen atom, a $C_1$-$C_3$-alkyl-, halo-$C_1$-$C_3$-alkyl- or $C_1$-$C_3$-alkoxy-group;

$Q^1$ represents a group selected from: N, CH, C—($C_1$-$C_6$-alkyl), C—($C_1$-$C_6$-alkoxy), C-halo;

$Q^2$ represents a group selected from: N, CH, C$R^{5b}$);

$Q^3$ represents a group selected from: N, CH, C$R^{5b}$);

n, m, p, represent, independently from each other, an integer of 0, 1, 2 or 3;

q represents an integer of 1, 2 or 3; and t represents an integer of 0, 1 or 2;

the method being characterized in that an intermediate compound of general formula (In1):

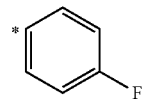

(In1)

in which $R^2$, $R^3$, $R^4$, and $R^5$ are as defined for the compound of general formula (I), supra, and $CG^1$ is a group enabling palladium catalysed coupling reactions, including a leaving group, or a boronic acid or an ester thereof or a derivative thereof;

is converted to a compound of general formula (I), supra.

In a preferred embodiment, the invention relates to a method for preparing a compound of general formula (I), supra, wherein $R^{41}$ represents —C(═O)N(H)$R^6$.

In another preferred embodiment, the invention relates to a method for preparing a compound of general formula (I), supra, wherein $R^{41}$ represents —N(H)C(═O)$R^6$.

In another preferred embodiment, the invention relates to a method for preparing a compound of general formula (I), supra, wherein $R^{41}$ represents

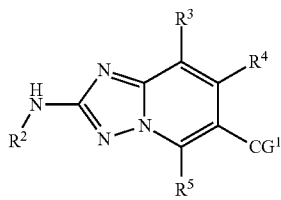

wherein * indicates the point of attachment of said group with the rest of the molecule;

wherein $R^9$ represents a group selected from: $C_1$-$C_3$-alkyl-, hydroxy-$C_1$-$C_3$-alkyl-, —N(H)$R^8$; —N($R^7$)$R^8$, N(H)($R^8$)—$C_1$-$C_3$-alkyl-, N($R^7$)($R^8$)—$C_1$-$C_3$-alkyl-;

wherein $R^{10}$ represents a

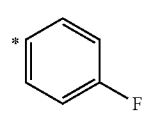

group; wherein * indicates the point of attachment of said group with the rest of the molecule; wherein said group is optionally substituted, one or more times, identically or differently, with a halogen atom or a methyl-group.

In another preferred embodiment, $R^9$ represents a group selected from: $C_1$-$C_3$-alkyl-, hydroxy-$C_1$-$C_3$-alkyl-, —N(H)$R^8$, N(H)($R^8$)—$C_1$-$C_3$-alkyl-.

In another preferred embodiment, $R^9$ represents a group selected from: $C_1$-$C_3$-alkyl-, hydroxy-$C_1$-$C_3$-alkyl-, —N($R^{11}$)$R^{11}$, —$C_1$-$C_2$-alkyl-N($R^{11}$)$R^{11}$; in which $R^{11}$ represents a hydrogen atom or a methyl-group.

In another preferred embodiment, $R^9$ represents a group selected from: methyl-, hydroxy-$C_1$-$C_2$-alkyl-, —N($R^{11}$)$R^{11}$, —$C_1$-$C_2$-alkyl-N($R^{11}$)$R^{11}$; in which $R^{11}$ represents a hydrogen atom or a methyl-group.

In another preferred embodiment, $R^9$ represents a group selected from: methyl-, HO—$CH_2$—, $H_2N$—$CH_2$—, —$NH_2$.

In another preferred embodiment, $R^9$ represents a group selected from: methyl-, HO—$CH_2$—, —$NH_2$.

In another preferred embodiment, $R^9$ represents a methyl-group.

In another preferred embodiment, $R^9$ represents a HO—$CH_2$— group.

In another preferred embodiment, $R^9$ represents a —$NH_2$ group.

In another preferred embodiment, $R^{10}$ represents a

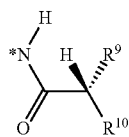

group; wherein * indicates the point of attachment of said group with the rest of the molecule.

In another preferred embodiment, the invention relates to a method for preparing a compound of general formula (I), supra, wherein $R^{41}$ represents a group selected from:

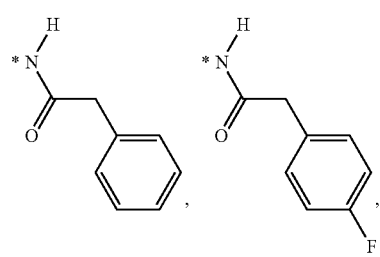

-continued

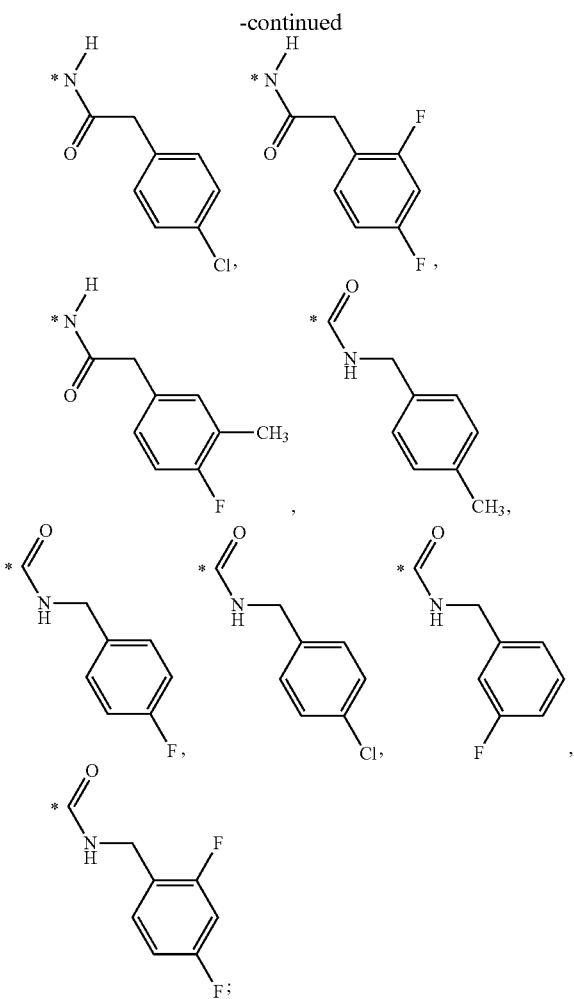

wherein * indicates the point of attachment of said groups with the rest of the molecule.

In another preferred embodiment, the invention relates to a method for preparing a compound of general formula (I), supra, wherein $R^{41}$ represents a group selected from:

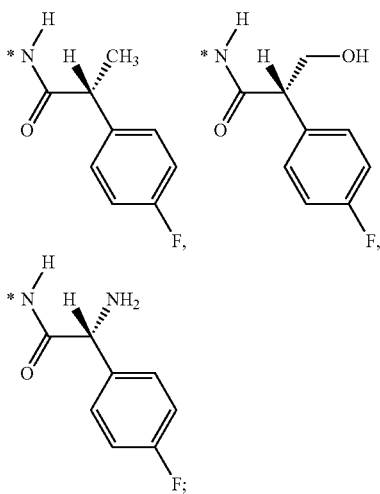

wherein * indicates the point of attachment of said groups with the rest of the molecule.

In another preferred embodiment, the invention relates to a method for preparing a compound of general formula (I), supra, wherein each $R^{42}$ independently represents halo-, $C_1$-$C_6$-alkyl-, $C_1$-$C_6$-alkoxy-, —N(H)C(=O)$R^8$ or —C(=O)N(H)$R^8$.

In another preferred embodiment, the invention relates to a method for preparing a compound of general formula (I), supra, wherein each $R^{42}$ independently represents halo-, $C_1$-$C_6$-alkyl- or $C_1$-$C_6$-alkoxy-.

In another preferred embodiment, the invention relates to a method for preparing a compound of general formula (I), supra, wherein each $R^{42}$ independently represents halo-, $C_1$-$C_3$-alkyl- or $C_1$-$C_3$-alkoxy-.

In another preferred embodiment, the invention relates to a method for preparing a compound of general formula (I), supra, wherein t represents 1 and $R^{42}$ represents halo-, $C_1$-$C_6$-alkyl- or $C_1$-$C_6$-alkoxy-.

In another preferred embodiment, the invention relates to a method for preparing a compound of general formula (I), supra, wherein t represents 1 and $R^{42}$ represents halo-, $C_1$-$C_3$-alkyl- or $C_1$-$C_3$-alkoxy-.

In another preferred embodiment, the invention relates to a method for preparing a compound of general formula (I), supra, wherein $Q^1$ represents a group selected from: CH, C—($C_1$-$C_6$-alkyl), C—($C_1$-$C_6$-alkoxy), C-halo. Preferably, $Q^1$ represents CH.

In another preferred embodiment, the invention relates to a method for preparing a compound of general formula (I), supra, wherein $Q^2$ represents a group selected from: N, CH, C—$R^{5c}$; wherein $R^{5c}$ is selected from the groups consisting of: halo-, cyano-, $C_1$-$C_6$-alkyl-, $C_1$-$C_6$-alkoxy-, —N(H)C(=O)$R^7$, —N($R^7$)C(=O)$R^7$, —C(=O)N(H)$R^8$, —C(=O)N$R^8R^7$, $R^8$—S(=O)—, $R^8$—S(=O)$_2$—, —S(=O)(=N$R^7$)$R^8$. Preferably, $Q^2$ represents CH.

In another preferred embodiment, the invention relates to a method for preparing a compound of general formula (I), supra, wherein $Q^3$ represents a group selected from: N, CH, C—$R^{5c}$, wherein $R^{5c}$ is selected from the groups consisting of: halo-, cyano-, $C_1$-$C_6$-alkyl-, $C_1$-$C_6$-alkoxy-, —N(H)C(=O)$R^7$, —N($R^7$)C(=O)$R^7$, —C(=O)N(H)$R^8$, —C(=O)N$R^8R^7$, $R^8$—S(=O)—, $R^8$—S(=O)$_2$—, —S(=O)(=N$R^7$)$R^8$. Preferably, $Q^3$ represents CH or N.

In another preferred embodiment, the invention relates to a method for preparing a compound of general formula (I), supra, wherein $Q^1$ and $Q^2$ represent CH, and $Q^3$ represents CH or N.

In another preferred embodiment, the invention relates to a method for preparing a compound of general formula (I), supra, wherein $Q^1$ and $Q^2$ and $Q^3$ represent CH.

In another preferred embodiment, the invention relates to a method for preparing a compound of general formula (I), supra, wherein $R^2$ is selected from the group consisting of:

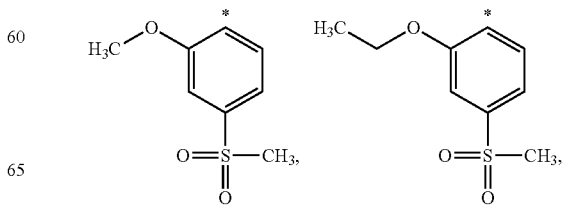

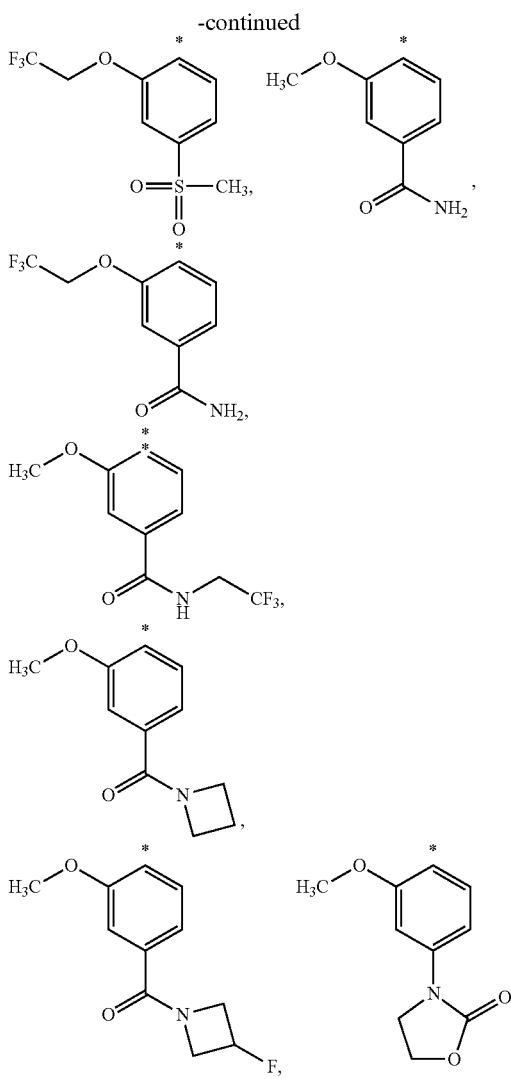

wherein * indicates the point of attachment of said groups with the rest of the molecule.

In another preferred embodiment, the invention relates to a method for preparing a compound of general formula (I), supra, wherein $R^3$ represents a hydrogen atom, halo-, hydroxy-, $C_1$-$C_4$-alkyl-, halo-$C_1$-$C_4$-alkyl- or $C_1$-$C_4$-alkoxy-group. Preferably, $R^3$ represents a hydrogen atom.

In another preferred embodiment, the invention relates to a method for preparing a compound of general formula (I), supra, wherein $R^4$ represents a hydrogen atom, halo-, a $C_1$-$C_6$-alkyl-, halo-$C_1$-$C_6$-alkyl- or $C_1$-$C_6$-alkoxy-group.

Preferably, $R^4$ represents a hydrogen atom.

In another preferred embodiment, the invention relates to a method for preparing a compound of general formula (I), supra, wherein $R^3$ and $R^4$ represent a hydrogen atom.

In another preferred embodiment, the invention relates to a method for preparing a compound of general formula (I), supra, wherein $R^5$ represents a hydrogen atom or a methyl-group.

In another preferred embodiment, the invention relates to a method for preparing a compound of general formula (I), supra, wherein $R^5$ represents a hydrogen atom.

In another preferred embodiment, the invention relates to a method for preparing a compound of general formula (I), supra, wherein $R^3$ and $R^4$ and $R^5$ represent a hydrogen atom.

In another preferred embodiment, the invention relates to a method for preparing a compound of general formula (I), supra, wherein $R^{5a}$ represents a group selected from: halo-, $C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkoxy)-, $R^8$—O—, $R^8$—S—, $R^8$—S(=O)$_2$—, ($C_3$-$C_6$-cycloalkyl)-(CH$_2$)$_n$—O—.

Preferably, $R^{5a}$ is selected from: halo-, $C_1$-$C_6$-alkyl-, $C_1$-$C_6$-alkoxy-, halo-$C_1$-$C_6$-alkoxy-, $C_1$-$C_6$-alkoxy-$C_1$-$C_6$-alkyl-, ($C_3$-$C_6$-cycloalkyl)-(CH$_2$)$_n$—O—.

More preferably, $R^{5a}$ is selected from: F—, methyl-, methoxy-, ethoxy-, n-propoxy-, iso-propoxy-, cyclopropyl-O—, cyclopropyl-CH$_2$—O—, CH$_3$—O—CH$_2$CH$_2$—O—, CHF$_2$—O—, CF$_3$—O—, CF$_3$CH$_2$—O—.

In another preferred embodiment, the invention relates to a method for preparing a compound of general formula (I), supra, wherein $R^{5a}$ represents a $C_1$-$C_6$-alkoxy-group.

In another preferred embodiment, the invention relates to a method for preparing a compound of general formula (I), supra, wherein $R^{5a}$ represents a $C_1$-$C_3$-alkoxy-group.

In another preferred embodiment, the invention relates to a method for preparing a compound of general formula (I), supra, wherein $R^{5a}$ represents a halo-$C_1$-$C_6$-alkoxy-group.

In another preferred embodiment, the invention relates to a method for preparing a compound of general formula (I), supra, wherein $R^{5a}$ represents a halo-$C_1$-$C_3$-alkoxy-group.

In another preferred embodiment, the invention relates to a method for preparing a compound of general formula (I), supra, wherein $R^{5a}$ represents a group selected from: $C_1$-$C_3$-alkoxy-, halo-$C_1$-$C_3$-alkoxy-, $C_1$-$C_3$-alkyl-.

In another preferred embodiment, the invention relates to a method for preparing a compound of general formula (I), supra, wherein $R^{5a}$ represents a group selected from: $C_1$-$C_2$-alkoxy-, halo-$C_1$-$C_2$-alkoxy-, $C_1$-$C_2$-alkyl-.

In another preferred embodiment, the invention relates to a method for preparing a compound of general formula (I), supra, wherein $R^{5a}$ represents a group selected from: $C_1$-$C_3$-alkoxy-, halo-$C_1$-$C_3$-alkoxy-.

In another preferred embodiment, the invention relates to a method for preparing a compound of general formula (I), supra, wherein $R^{5a}$ represents a group selected from: $C_1$-$C_2$-alkoxy-, halo-$C_1$-$C_2$-alkoxy-.

In another preferred embodiment, the invention relates to a method for preparing a compound of general formula (I), supra, wherein $R^{5a}$ represents a methoxy- or ethoxy-group which is optionally substituted, one or more times, identically or differently, with a halogen atom. The preferred halogen atom is F.

In another preferred embodiment, the invention relates to a method for preparing a compound of general formula (I), supra, wherein $R^{5a}$ represents a group selected from: methoxy-, ethoxy-, F$_3$C—CH$_2$—O—.

In another preferred embodiment, the invention relates to a method for preparing a compound of general formula (I), supra, wherein $R^{5a}$ represents a group selected from: methoxy-, F$_3$C—CH$_2$—O—.

In another preferred embodiment, the invention relates to a method for preparing a compound of general formula (I), supra, wherein $R^{5b}$ represents a group selected from: halo-, cyano-, nitro-, $C_1$-$C_6$-alkyl-, halo-$C_1$-$C_6$-alkyl-, hydroxy-$C_1$-$C_6$-alkyl-, $C_1$-$C_6$-alkoxy-, halo-$C_1$-$C_6$-alkoxy-, $R^8$—O—, —C(=O)R$^8$, —C(=O)O—R$^8$, —N(H)C(=O)R$^8$, —N(R$^7$)C(=O)R$^8$, —N(R$^7$)C(=O)OR$^8$, —N(H)S(=O)$_2$R$^8$, —NR$^8$R$^7$, —NR$^7$R$^7$, —C(=O)N(H)R$^8$, —C(=O)NR$^8$R$^7$, R$^8$—S(=O)—, R$^8$—S(=O)$_2$—, R$^7$—S(=O)$_2$—, —S(=O)(=NR$^7$)R$^8$.

Preferably, $R^{5b}$ is selected from: halo-, cyano-, —$NR^7R^7$, $C_1$-$C_6$-alkoxy-, —$N(H)C(=O)R^8$, —$N(R^7)C(=O)R^8$, —$N(R^7)C(=O)OR^8$, —$C(=O)N(H)R^8$, —$C(=O)NR^8R^7$, $R^8$—$S(=O)$—, $R^8$—$S(=O)_2$—, $R^7$—$S(=O)_2$—, —$S(=O)(=NR^7)R^8$, hydroxy-$C_1$-$C_6$-alkyl-, —$N(H)S(=O)_2R^8$.

More preferably, $R^{5b}$ is selected from: fluoro-, cyano-, methoxy-, —$CH_2$—OH, —$C(OH)(CH_3)_2$, —$N(CH_3)_2$, —$C(=O)NH_2$, —$C(=O)N(CH_3)_2$, —$C(=O)N(C_2H_5)_2$, —$C(=O)N(CH_3)(C_2H_5)$, —$C(=O)NH(C_2H_5)$, —$C(=O)NH(CH_3)$, —$C(=O)NH(C(CH_3)_3)$, —$C(=O)NH(CH_2CH_2OH)$, —$C(=O)NH(CH_2CH_2F)$, —$C(=O)NH(CH_2CH_2OCH_3)$, —$C(=O)NH(CH_2CH_2OCH_2CH_3)$, —$C(=O)NH(C(CH_3)_2CH_2OH)$, —$C(=O)NH(CH_2C(CH_3)_2OH)$, —$C(=O)NH(CH_2CF_3)$, —$S(=O)CH_3$, $(CH_3)S(=O)_2$—, $(C_2H_5)S(=O)_2$—, —$N(H)C(=O)CH_3$,

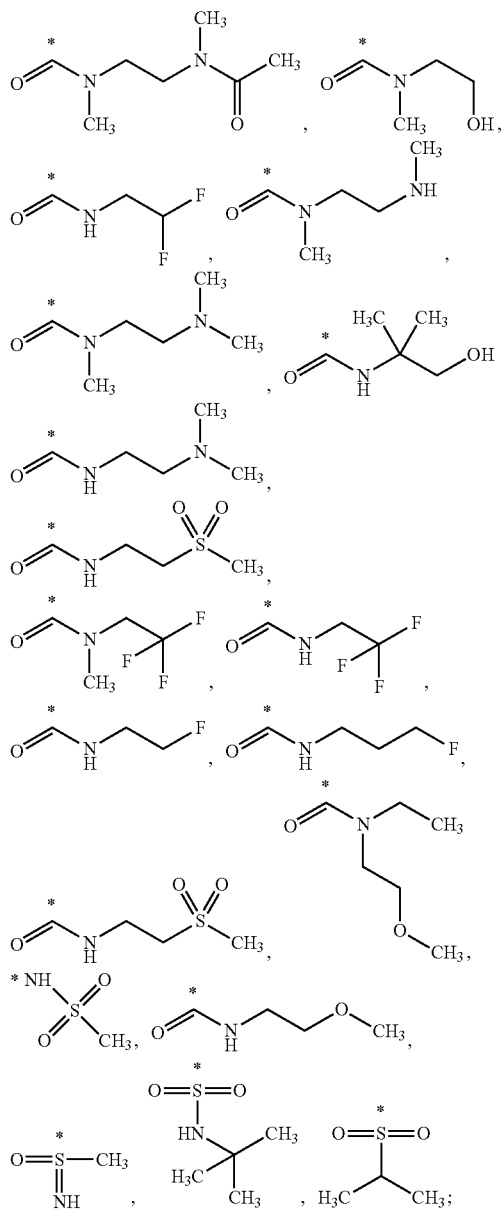

wherein * indicates the point of attachment of said group with the rest of the molecule.

In another preferred embodiment, the invention relates to a method for preparing a compound of general formula (I), supra, wherein $R^{5b}$ represents a group selected from: —$C(=O)N(H)R^8$, —$C(=O)NR^8R^7$, $R^8$—$S(=O)$—, $R^8$—$S(=O)_2$—, —$S(=O)(=NR^7)R^8$.

In another preferred embodiment, the invention relates to a method for preparing a compound of general formula (I), supra, wherein $R^{5b}$ represents a —$C(=O)N(H)R^8$ group.

In another preferred embodiment, the invention relates to a method for preparing a compound of general formula (I), supra, wherein $R^{5b}$ represents a —$C(=O)NR^8R^7$ group.

In another preferred embodiment, the invention relates to a method for preparing a compound of general formula (I), supra, wherein $R^{5b}$ represents a $R^8$—$S(=O)$— group.

In another preferred embodiment, the invention relates to a method for preparing a compound of general formula (I), supra, wherein $R^{5b}$ represents a $R^8$—$S(=O)_2$— group.

In another preferred embodiment, the invention relates to a method for preparing a compound of general formula (I), supra, wherein $R^{5b}$ represents a —$S(=O)(=NR^7)R^8$ group.

In another preferred embodiment, the invention relates to a method for preparing a compound of general formula (I), supra, wherein $R^{5b}$ represents a —$C(=O)N(H)R^7$ group.

In another preferred embodiment, the invention relates to a method for preparing a compound of general formula (I), supra, wherein $R^{5b}$ represents a $R^7$—$S(=O)_2$ group.

In another preferred embodiment, the invention relates to a method for preparing a compound of general formula (I), supra, wherein $R^{5b}$ represents $R^7$—$S(=O)_2$ group; in which $R^7$ represents a $C_1$-$C_3$-alkyl-group.

In another preferred embodiment, the invention relates to a method for preparing a compound of general formula (I), supra, wherein $R^{5b}$ represents a $R^7$—$S(=O)_2$ group; in which $R^7$ represents a methyl-group.

In another preferred embodiment, the invention relates to a method for preparing a compound of general formula (I), supra, wherein $R^{5b}$ represents —$C(=O)N(H)R^8$; in which $R^8$ represents a hydrogen atom or a $C_1$-$C_3$-alkyl- or $C_3$-$C_6$-cycloalkyl-group, wherein said $C_1$-$C_3$-alkyl- or $C_3$-$C_6$-cycloalkyl-group is optionally substituted, one or more times, with a halogen atom. The preferred halogen atom is F.

In another preferred embodiment, the invention relates to a method for preparing a compound of general formula (I), supra, wherein $R^{5b}$ represents —$C(=O)N(H)R^8$; in which $R^8$ represents a hydrogen atom or a $C_1$-$C_3$-alkyl-group, wherein said $C_1$-$C_3$-alkyl-group is optionally substituted, one or more times, with a halogen atom. The preferred halogen atom is F.

In another preferred embodiment, the invention relates to a method for preparing a compound of general formula (I), supra, wherein $R^{5b}$ represents —$C(=O)N(H)R^8$; in which $R^8$ represents a group selected from: —$CH_3$, —$CF_3$, —$C_2H_5$, —$CH_2CF_3$.

In another preferred embodiment, the invention relates to a method for preparing a compound of general formula (I), supra, wherein $R^{5b}$ represents —$C(=O)NR^8R^7$; in which $R^7$ and $R^8$ together with the N atom they are attached to represent a 4- to 6-membered heterocyclic ring, which is optionally substituted, one or more times, identically or differently, with a halogen atom, a $C_1$-$C_3$-alkyl- or a halo-$C_1$-$C_3$-alkyl-group.

In another preferred embodiment, the invention relates to a method for preparing a compound of general formula (I), supra, wherein $R^{5b}$ represents —$C(=O)NR^8R^7$; in which $R^7$ and $R^8$ together with the N atom they are attached to represent a 4-membered heterocyclic ring, which is optionally substituted, one or more times, identically or differently, with a halogen atom, a $C_1$-$C_3$-alkyl- or a halo-$C_1$-$C_3$-alkyl-group.

In another preferred embodiment, the invention relates to a method for preparing a compound of general formula (I), supra, wherein $R^{5b}$ represents —$C(=O)NR^8R^7$; in which $R^7$ and $R^8$ together with the N atom they are attached to represent a 4- to 6-membered heterocyclic ring, which is optionally substituted, one or more times, identically or differently, with a halogen atom.

In another preferred embodiment, the invention relates to a method for preparing a compound of general formula (I), supra, wherein $R^{5b}$ represents —C(═O)NR$^8$R$^7$; in which $R^7$ and $R^8$ together with the N atom they are attached to represent a 4-membered heterocyclic ring, which is optionally substituted, one or more times, with a fluorine atom.

In another preferred embodiment, the invention relates to a method for preparing a compound of general formula (I), supra, wherein $R^{5b}$ represents —N(R$^7$)C(═O)OR$^8$; in which $R^7$ and $R^8$ together with the molecular fragment they are attached to represent a 4- to 6-membered heterocyclic ring, which is optionally substituted, one or more times, identically or differently, with a halogen atom, a $C_1$-$C_3$-alkyl- or a halo-$C_1$-$C_3$-alkyl-group.

In another preferred embodiment, the invention relates to a method for preparing a compound of general formula (I), supra, wherein $R^{5b}$ represents —N(R$^7$)C(═O)OR$^8$; in which $R^7$ and $R^8$ together with the molecular fragment they are attached to represent a 5-membered heterocyclic ring, which is optionally substituted, one or more times, identically or differently, with a halogen atom, a $C_1$-$C_3$-alkyl- or a halo-$C_1$-$C_3$-alkyl-group.

In another preferred embodiment, the invention relates to a method for preparing a compound of general formula (I), supra, wherein $R^{5b}$ represents —N(R$^7$)C(═O)OR$^8$; in which $R^7$ and $R^8$ together with the molecular fragment they are attached to represent a 5-membered heterocyclic ring.

In another preferred embodiment, the invention relates to a method for preparing a compound of general formula (I), supra, wherein $R^{5b}$ is selected from: $H_3C$—S(O)$_2$—, $H_2N$—C(O)—,

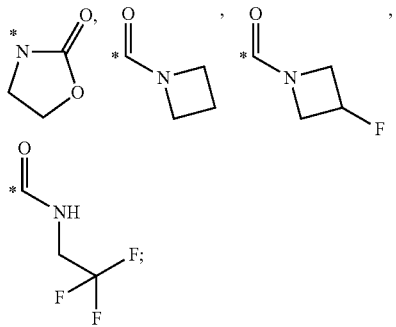

wherein * indicates the point of attachment of said groups with the rest of the molecule.

In another preferred embodiment, the invention relates to a method for preparing a compound of general formula (I), supra, wherein $R^6$ represents a group selected from: $C_3$-$C_6$-cycloalkyl-, 3- to 10-membered heterocyclyl-,
aryl-, heteroaryl-, —(CH$_2$)$_q$—($C_3$-$C_6$-cycloalkyl),
—(CH$_2$)$_q$-(3- to 10-membered heterocyclyl), —(CH$_2$)$_q$-aryl, or —(CH$_2$)$_q$-heteroaryl;
wherein said group is optionally substituted, one or more times, identically or differently, with a substituent selected from:
halo-, $C_1$-$C_6$-alkyl-, halo-$C_1$-$C_6$-alkyl-, halo-$C_1$-$C_6$-alkoxy-.

In another preferred embodiment, the invention relates to a method for preparing a compound of general formula (I), supra, wherein $R^6$ represents a group selected from: —CH$_2$—($C_3$-$C_6$-cycloalkyl), —CH$_2$-aryl; wherein said group is optionally substituted, one or more times, identically or differently, with a substituent selected from: halo-, $C_1$-$C_6$-alkyl-, halo-$C_1$-$C_6$-alkyl-, halo-$C_1$-$C_6$-alkoxy-.

The $C_3$-$C_6$-cycloalkyl-group preferably is a cyclopropyl-group; the aryl-group is preferably a phenyl-group.

In another preferred embodiment, the invention relates to a method for preparing a compound of general formula (I), supra, wherein $R^6$ represents a group selected from: —(CH$_2$)-phenyl, —(CH$_2$)-cyclopropyl;
wherein said group is optionally substituted, one or more times, identically or differently, with a substituent selected from: halo-, $C_1$-$C_6$-alkyl-.

In another preferred embodiment, the invention relates to a method for preparing a compound of general formula (I), supra, wherein $R^7$ represents a hydrogen atom or a $C_1$-$C_6$-alkyl-group.

In another preferred embodiment, the invention relates to a method for preparing a compound of general formula (I), supra, wherein $R^7$ represents a $C_1$-$C_3$-alkyl-group.

In another preferred embodiment, the invention relates to a method for preparing a compound of general formula (I), supra, wherein $R^7$ represents a methyl-group.

In another preferred embodiment, the invention relates to a method for preparing a compound of general formula (I), supra, wherein $R^7$ represents a hydrogen atom, or a $C_3$-$C_6$-cycloalkyl-group.

In another preferred embodiment, the invention relates to a method for preparing a compound of general formula (I), supra, wherein $R^8$ represents a hydrogen atom or a $C_1$-$C_6$-alkyl-group, wherein said $C_1$-$C_6$-alkyl-group is optionally substituted, one or more times, identically or differently, with a substituent selected from:
halo-, hydroxy-, —NHR$^7$, —NR$^7$R$^7$, —N($C_1$-$C_3$-alkyl)-C(═O) R$^7$, —N($C_1$-$C_3$-alkyl)-C(═O)OR$^7$, $C_1$-$C_3$-alkyl-, R$^7$—S(═O)$_2$—, $C_1$-$C_3$-alkoxy-, halo-$C_1$-$C_3$-alkoxy-.

In another preferred embodiment, the invention relates to a method for preparing a compound of general formula (I), supra, wherein $R^8$ represents a hydrogen atom or $C_3$-$C_6$-cycloalkyl-group, wherein said $C_3$-$C_6$-cycloalkyl-group is optionally substituted, one or more times, identically or differently, with a substituent selected from: halo-, hydroxy-, —NHR$^7$, —NR$^7$R$^7$, —N($C_1$-$C_3$-alkyl)-C(═O)R$^7$, —N($C_1$-$C_3$-alkyl)-C(═O)OR$^7$, $C_1$-$C_3$-alkyl-, R$^7$—S(═O)$_2$—, $C_1$-$C_3$-alkoxy-, halo-$C_1$-$C_3$-alkoxy-.

In another preferred embodiment, the invention relates to a method for preparing a compound of general formula (I), supra, wherein $R^8$ represents a hydrogen atom or a $C_1$-$C_6$-alkyl-group, wherein said $C_1$-$C_6$-alkyl-group is optionally substituted, one or more times, identically or differently, with a substituent selected from:
halo-, $C_1$-$C_3$-alkyl-, R$^7$—S(═O)$_2$—, $C_1$-$C_3$-alkoxy-, halo-$C_1$-$C_3$-alkoxy-.

In another preferred embodiment, the invention relates to a method for preparing a compound of general formula (I), supra, wherein $R^8$ represents a hydrogen atom or $C_3$-$C_6$-cycloalkyl-group, wherein said $C_3$-$C_6$-cycloalkyl-group is optionally substituted, one or more times, identically or differently, with a substituent selected from: halo-, $C_1$-$C_3$-alkyl-, R$^7$—S(═O)$_2$—, $C_1$-$C_3$-alkoxy-, halo-$C_1$-$C_3$-alkoxy-.

In another preferred embodiment, the invention relates to a method for preparing a compound of general formula (I), supra, wherein $R^8$ represents a hydrogen atom or a $C_1$-$C_6$-alkyl-group, wherein said $C_1$-$C_6$-alkyl-group is optionally substituted with a halogen atom.

In another preferred embodiment, the invention relates to a method for preparing a compound of general formula (I), supra, wherein $R^8$ represents a hydrogen atom or a $C_1$-$C_3$-alkyl-group, wherein said $C_1$-$C_3$-alkyl-group is optionally substituted, one or more times, with a halogen atom.

In another preferred embodiment, the invention relates to a method for preparing a compound of general formula (I), supra, wherein $R^7$ and $R^8$ together with the molecular fragment they are attached to represent a 4- to 6-membered heterocyclic ring, which is optionally substituted, one or more times, identically of differently, with a halogen atom, a $C_1$-$C_3$-alkyl-, halo-$C_1$-$C_3$-alkyl- or $C_1$-$C_3$-alkoxy-group.

In another preferred embodiment, the invention relates to a method for preparing a compound of general formula (I), supra, wherein n represents an integer of 0, 1 or 2. Preferably, n represent 0 or 1.

In another preferred embodiment, the invention relates to a method for preparing a compound of general formula (I), supra, wherein q represents an integer of 0, 1 or 2. Preferably, q represents 1 or 2. More preferably, q=1.

In another preferred embodiment, the invention relates to a method for preparing a compound of general formula (I), supra, wherein t represents an integer of 0 or 1. Preferably, t=0.

As one of ordinary skill in the art knows, the molecular weight of a compound very often has an influence on the bioavailability; see e.g. Lipinski's *Rule of five* (Lipinski, C. A.; Lombardo, F.; Dominy, B. W.; Feeney, P. J.; Adv. Drug Deliver. Rev. 1997, 23, 3). As experimentally proven there is no clear cutoff at a molecular weight of 500 separating compounds with poor bioavailability from those with acceptable values—however, it is proven that higher bioavailability is indeed associated with lower molecular weight (see e.g. Veber et al., J. Med. Chem. 2002, 45, 2615-2623). In a preferred embodiment, therefore the invention relates to compounds of formula (I), supra, wherein the molecular weight is less than 655. In another preferred embodiment, the molecular weight of the compound of formula (I), supra, is less than 630, more preferably less than 600, most preferably less than 590.

The method of the present invention is characterized in that an intermediate compound of general formula (In1):

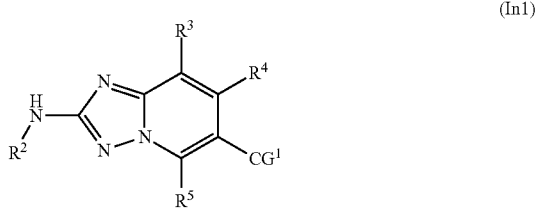

(In1)

in which $R^2$, $R^3$, $R^4$, and $R^5$ are as defined supra, and $CG^1$ is a group enabling palladium catalysed coupling reactions, including chloro, bromo, iodo, trifluoromethylsulfonyloxy, or a boronic acid or an ester thereof, is converted to a compound of general formula (I), supra.

In a preferred embodiment, the invention relates to a method for preparing a compound of general formula (I), wherein the method comprises the step of allowing a compound of general formula (In1):

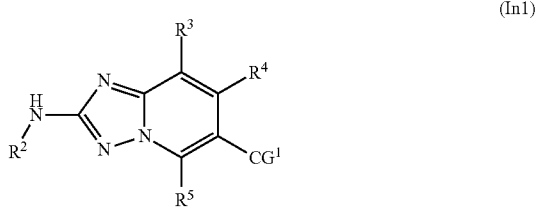

(In1)

to react with a compound of general formula (In5)

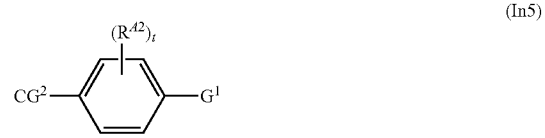

(In5)

thus providing a compound of general formula (Ia):

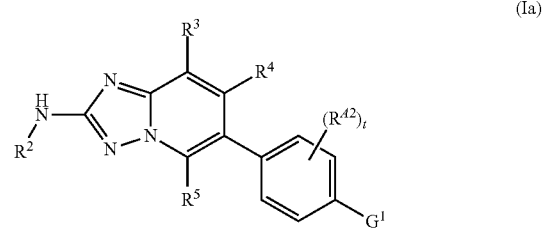

(Ia)

wherein:
$G^1$ represents
  $R^{41}$, wherein $R^{41}$ is as defined in claim 1, or
  —C(=O)OH, or a carboxylic acid ester, or
  —NH$_2$, or a protected amine;
$CG^1$ and $CG^2$
  represent groups enabling palladium catalysed coupling reactions, including chloro, bromo, iodo, trifluoromethylsulfonyloxy, or a boronic acid or an ester thereof, with the proviso that if $CG^1$ represents a boronic ester or an ester or derivative thereof, $CG^2$ stands for a leaving group, and vice versa;
and
$R^{2A}$, t, $R^2$, $R^3$, $R^4$, and $R^5$ are as defined for general formula (I), supra.

In another preferred embodiment, the invention relates to a method for preparing a compound of general formula (I), supra, from compounds of general formula (In1), wherein $CG^1$ represents a leaving group LG. Preferably, the leaving group LG represents a chlorine atom or a bromine atom or a trifluoromethylsulphonyloxy or nonafluorobutylsulphonyloxy group. More preferably, the leaving group LG represents a chlorine atom or a bromine atom. Even more preferably, the leaving group LG represents a chlorine atom.

In another preferred embodiment, the invention relates to a method for preparing a compound of general formula (I), supra, from compounds of general formula (In1), wherein $CG^1$ represents a boronic acid or an ester thereof. Preferably $CG^1$ represents

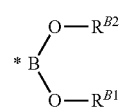

wherein * indicates the point of attachment of said group with the rest of the molecule;
$R^{B1}$ and $R^{B2}$
  represent, independently from each other, a hydrogen atom or a $C_1$-$C_6$-alkyl- or $C_3$-$C_6$-cycloalkyl-group;
or
$R^{B1}$ and $R^{B2}$ together represent a $C_1$-$C_6$-alkylene group.

The conversion which finally results in a compound of general formula (I) as defined supra, can be a one- or a two-step conversion.

A one-step conversion is to be understood as meaning a reaction of a compound of general formula (In1) as defined supra, with a compound of general formula

in which $R^1$ represents

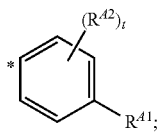

wherein * indicates the point of attachment of said groups with the rest of the molecule;
$R^{A1}$, $R^{A2}$ and t are as defined for the compounds of formula (I), supra, and $CG^2$ represents a suitable functional group via which the $R^1$ of the $R^1$—$CG^2$ compound can be coupled, by a coupling reaction, onto the $CG^1$-bearing carbon atom of the compound of formula (In1), thereby replacing said $CG^1$ with said $R^1$ moiety;
thus providing a compound of general formula (I):

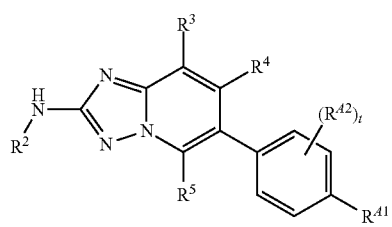

in which $R^{A1}$, $R^{A2}$, $R^2$, $R^3$, $R^4$, $R^5$, and t are as defined supra.

A two-step conversion is to be understood as meaning a reaction of a compound of general formula (In1) as defined supra, with a compound of general formula

in which
$R^{1a}$ represents

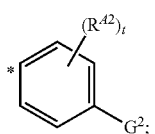

wherein * indicates the point of attachment of said groups with the rest of the molecule; $G^2$ represents —C(=O)OH, or a carboxylic acid ester, or —NH$_2$, or a protected amine; $R^{A2}$ and t are as defined for general formula (I), supra;
and $CG^2$ represents a suitable functional group via which the $R^{1a}$ of the $R^{1a}$—$CG^2$ compound can be coupled, by a coupling reaction, onto the $CG^1$-bearing carbon atom of the compound of formula (In1), thereby replacing said $CG^1$ with said $R^{1a}$ moiety;

thus providing a compound of general formula (7):

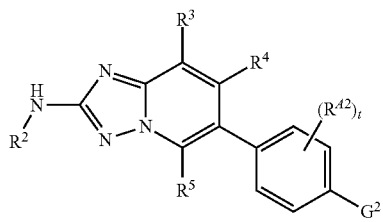

in which $R^{A2}$, $R^2$, $R^3$, $R^4$, $R^5$, and t are as defined for general formula (I), supra, and $G^2$ represents —C(=O)OH, or a carboxylic acid ester, or —NH$_2$, or a protected amine.

In a second step of the two-step conversion, the compound of the general formula (7), is then converted to a compound of general formula (I) by reacting the compound of the general formula (7), after de-protection of functional groups as the case may be, with a compound of formula $R^{1b}$—X, in which $R^{1b}$ represents —C(=O)$R^6$ or —N(H)$R^6$, wherein $R^6$ is as defined for general formula (I), supra, and X is a suitable functional group, via which the $R^{1b}$ of the $R^{1b}$—X compound can be coupled, via an amide coupling reaction, onto the —NH$_2$ or —COOH substituent of $G^2$.

The one-step conversion is preferred.

In case of the one-step conversion as well as in case of the two-step conversion, a first step (after protection of functional groups as may be necessary) is the formation of a C—C bond:

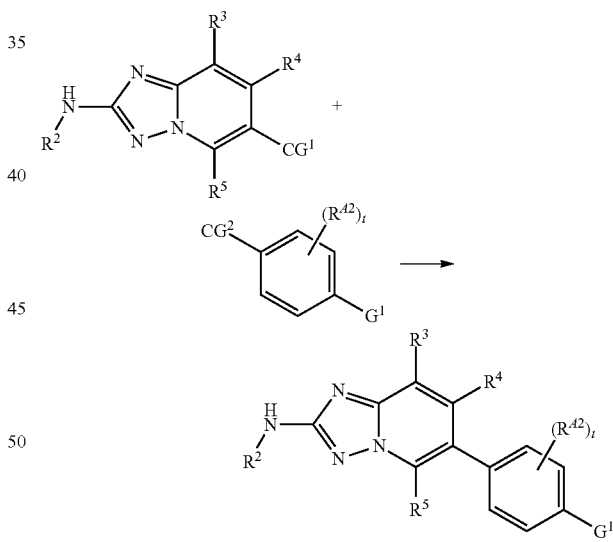

$G^1$ represents
$R^{A1}$, wherein $R^{A1}$ is as defined for general formula (I), supra, or
—C(=O)OH, or a carboxylic acid ester, or
—NH$_2$, or a protected amine.

Both $CG^1$ and $CG^2$ represent groups enabling palladium catalysed coupling reactions, such as chloro, bromo, iodo, trifluoromethylsulfonyloxy, or a boronic acid or an ester thereof, with the proviso that if $CG^1$ represents a boronic ester or an ester thereof, $CG^2$ stands for bromo, iodo, or trifluoromethylsulfonyloxy and the like, or vice versa.

The formation of a C—C bond can be achieved with the suitable reagents, as described above, in the presence of a suitable catalyst system, like for example Pd(OAc)$_2$ and P(oTol)$_3$, or PdCl$_2$(PPh$_3$)$_2$ and PPh$_3$, or Pd(OAc)$_2$ and P(tBu)$_3$, or Pd(OAc)$_2$ and BuPAd$_2$, or Pd(OAc)$_2$ and 2-dicyclohexylphosphino-2',6'-dimethoxy-1,1'-biphenyl, and a suitable base or mixture of bases, like for example aqueous potassium carbonate, potassium phosphate, cesium carbonate, potassium fluoride in a suitable solvent, like for example THF, DME, ethanol or 1-propanol or mixtures of these solvents.

In a preferred embodiment, the method of the present invention comprises the step of allowing a compound of general formula (In1):

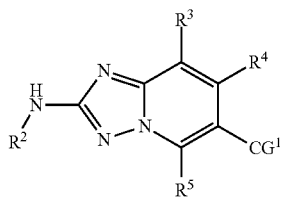
(In1)

in which R$^2$, R$^3$, R$^4$, and R$^5$ are as defined supra, and CG$^1$ is a leaving group, preferably a chlorine atom;
to react with a compound of general formula (In3):

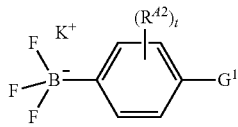
(In3)

in which:
G$^1$ represents
  R$^{A1}$, wherein R$^{A1}$ is as defined for general formula (I), supra, or
  —C(=O)OH, or a carboxylic acid ester, or
  —NH$_2$, or a protected amine;
and
R$^{A2}$ and t are as defined for general formula (I), supra;
thus providing a compound of general formula (Ia):

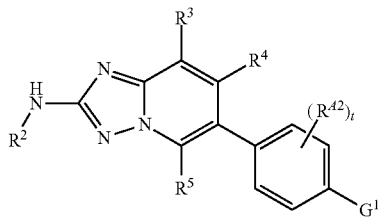
(Ia)

in which R$^{A2}$, R$^2$, R$^3$, R$^4$, R$^5$ and t are as defined supra, and G$^1$ represents
  R$^{A1}$, wherein R$^{A1}$ is as defined supra, or
  —C(=O)OH, or a carboxylic acid ester, or
  —NH$_2$, or a protected amine.

In another preferred embodiment, the method of the present invention comprises the step of allowing a compound of general formula (In1):

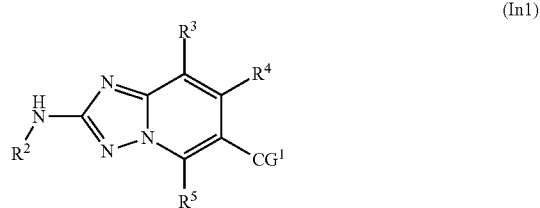
(In1)

in which R$^2$, R$^3$, R$^4$, and R$^5$ are as defined supra, and CG$^1$ is a leaving group, preferably a chlorine atom;
to react with a compound of general formula (In2):

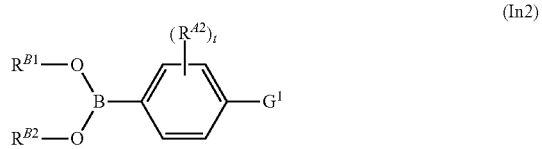
(In2)

in which:
G$^1$ represents
  R$^{A1}$, wherein R$^{A1}$ is as defined for general formula (I), supra, or
  —C(=O)OH, or a carboxylic acid ester, or
  —NH$_2$, or a protected amine;
R$^{B1}$ and R$^{B2}$
  represent, independently from each other, a hydrogen atom or a C$_1$-C$_6$-alkyl or C$_3$-C$_6$-cycloalkyl-group;
or
R$^{B1}$ and R$^{B2}$ together represent a C$_1$-C$_6$-alkylene group;
and
R$^{A2}$ and t are as defined for general formula (I), supra;
thus providing a compound of general formula (Ia):

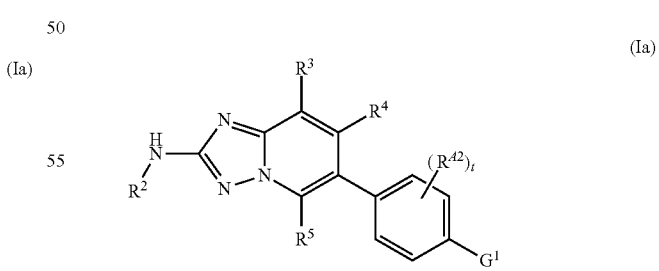
(Ia)

in which R$^{A2}$, R$^2$, R$^3$, R$^4$, R$^5$ and t are as defined supra, and G$^1$ represents
  R$^{A1}$, wherein R$^{A1}$ is as defined supra, or
  —C(=O)OH, or a carboxylic acid ester, or
  —NH$_2$, or a protected amine.

In another preferred embodiment, the method of the present invention comprises the step of allowing a compound of general formula (In1):

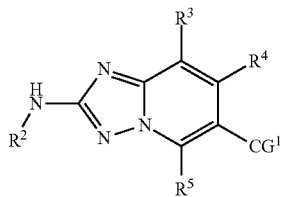
(In1)

in which $R^2$, $R^3$, $R^4$, and $R^5$ are as defined supra, and $CG^1$ represents

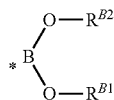

wherein * indicates the point of attachment of said group with the rest of the molecule;
$R^{B1}$ and $R^{B2}$
represent, independently from each other, a hydrogen atom or a $C_1$-$C_6$-alkyl or $C_3$-$C_6$-cycloalkyl-group;
or
$R^{B1}$ and $R^{B2}$ together represent a $C_1$-$C_6$-alkylene group;
to react with a compound of general formula (In4):

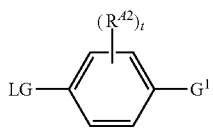
(In4)

in which:
$G^1$ represents
  $R^{A1}$, wherein $R^{A1}$ is as defined for general formula (I), supra, or
  —C(=O)OH, or a carboxylic acid ester, or
  —NH$_2$, or a protected amine;
LG represents a leaving group, preferably a bromine atom;
thus providing a compound of general formula (Ia):

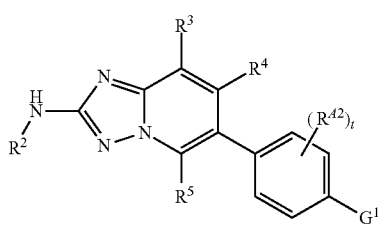
(Ia)

in which $R^{A2}$, $R^2$, $R^3$, $R^4$, $R^5$ and t are as defined supra, and $G^1$ represents
  $R^{A1}$, wherein $R^{A1}$ is as defined supra, or
  —C(=O)OH, or a carboxylic acid ester, or
  —NH$_2$, or a protected amine.

In a preferred embodiment $G^1$ represents $R^{A1}$, wherein $R^{A1}$ is as defined supra.
In another preferred embodiment $G^1$ represents —C(=O)OH.
In another preferred embodiment $G^1$ represents a protected amine. The protected amine preferably is a group of formula —N(H)PG$^2$, in which PG$^2$ preferably is —C(=O)O—C(CH$_3$)$_3$ or —C(=O)O-benzyl.
In another preferred embodiment $R^{B1}$ and $R^{B2}$ together represent a $C_1$-$C_6$-alkylene group. Preferably, $R^{B1}$ and $R^{B2}$ together represent —C(CH$_3$)$_2$—C(CH$_3$)$_2$— or —CH$_2$—C(H)(CH$_3$)—CH$_2$—.

It is to be understood that the present invention relates also to any combination of the preferred embodiments described above.

More particularly still, the present invention covers methods of preparation of the compounds of general formula (I) which are disclosed in the Example section of this text, infra.

In accordance with a further aspect, the present invention covers intermediate compounds which are useful in the preparation of compounds of the present invention of general formula (I), particularly in the method described herein. In particular, the present invention covers compounds of general formula (In1):

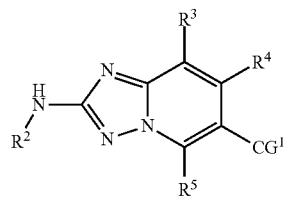
(In1)

in which $R^2$, $R^3$, $R^4$, and $R^5$ are as defined supra, and $CG^1$ is a leaving group, or $CG^1$ represents

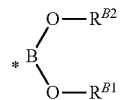

wherein * indicates the point of attachment of said group with the rest of the molecule;
$R^{B1}$ and $R^{B2}$
represent, independently from each other, a hydrogen atom or a $C_1$-$C_6$-alkyl or $C_3$-$C_6$-cycloalkyl-group;
or
$R^{B1}$ and $R^{B2}$ together represent a $C_1$-$C_6$-alkylene group.

The present invention also covers compounds of general formula (In2):

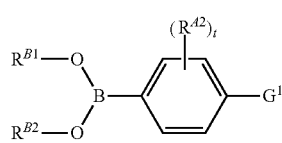
(In2)

in which:
$G^1$ represents
  $R^{A1}$, wherein $R^{A1}$ is as defined for general formula (I), supra, or
  —C(=O)OH, or a carboxylic acid ester, or
  —NH$_2$, or a protected amine;

$R^{B1}$ and $R^{B2}$
represent, independently from each other, a hydrogen atom or a $C_1$-$C_6$-alkyl or $C_3$-$C_6$-alkyl-group;
or
$R^{B1}$ and $R^{B2}$ together represent a $C_1$-$C_6$-alkylene group;
and
$R^{A2}$ and t are as defined for general formula (I), supra.

The present invention also covers compounds of general formula (In3):

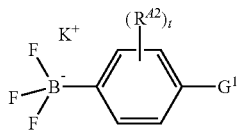

(In3)

in which:
$G^1$ represents
$R^{A1}$, wherein $R^{A1}$ is as defined for general formula (I), supra, or
—C(=O)OH, or a carboxylic acid ester, or
—NH$_2$, or a protected amine;
and
$R^{A2}$ and t are as defined for general formula (I), supra.

The present invention also covers compounds of general formula (In4):

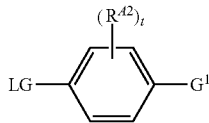

(In4)

in which:
$G^1$ represents
$R^{A1}$, wherein $R^{A1}$ is as defined for general formula (I), supra, or
—C(=O)OH, or a carboxylic acid ester, or
—NH$_2$, or a protected amine;
LG represents a leaving group;
and
$R^{A2}$ and t are as defined for general formula (I), supra.

As one of ordinary skill in the art is aware of, the methods described above may comprise further steps like e.g. the introduction of a protective group and the cleavage of the protective group. Particularly, if $R^{A1}$ or $R^9$ comprises an H$_2$N-group or a HO-group, these groups usually will be protected by suitable protective groups PG$^1$ and PG$^2$, as described herein, prior to the respective coupling reactions. The protective group will be removed after the coupling reaction.

Experimental Section

The following Table lists the abbreviations used in this paragraph, and in the Examples section. NMR peak forms are stated as they appear in the spectra, possible higher order effects have not been considered.

| Abbreviation | Meaning |
| --- | --- |
| Ac | acetyl |
| BINAP | 2,2'-bis(diphenylphosphino)-1,1'-binaphthyl |
| Boc | tert-butyloxycarbonyl |
| br | broad |
| Brett-Phos | 2-(dicyclohexylphosphino)-3,6-dimethoxy-2'-4'-6'-tri-i-propyl-1,1'-biphenyl |
| BuPAd$_2$ | Di(1-adamantyl)-n-butylphosphine |
| c- | cyclo- |
| D/d | doublet |
| Dd/dd | doublet of doublets |
| DCM | dichloromethane |
| DMAP | N,N-dimethylpyridin-4-amine |
| DME | 1,2-dimethoxyethane |
| DIPE | diisopropylether |
| DIPEA/DIEA | N,N-diisopropylethylamine |
| DMF | N,N-dimethylformamide |
| DMSO | dimethyl sulfoxide |
| Dppf | 1,1'-bis(diphenylphosphino)ferrocene |
| Eq | equivalent |
| ESI | electrospray ionisation |
| h/hrs | hour/hours |
| HATU | N-[(dimethylamino)(3H-[1,2,3]triazolo[4,5-b]pyridin-3-yloxy)-methylene]-N-methyl-methanaminium hexafluorophosphate |
| Hünig Base | N,N-diisopropylethylamine |
| LiHMDS | lithium bis(trimethylsilyl)amide (alternative name: lithium hexamethyldisilazide) |
| M/m | multiplet |
| m.p. | melting point in ° C. |
| MS | mass spectrometry |
| MW | molecular weight |
| NaOtBu | sodium tert-butoxide; sodium 2-methylpropan-2-olate |
| NMP | N-methylpyrrolidinone |
| NMR | nuclear magnetic resonance spectroscopy: chemical shifts (δ) are given in ppm. |
| P(tBu)$_3$ | Tri-tert-butylphosphine |
| PdCl$_2$(PPh$_3$)2 | dichlorobis(triphenylphosphine)palladium(II) |
| Pd(dba)$_2$ | bis-(dibenzylideneacetone)palladium(0) complex |
| Pd$_2$(dba)$_3$ | tris-(dibenzylideneacetone)dipalladium(0) chloroform complex |
| Pd(dppf)Cl$_2$ | dichloro[1,1'-bis(diphenylphosphino)ferrocene]palladium(II) |
| Pd(dppf)Cl$_2$•CH$_2$Cl$_2$ | dichloro[1,1'-bis(diphenylphosphino)ferrocene]palladium(II) dichloromethane adduct |
| Pd-Brett-Phos-pre-cat | chloro[2-(dicyclohexylphosphino)-3,6-dimethoxy-2'-4'-6'-tri-iso-propyl-1,1'-biphenyl][2-(2-amino-ethyl)phenyl]palladium(II) |
| Pd-tBu—X-Phos-pre-cat | chloro(2-di-tert-butylphosphino-2',4',6'-tri-isopropyl-1,1'-biphenyl)[2-(2-aminoethyl)phenyl] palladium(II), |
| Pd—X-Phos-pre-cat | chloro(2-dicyclohexylphosphino-2',4',6'-tri-isopropyl-1,1'-biphenyl)[2-(2-aminoethyl)phenyl] palladium(II) methyl-tert-butylether adduct |
| PPh$_3$ | triphenylphosphine |
| P(oTol)$_3$ | tri-o-tolylphosphine |
| q | quartet |
| Quin/quin | quintett |
| Rac | racemic |
| Rt/r.t. | room temperature |
| RT | retention time in minutes |
| s | singlet |
| sept | septet |
| t | triplet |
| TBAF | tetrabutylammoniumfluoride |
| tBu—X-Phos | 2-di-tert-butylphosphino-2',4',6'-tri-isopropyl-1,1'-biphenyl |
| TBDPS | tert-butyldiphenylsilyl |
| TBTU | N-[(1H-benzotriazol-1-yloxy)(dimethylamino)methyl-ene]-N-methylmethanaminium tetrafluoroborate |
| TEA | triethylamine |
| TFA | trifluoroacetic acid |
| THF | tetrahydrofuran |
| TMS | trimethylsilyl |
| Ts | para toluenesulfonyl; (tosyl) |
| UPLC | ultra performance liquid chromatography |
| X-Phos | 2-dicyclohexylphosphino-2',4',6'-triisopropylbiphenyl |

The schemes and procedures described below illustrate general synthetic routes to the compounds of general formula (I) as well as to intermediates thereof, and are not intended to be limiting. It is clear to the person skilled in the art that the order of transformations as exemplified in the Schemes can be modified in various ways. The order of transformations exemplified in the Schemes is therefore not intended to be limiting. In addition, interconversion of any of the substituents, $R^1$, $R^2$, $R^3$, $R^4$, $R^{5a}$, $R^{5b}$, $R^6$, $R^7$ or $R^8$ can be achieved before and/or after the exemplified transformations. These modifications can be such as the introduction of protective groups, cleavage of protective groups, reduction or oxidation of functional groups, halogenation, metallation, substitution or other reactions known to the person skilled in the art. These transformations include those which introduce a functionality which allows for further interconversion of substituents. Appropriate protective groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

A first reaction scheme is outlined infra:
Synthesis of Compounds of General Formula (I) of the Present Invention as Well as Intermediates Thereof $R^1$, $R^{1a}$, $R^{1b}$, $R^{A1}$, $R^{A2}$, t, $R^2$, $R^3$, $R^4$, and $R^5$ are as defined supra, Y preferably is a halogen atom as defined supra, and Z represents a suitable functional group via which the $R^1$ of the $R^1$—Z compound can be coupled, by a coupling reaction, onto the Y-bearing carbon atom of a compound (4), thereby replacing said Y with said $R^1$ moiety. Many aryl halides of the formula $R^2$—Y may be obtained commercially. Reagents of the general structure $R^{1a}$—Z and $R^1$—Z can for example be aryl boronic acids or aryl boronic esters. Many such reagents of the general structures $R^{1a}$—Z and $R^1$—Z are also commercially available. Reagents of the general structures $R^{1a}$—Z and $R^1$—Z can be prepared from aryl halides [see for example K. L. Billingslay, T. E. Barde, S. L Buchwald, Angew. Chem. 2007, 119, 5455 or T. Graening, Nachrichten aus der Chemie, January 2009, 57, 34].

$R^{1a}$ can be converted to $R^1$ in one or several steps. Typically, $R^{1a}$ can be a protected aryl-amine, especially-aryl-NH-Boc, or an aryl-carboxylic acid, [-aryl-C(O)OH] or an -aryl-

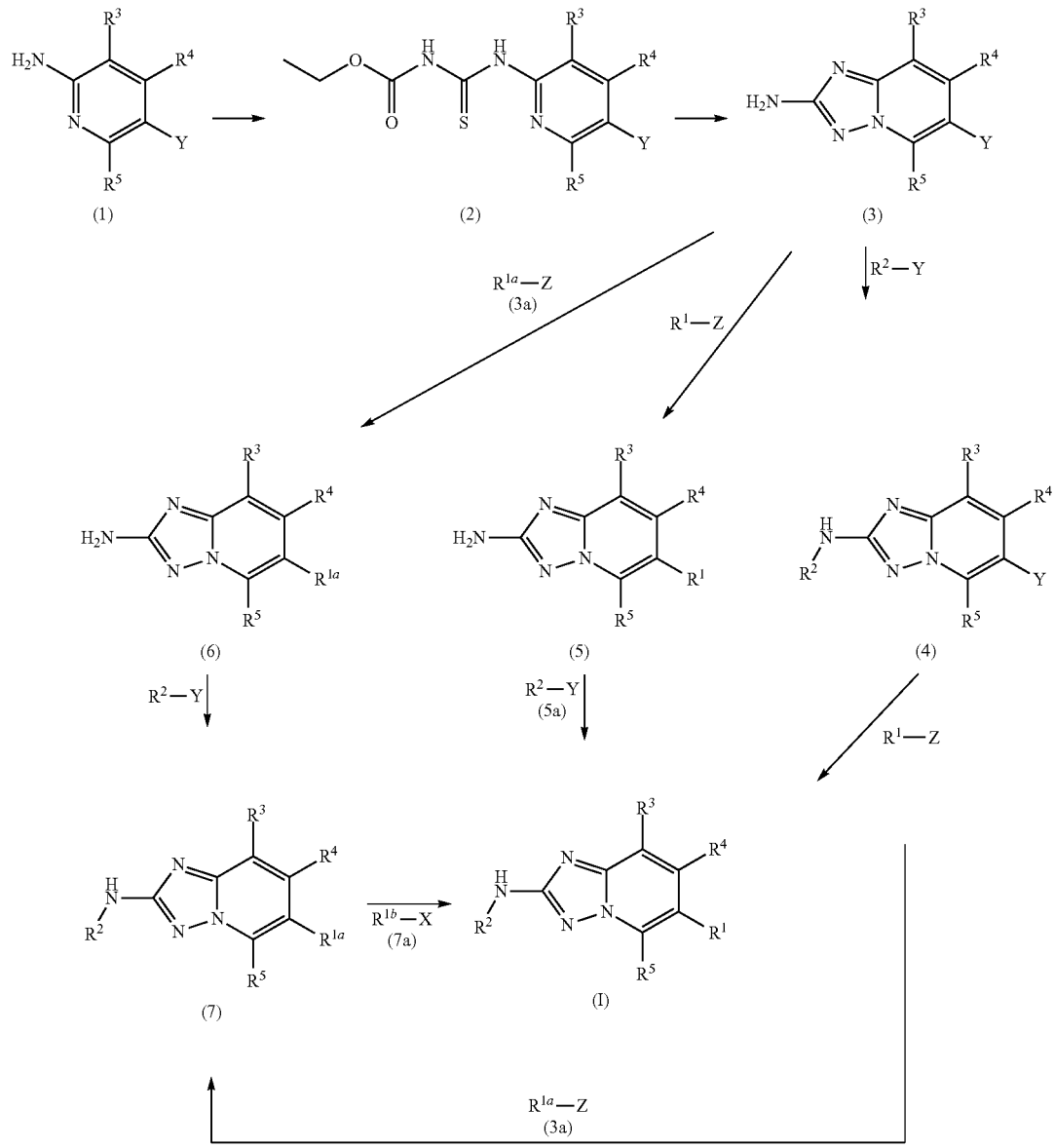

Scheme 1 carboxylic acid ester [-aryl-C(O)O-alkyl]. For example, when $R^{1a}$ is an aryl group to which an —$NH_2$ substituent is bound, it may be allowed to react with a compound of general formula $R^{1b}$—X (7a), in which $R^{1b}$ is —C(=O)$R^6$, —C(=O)$NR^6R^7$, —S(=O)$R^6$, or —S(=O)$_2R^6$, ($R^6$ and $R^7$ being as defined as for compounds of general formula (I) of the present invention as defined in the claims), and X is a suitable functional group (e.g. an —OH, —O—$C_1$-$C_6$-alkyl group, or a halogen atom), via which the $R^{1b}$ of the $R^{1b}$—X compound (7a) can be coupled, via a coupling reaction, such as an amide coupling reaction for example, onto the —$NH_2$ substituent bound to the aryl group $R^{1a}$ of compound (7), thereby replacing said X with said $R^{1a}$, thus providing a compound of general formula (I) of the present invention.

The person skilled in the art will recognise that there are many precedented methods for synthesising suitable 3,4,6-substituted 5-halo-pyridin-2-ylamines of general formula (I); some 3,4,6-substituted 5-halo-pyridin-2-ylamines may be obtained commercially.

A suitably substituted 5-halo-pyridin-2-ylamine intermediate of general formula (I) is converted to the corresponding intermediate of general formula (2) by reaction with a suitable oxycarbonylisothiocyanat, such as for example ethoxycarbonylisothiocyanat at temperatures ranging from room temperature to the boiling point of the solvent, preferably room temperature [see for example M. Nettekoven, B. Püllmann, S. Schmitt, Synthesis 2003, 1643-1652].

Intermediates of general formula (2) may be converted to 6-Halo-[1,2,4]triazolo[1,5-a]pyridin-2-ylamine intermediates of general formula (3) by reaction with a suitable reagent, for example hydroxylamine hydrochloride, in presence of a suitable base, such as, for example DIPEA in a suitable solvent system, such as, for example, methanol, ethanol, 1-propanol, 2-propanol or mixtures of these solvents at elevated temperatures, e.g. 60° C. [see for example M. Nettekoven, B. Püllmann, S. Schmitt, Synthesis 2003, 1643-1652].

Intermediates of general formula (3) can reacted with suitable aryl halides, preferably aryl bromides, in the presence of a suitable base, such as, for example NaOtBu or cesium carbonate, and a suitable catalyst/ligand system, such as for example $Pd_2(dba)_3$/rac-BINAP in a suitable solvent such as THF, toluene, DME, or NMP, or mixtures of these solvents at temperatures ranging from room temperature to the 200° C., to yield compounds of general formula (4). The person skilled in the art will recognise that the appropriate choice of reaction conditions, such as temperature, choice of solvent and catalyst system is critical for preferred derivatization at the amino group of intermediates of general formula (3). Intermediates of general formula (4) can be converted to compounds of general formula (I) by reaction with a suitable reagent, like for example a boronic acid derivative in the presence of a suitable catalyst system, like for example $Pd(OAc)_2$ and $P(oTol)_3$, or $PdCl_2(PPh_3)_2$ and $PPh_3$ and a suitable base, like for example aqueous potassium carbonate in a suitable solvent, like for example THF, DME, ethanol or 1-propanol or mixtures of these solvents at temperatures ranging from room temperature to 200° C., preferably the boiling point of the used solvent.

In an alternative route for the synthesis of compounds of general formula (I), Intermediates of general formula (3) can be reacted with a suitable reagent, like for example a boronic acid derivative in the presence of a suitable catalyst system, like for example $Pd(OAc)_2$ and $P(oTol)_3$, or $PdCl_2(PPh_3)_2$ and $PPh_3$ and a suitable base, like for example aqueous potassium carbonate in a suitable solvent, like for example THF, DME, ethanol or 1-propanol or mixtures of these solvents at temperatures ranging from room temperature to 200° C., preferably the boiling point of the used solvent to furnish intermediates of the general formula (5).

Intermediates of general formula (5) can be converted to compounds of general formula (I) by reaction with suitable aryl halides, of formula (5a) as defined herein, preferably aryl bromides, or aryl trifluoromethylsulphonates or aryl nonafluorobutylsulphonates, for example, optionally in the presence of a suitable base, such as, for example NaOtBu or cesium carbonate, and a suitable catalyst/ligand system, such as for example $Pd_2(dba)_3$/rac-BINAP in a suitable solvent such as for example THF, toluene, DME, or NMP, or mixtures of these solvents at temperatures ranging from room temperature to the 200° C.

Also as depicted in Scheme 1, is a further alternative route for the synthesis of compounds of general formula (I): Intermediates of general formula (3) can be converted to intermediates of general formula (6) by a coupling reaction as described supra for synthesis of intermediate of general formula (5), thereby replacing said Y with said $R^{1a}$ moiety.

Intermediates of general formula (6) can then be converted to intermediates of general formula (7) by a coupling reaction as described supra for synthesis of intermediates of general formula (4).

Intermediates of general formula (7) can then be converted to compounds of general formula (I) by one or more further transformations. These can be modifications such as cleavage of protective groups, reduction or oxidation of functional groups, halogenation, metallation, substitution or other reactions known to the person skilled in the art, for example the formation of an amide bond, the formation of a urea, or the formation of a sulfonamide.

Also as depicted in Scheme 1, is a further alternative route for the synthesis of compounds of general formula (I): Intermediates of general formula (4) can be converted to intermediates of general formula (7) by a coupling reaction as described herein, thereby replacing said Y with said $R^{1a}$ moiety.

The conversion can be conducted with a suitable reagent, like for example a boronic acid derivative in the presence of a suitable catalyst system, like for example $Pd(OAc)_2$ and $P(oTol)_3$, or $PdCl_2(PPh_3)_2$ and $PPh_3$, or $Pd(OAc)_2$ and $P(tBu)_3$, or $Pd(OAc)_2$ and $BuPAd_2$, or $Pd(OAc)_2$ and 2-dicyclohexylphosphino-2',6'-dimethoxy-1,1'-biphenyl, and a suitable base or mixture of bases, like for example aqueous potassium carbonate, potassium phosphate, cesium carbonate, potassium fluoride in a suitable solvent, like for example THF, DME, ethanol or 1-propanol or mixtures of these solvents at temperatures ranging from room temperature to 200° C., preferably the boiling point of the used solvent to furnish intermediates of the general formula (7).

Each of the Schemes 2-7, infra, illustrates specific transformations for the synthesis of some selected compounds according to general formula (I).

Scheme 2: Synthesis of compounds of general formula (11)

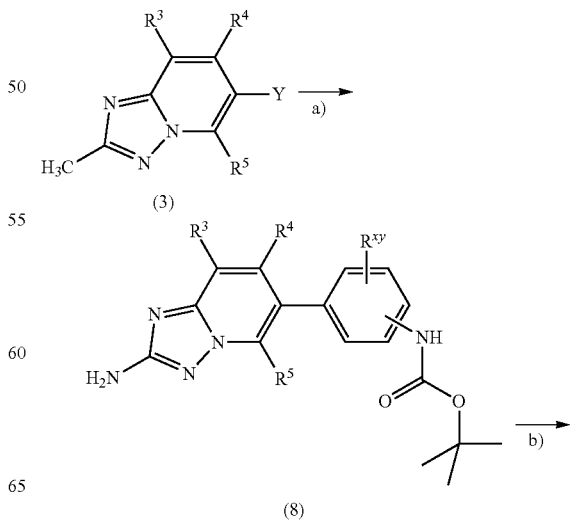

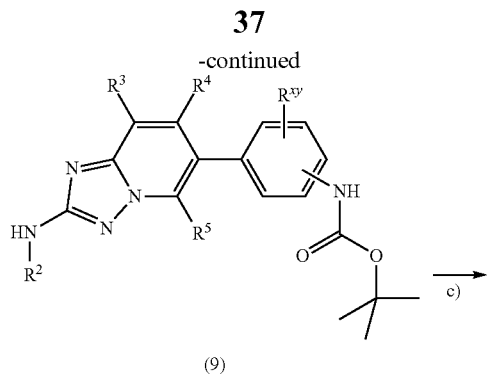

(9)

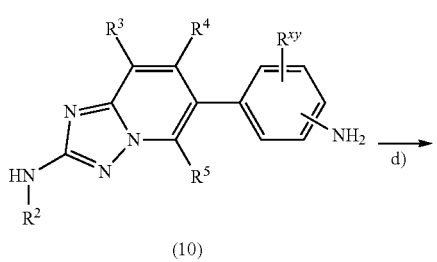

(10)

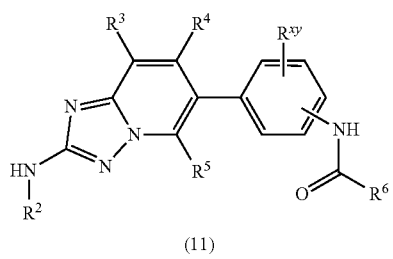

(11)

Scheme 2: Synthesis of compounds of general formula (11), wherein $R^2$, $R^3$, $R^4$, $R^5$ and $R^6$ are as defined for the compounds of general formula (I), supra. Y is a halogen as defined in the definitions. $R^{xy}$ is halogen, hydroxy or $C_1$-$C_6$-alkyl. a) coupling reaction using conditions as described supra for synthesis of intermediates of general formula (5); b) coupling reaction using conditions as described supra for synthesis of intermediates of general formula (4); c) removal of a Boc-protective group using conditions known to the person skilled in the art (see for example T. W. Greene and P. G. M. Wuts in *Protective Groups in Organic Synthesis*, 3$^{rd}$ edition, Wiley 1999); d) conditions for the formation of an amide bond, e.g. using coupling reagents like HATU or TBTU and a base like potassium carbonate or DIPEA in an inert solvent like THF, DMF, DCM or NMP.

Scheme 3: Synthesis of compounds of general formula (12)

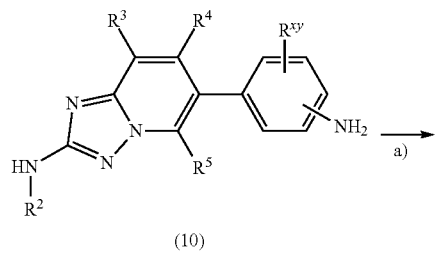

(10)

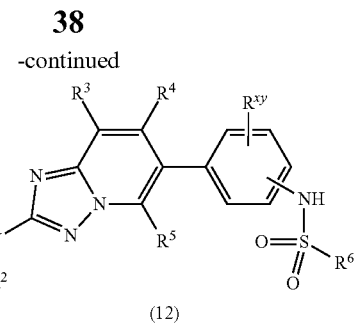

(12)

Scheme 3: Synthesis of compounds of general formula (12), wherein $R^2$, $R^3$, $R^4$, $R^5$ and $R^6$ are as defined for the compounds of general formula (I), supra. $R^{xy}$ is halogen, hydroxy or $C_1$-$C_6$-alkyl. a) conditions for the formation of a sulfonamide, e.g. using a sulfonyl chloride and a base like DIPEA in an inert solvent like for example THF, DMF, DCM or NMP at temperatures ranging from room temperature to the 70° C.

Scheme 4: Synthesis of compounds of general formula (13)

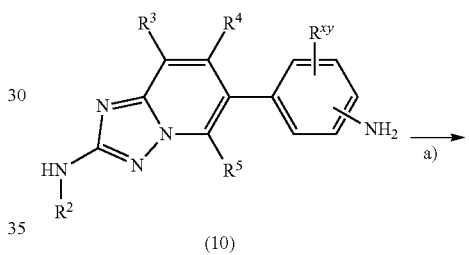

(10)

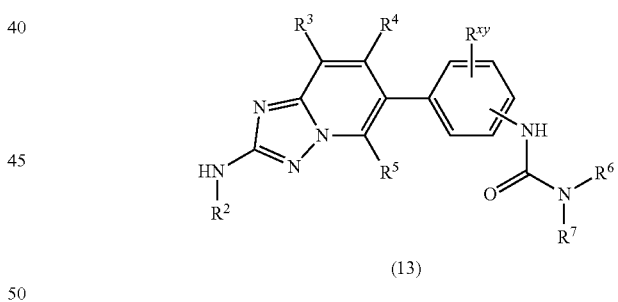

(13)

Scheme 4: Synthesis of compounds of general formula (13), wherein $R^2$, $R^3$, $R^4$, $R^5$, $R^6$ and $R^7$ are as defined for the compounds of general formula (I), supra. $R^{xy}$ is halogen, hydroxy or $C_1$-$C_6$-alkyl. a) Conditions for the formation of an urea, e.g. using an isocyanate in an inert solvent like for example THF, DMF, DCM or NMP at temperatures ranging from room temperature to 70° C. Alternatively, a two step procedure which involves reaction of 4-Nitrophenyl chloroformate in an inert solvent like for example THF or DCM and a base like pyridine at temperatures ranging from 0° C. to room temperature, followed by reaction with an amine in an inert solvent like THF or DCM at temperatures ranging from 0° C. to 40° C., can be used.

Scheme 5: Synthesis of compounds of general formula (15)

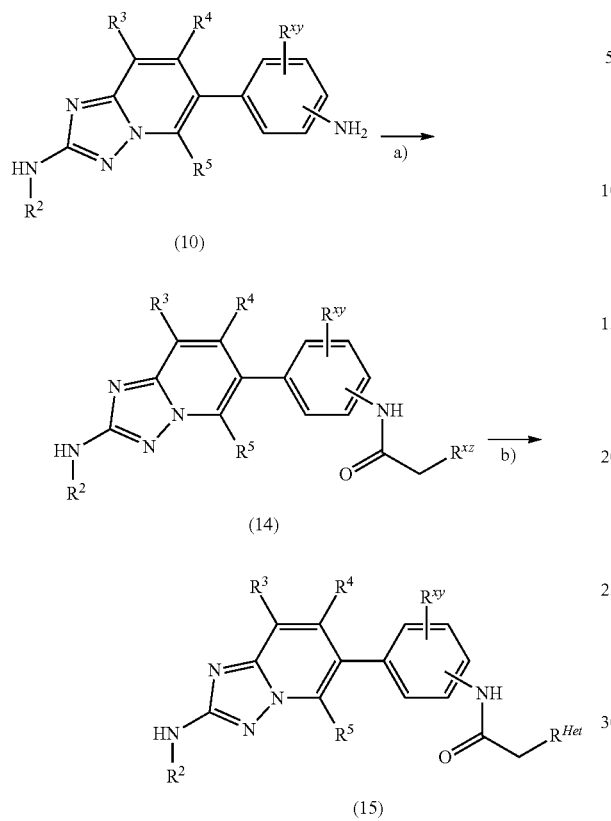

Scheme 5: Synthesis of compounds of general formula (15), wherein $R^2$, $R^3$, $R^4$, and $R^5$ are as defined for the compounds of general formula (I), supra. $R^{xy}$ is halogen, hydroxy or $C_1$-$C_6$-alkyl. $R^{xz}$ is a leaving group, e.g. a halogen. $R^{Het}$ is 3- to 10-membered heterocyclyl, as defined supra. a) Conditions for the formation of an amide bond, e.g. using coupling reagents like for example HATU or TBTU and a base like for example potassium carbonate or DIPEA in an inert solvent like for example THF, DMF, DCM or NMP. Alternatively, an acid chloride and a base like for example pyridine can be used in an inert solvent like for example THF or DCM. b) Reaction with a heterocyclic amine, like e.g. piperidine in a polar solvent like for example DMF or NMP using a base like for example potassium carbonate and optionally using a catalytic amount of potassium iodide.

Scheme 6: Synthesis of compounds of general formula (11)

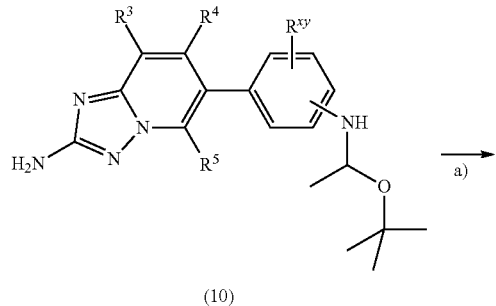

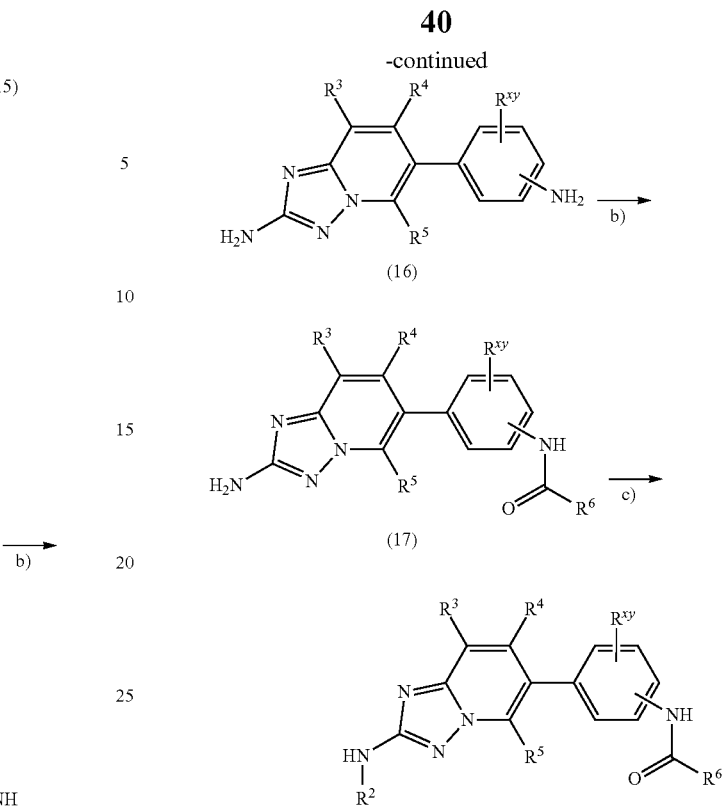

Scheme 6: Synthesis of compounds of general formula (11), wherein $R^2$, $R^3$, $R^4$, $R^5$ and $R^6$ are as defined for the compounds of general formula (I), supra. $R^{xy}$ is halogen, hydroxy or $C_1$-$C_6$-alkyl. a) removal of a Boc-protective group using conditions known to the person skilled in the art (see for example T. W. Greene and P. G. M. Wuts in *Protective Groups in Organic Synthesis*, 3$^{rd}$ edition, Wiley 1999); b) conditions for the formation of an amide bond, e.g. using coupling reagents like for example HATU or TBTU and a base like for example potassium carbonate or DIPEA in an inert solvent like for example THF, DMF, DCM or NMP; c) coupling reaction using conditions as described supra for synthesis of intermediates of general formula (4).

Scheme 7: Synthesis of compounds of general formula (22)

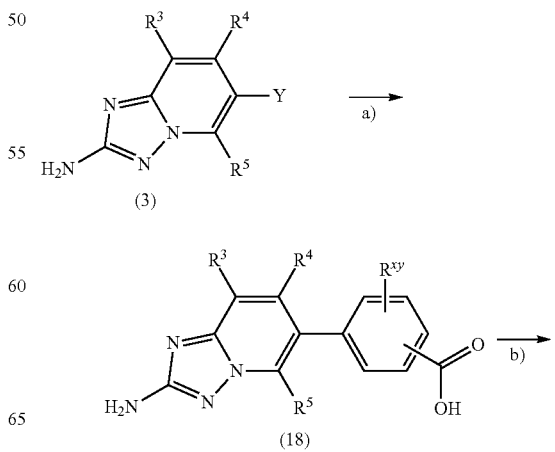

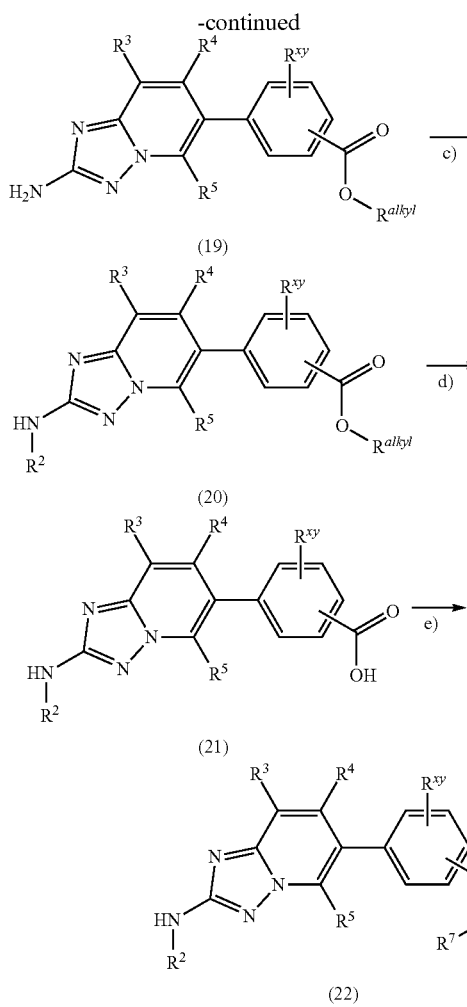

Scheme 7: Synthesis of compounds of general formula (21), wherein $R^2$, $R^3$, $R^4$, $R^5$, $R^6$ and $R^7$ are as defined for the compounds of general formula (I), supra. $R^{xy}$ is halogen, hydroxy or $C_1$-$C_6$-alkyl. $R^{alkyl}$ is $C_1$-$C_6$-alkyl. a) coupling reaction using conditions as described supra for synthesis of intermediates of general formula (5); b) formation of an ester using conditions known to the person skilled in the art (see for example T. W. Greene and P. G. M. Wuts in *Protective Groups in Organic Synthesis*, 3$^{rd}$ edition, Wiley 1999), e.g. using thionyl chloride in the appropriate alcohol at temperatures ranging from room temperature to 100° C.; c) coupling reaction using conditions as described supra for synthesis of intermediates of general formula (4); d) hydrolysis for an ester using conditions known to the person skilled in the art (see for example T. W. Greene and P. G. M. Wuts in *Protective Groups in Organic Synthesis*, 3$^{rd}$ edition, Wiley 1999), e.g. sodium hydroxide in a mixture of THF, methanol an water at r.t.; e) conditions for the formation of an amide bond, e.g. using coupling reagents like for example HATU or TBTU and a base like for example potassium carbonate or DIPEA in an inert solvent like for example THF, DMF, DCM or NMP.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be stirred out using a suitable solvent. In some cases, the compounds may be purified by chromatography, particularly flash chromatography, using for example pre-packed silica gel cartridges, e.g. from Separtis such as Isolute® Flash silica gel (silica gel chromatography) or Isolute® Flash NH2 silica gel (aminophase-silica-gel chromatography) in combination with a suitable chromatographic system such as a Flashmaster II (Separtis) or an Isolera system (Biotage) and eluents such as, for example, gradients of hexane/ethyl acetate or DCM/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluants such as, for example, gradients of water and acetonitrile which may contain additives such as trifluoroacetic acid, formic acid or aqueous ammonia.

Analytical UPLC-MS was performed as follows:
Method A: System: UPLC Acquity (Waters) with PDA Detector and Waters ZQ mass spectrometer; Column: Acquity BEH C18 1.7 μm 2.1×50 mm; Temperature: 60° C.; Solvent A: Water+0.1% formic acid; Solvent B: acetonitrile; Gradient: 99% A→1% A (1.6 min)→1% A (0.4 min); Flow: 0.8 mL/min; Injection Volume: 1.0 μl (0.1 mg-1 mg/mL sample concentration); Detection: PDA scan range 210-400 nm—Fixed and ESI (+), scan range 170-800 m/z Synthesis of Intermediate Compounds Intermediate Example Int01.01

Ethyl [(5-bromopyridin-2-yl)carbamothioyl]carbamate

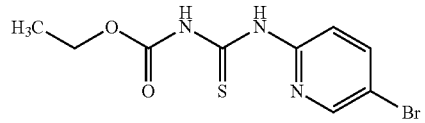 [SMILES: CCOC(=O)NC(=S)Nc1ccc(Br)cn1]

Ethoxycarbonylisothiocyanate (16.7 g) was added to a stirred solution of 2-amino-5-brompyridine (20 g) in dioxane (200 mL). The mixture was stirred for 2 h at r.t. A white solid precipitated. Hexane (20 mL) was added and the white solid was collected by filtration.

Yield: 30.4 g of the title compound.

$^1$H-NMR (300 MHz, DMSO-$d_6$): δ [ppm]=1.22 (t, 3H), 4.19 (q, 2H), 8.08 (dd, 1H), 8.49 (d, 1H), 8.57 (br. d, 1H), 11.37-12.35 (m, 2H).

Intermediate Example Int01.02

6-Bromo[1,2,4]triazolo[1,5-a]pyridin-2-amine

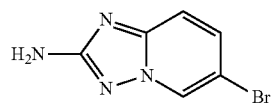

Hydroxylammonium chloride (39.8 g) was suspended in methanol (200 mL) and ethanol (190 mL) and Hünig Base (59 mL) was added at r.t. The mixture was heated to 60° C., Int01.01 (30 g) was added portionwise, and the mixture was stirred at 60° C. for 2 h. The solvent was removed in vacuum and water (150 mL) was added. A solid was collected by filtration and was washed with water and dried in vacuum.

Yield: 19.3 g of the title compound.

$^1$H-NMR (300 MHz, DMSO-d$_6$): δ [ppm]=6.10 (s, 2H), 7.28 (dd, 1H), 7.51 (dd, 1H), 8.88 (dd, 1H).

Intermediate Example Int01.03 tert-butyl [4-(2-amino[1,2,4]triazolo[1,5-a]pyridin-6-yl)phenyl]carbamate

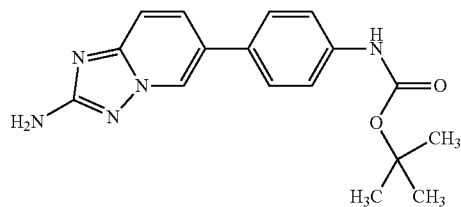 [SMILES: CC(C)(C)OC(=O)Nc1ccc(-c2ccc3nc(N)nn3c2)cc1]

To a stirred solution of Int01.02 (5.82 g) in 1-propanol (400 mL) was added 2M potassium carbonate solution (41 mL), {4-[(tert-butoxycarbonyl)amino]phenyl}boronic acid (8.6 g), triphenylphosphine (150 mg) and PdCl$_2$(PPh$_3$)$_2$ (1.9 g). The mixture was heated to reflux for 4 h, the solvent was removed in vacuum, water (150 mL) was added and the mixture was extracted with ethyl acetate (500 mL). The organic phase was dried (sodium sulfate), filtered through Celite and the solvent was removed in vacuum. The residue was triturated with DCM to give the title compound as a white solid. Yield: 7.2 g.

$^1$H-NMR (400 MHz, DMSO-d$_6$): δ [ppm]=1.37-1.55 (m, 9H), 5.99 (s, 2H), 7.36 (dd, 1H), 7.48-7.55 (m, 2H), 7.55-7.62 (m, 2H), 7.69 (dd, 1H), 8.78 (dd, 1H), 9.44 (s, 1H).

Intermediate Example Int01.04

6-(4-aminophenyl)[1,2,4]triazolo[1,5-a]pyridin-2-amine

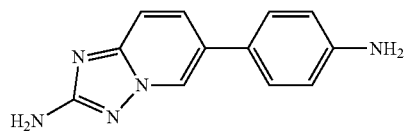 [SMILES: Nc1ccc(-c2ccc3nc(N)nn3c2)cc1]

To a stirred suspension of Int01.03 (7.05 g) in DCM (210 mL) was added TFA (66 mL). The mixture was stirred at r.t. for 1 h. The mixture was concentrated in vacuum. A saturated solution of potassium carbonate was added, until pH 10 was reached and the mixture was extracted for three times with DCM and methanol (10:1). The organic phase was dried (sodium sulfate) and the solvent was removed in vacuum to give 4.6 g of the title compound.

$^1$H-NMR (300 MHz, DMSO-d$_6$): δ [ppm]=5.26 (s, 2H), 5.95 (s, 2H), 6.64 (d, 2H), 7.29-7.45 (m, 3H), 7.64 (dd, 1H), 8.60-8.70 (m, 1H).

Intermediate Example Int01.05

N-[4-(2-amino[1,2,4]triazolo[1,5-a]pyridin-6-yl)phenyl]-2-(4-fluorophenyl)propanamide

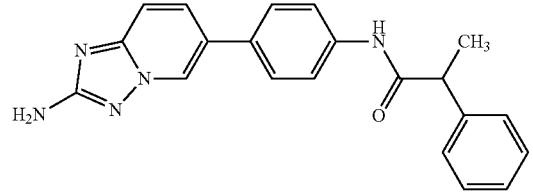 [SMILES: CC(C(=O)Nc1ccc(-c2ccc3nc(N)nn3c2)cc1)c1ccccc1]

To a stirred solution of Int01.04 (3.80 g) in DMF (350 mL) was added potassium carbonate (11.6 g), Int09.02 (5.67 g) and HATU (12.8 g). The mixture was stirred at room temperature for 2 h. Water was added, the mixture was stirred for 15 minutes and the mixture was extracted with ethyl acetate. The organic phase was washed with saturated sodium chloride solution, dried (sodium sulfate) and the solvent was removed in vacuum. The crude product was triturated with ethyl acetate to give 4.07 g of the title compound.

$^1$H-NMR (400 MHz, DMSO-d$_6$): δ [ppm]=1.39 (d, 3H), 3.83 (q, 1H), 5.98 (s, 2H), 7.08-7.17 (m, 2H), 7.32-7.44 (m, 3H), 7.60-7.67 (m, 4H), 7.70 (dd, 1H), 8.79 (d, 1H), 10.13 (s, 1H).

Intermediate Example Int02.01 methyl 4-bromo-3-methoxybenzoate

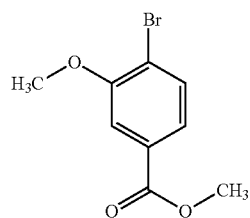

To a stirred solution of methyl 4-bromo-3-hydroxybenzoate (10.0 g) in DMF (50 mL) was added potassium carbonate (17.9 g) and iodomethane (9.2 mg). The mixture was stirred at room temperature for 2 h. Ethyl acetate was added and the mixture was washed with water. The organic phase was washed with saturated sodium chloride solution, dried (sodium sulfate) and the solvent was removed in vacuum to give 10 g of the title compound, that was used without further purification.

$^1$H-NMR (400 MHz, DMSO-d$_6$): δ [ppm]=3.82 (s, 3H), 3.87 (s, 3H), 7.41 (dd, 1H), 7.47 (d, 1H), 7.67 (d, 1H).

Intermediate Example Int02.02

4-bromo-3-methoxybenzoic acid

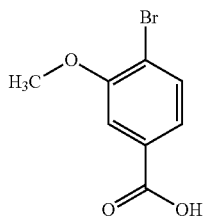

To a stirred solution of methyl 4-bromo-3-methoxybenzoate (11.2 g) in THF (130 mL), methanol (45 mL) and water (45 mL) was added a 1 M solution of lithium hydroxide in water (140 mL). The mixture was stirred at room temperature for 1 h. The solvent was removed in vacuum. Water was added and 1 N hydrochloric acid was added with ice bath cooling until pH 4 was reached. The precipitated solid was collected by filtration, washed with water and dried in vacuum to give 10.1 g of the title compound, that was used without further purification.

$^1$H-NMR (300 MHz, DMSO-d$_6$): δ [ppm]=3.87 (s, 3H), 7.42 (dd, 1H), 7.50 (d, 1H), 7.68 (d, 1H), 13.21 (br. s., 1H).

Intermediate Example Int02.03

4-bromo-3-methoxy-N-(2,2,2-trifluoroethyl)benzamide

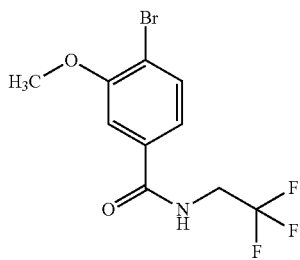 [SMILES: COc1cc(C(=O)NCC(F)(F)F)ccc1Br]

To a stirred suspension of 4-bromo-3-methoxybenzoic acid (2.0 g) in THF (100 mL) was added 2,2,2-trifluoroethylamine (1.26 g), HATU (3.87 g), and DIPEA (1.7 ml). The mixture was stirred at room temperature for 12 h. Water (350 ml) and saturated sodium bicarbonate solution (350 ml) were added. The organic phase was separated and the aqueous phase was extracted with ethyl acetate. The combined organic extracts were dried (sodium sulfate) and the solvent was removed in vacuum. Silica gel chromatography gave 2.57 g of the title compound.

$^1$H-NMR (400 MHz, DMSO-d$_6$): δ [ppm]=3.92 (s, 3H), 4.11 (qd, 2H), 7.43 (dd, 1H), 7.56 (d, 1H), 7.72 (d, 1H), 9.19 (t, 1H).

Intermediate Example Int02.04 azetidin-1-yl(4-bromo-3-methoxyphenyl)methanone

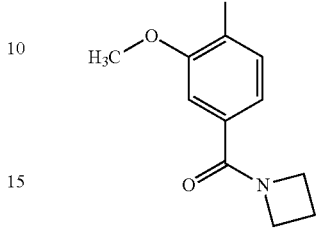

To a stirred solution of 4-bromo-3-methoxybenzoic acid (400 mg) in DMF (4.0 mL) was added potassium carbonate (720 mg), azetidine (148 mg) and TBTU (890 mg). The mixture was stirred at room temperature for 60 h. Water was added, the mixture was stirred for 15 minutes and the solvent was removed in vacuum. Water was added and the mixture was extracted with ethyl acetate. The organic phase was washed with saturated sodium chloride solution, dried (sodium sulfate) and the solvent was removed in vacuum. Silica gel chromatography gave 370 mg of the title compound.

$^1$H-NMR (400 MHz, DMSO-d$_6$): δ [ppm]=2.15-2.27 (m, 2H), 3.85 (s, 3H), 4.00 (t, 2H), 4.26 (t, 2H), 7.07 (dd, 1H), 7.21 (d, 1H), 7.61 (d, 1H).

Intermediate Example Int02.05

(4-Bromo-3-methoxyphenyl)(3-fluoroazetidin-1-yl)methanone

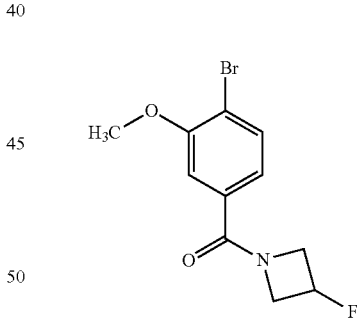

To a stirred solution of 4-bromo-3-methoxybenzoic acid (1.4 g) in DMF (15 mL) was added potassium carbonate (2.51 g), 3-fluoroazetidine hydrochloride (1.01 g) and HATU (3.69 g). The mixture was stirred at room temperature for 18 h. Water was added, the mixture was stirred for 15 minutes and the solvent was removed in vacuum. Water was added and the mixture was extracted with ethyl acetate. The organic phase was washed with water, saturated sodium chloride solution, dried (sodium sulfate) and the solvent was removed in vacuum, to give 1.25 g of the title compound.

$^1$H-NMR (400 MHz, DMSO-d$_6$): δ [ppm]=3.90 (s, 3H), 3.99-4.16 (m, 1H), 4.31-4.65 (m, 3H), 5.36 (tt, 0.5H), 5.50 (tt, 0.5H), 7.14 (dd, 1H), 7.26 (d, 1H), 7.66 (d, 1H).

Intermediate Example Int02.06

4-bromo-3-methoxy-N,N-dimethylbenzamide

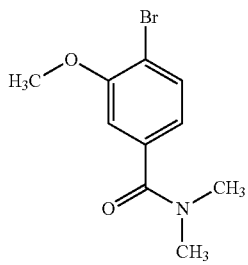

Starting with 4-bromo-3-methoxybenzoic acid and dimethyl amine, Int02.06 was prepared analogously to the procedure for the preparation of Int02.05.

Intermediate Example Int02.07

(4-bromo-3-methoxyphenyl)(pyrrolidin-1-yl)methanone

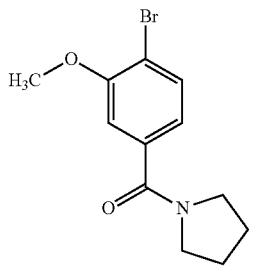 [SMILES: COc1cc(C(=O)N2CCCC2)ccc1Br]

Starting with 4-bromo-3-methoxybenzoic acid and pyrrolidine, Int02.07 was prepared analogously to the procedure for the preparation of Int02.04.

Intermediate Example Int03.01

1-bromo-2-methoxy-4-(methylsulfanyl)benzene

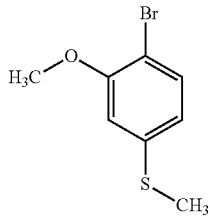

To a stirred solution of 1-bromo-4-fluoro-2-methoxybenzene (4.0 g) in DMF (40 mL) was added sodium methanethiolate (2.76 g). The mixture was stirred at room temperature for 30 minutes and at 85° C. for 2 h. Water was added and the mixture was extracted with ethyl acetate. The organic phase was washed with saturated sodium chloride solution, dried (sodium sulfate) and the solvent was removed in vacuum. Silica gel chromatography gave 280 mg of the title compound.

$^1$H-NMR (400 MHz, DMSO-$d_6$): δ [ppm]=2.46 (s, 3H), 3.82 (s, 3H), 6.74 (dd, 1H), 6.91 (d, 1H), 7.44 (d, 1H).

1-bromo-2-methoxy-4-(methylsulfanyl)benzene

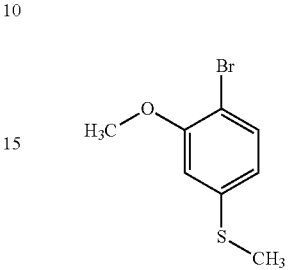

To a stirred solution of 1-bromo-4-fluoro-2-methoxybenzene (10.0 g) in DMF (100 mL) was added sodium methanethiolate (4.44 g). The mixture was stirred at 65° C. for 2 h. The mixture was cooled to 0° C. and methyl iodide (4.55 mL) was added. The mixture was stirred at room temperature for 1 h and further sodium methanethiolate (4.44 g) was added. The mixture was stirred at 65° C. for 1 h. The mixture was cooled to 0° C. and methyl iodide (4.55 mL) was added. The mixture was stirred at room temperature for 1 h. Water was added and the mixture was extracted with ethyl acetate. The organic phase was washed with saturated sodium chloride solution, dried (sodium sulfate) and the solvent was removed in vacuum. Silica gel chromatography gave 6.2 g of the title compound as a 2:1 mixture with the starting material. The mixture was used for the next step without purification.

Intermediate Example Int03.02

1-bromo-2-methoxy-4-(methylsulfonyl)benzene

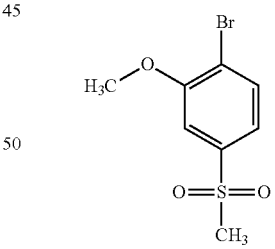

To a stirred solution of Int03.01 (265 mg) in chloroform (10 mL) was added 3-chlorobenzenecarboperoxoic acid (mCPBA) (890 mg). The mixture was stirred at room temperature for 1 h. A half-saturated solution of sodium bicarbonate was added and the mixture was extracted with dichloromethane. The organic phase was washed with saturated sodium chloride solution, dried (sodium sulfate) and the solvent was removed in vacuum. Silica gel chromatography gave 252 mg of the title compound.

$^1$H-NMR (300 MHz, DMSO-$d_6$): δ [ppm]=3.22 (s, 3H), 3.93 (s, 3H), 7.39 (dd, 1H), 7.50 (d, 1H), 7.84 (d, 1H).

Intermediate Example Int04.01

1-bromo-2-ethoxy-4-fluorobenzene

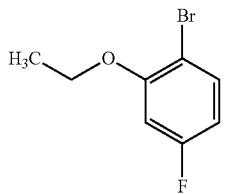

To a stirred solution of 2-bromo-5-fluorophenol (5.0 g) in DMF (30 mL) was added potassium carbonate (10.8 g) and iodoethane (6.12 g). The mixture was stirred at room temperature for 16 h. The solvent was removed in vacuum. Water was added and the mixture was extracted with a mixture of ethyl acetate and hexane (3:1). The organic phase was washed with saturated sodium chloride solution, dried (sodium sulfate) and the solvent was removed in vacuum, to give 5.06 g of the title compound as a crude product, that was used for the next step without purification.

$^1$H-NMR (400 MHz, DMSO-$d_6$): δ [ppm]=1.31 (t, 3H), 4.08 (q, 2H), 6.71 (td, 1H), 7.00 (dd, 1H), 7.55 (dd, 1H).

Intermediate Example Int04.02

1-bromo-2-ethoxy-4-(methylsulfanyl)benzene

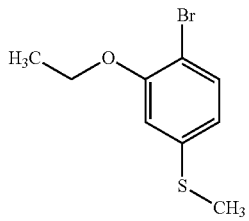

To a stirred solution of 1-bromo-2-ethoxy-4-fluorobenzene (2.0 g) in DMF (20 mL) was added sodium methanethiolate (1.66 g). The mixture was stirred for 2 h at 65° C. The mixture was cooled to room temperature and ethyl iodide (1.3 mL) was added. The mixture was stirred at room temperature for 1 h. Water was added and the mixture was extracted with ethyl acetate. The organic phase was washed with saturated sodium chloride solution, dried (sodium sulfate) and the solvent was removed in vacuum. Silica gel chromatography gave 1.65 g of the title compound.

$^1$H-NMR (400 MHz, DMSO-$d_6$): δ [ppm]=1.24-1.36 (m, 3H), 2.45 (s, 3H), 4.08 (q, 2H), 6.73 (dd, 1H), 6.89 (d, 1H), 7.43 (d, 1H).

Intermediate Example Int04.03

1-bromo-2-ethoxy-4-(methylsulfonyl)benzene

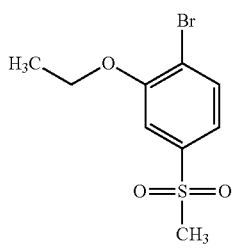

To a stirred solution of Int04.02 (1.65 g) in chloroform (65 mL) was added 3-chlorobenzenecarboperoxoic acid (mCPBA) (4.49 g). The mixture was stirred at room temperature for 16 h. With ice bath cooling, a half-saturated solution of sodium bicarbonate and a 0.2 M solution of sodium thiosulfate was added, the mixture was stirred for 30 minutes and the mixture was extracted with dichloromethane. The organic phase was washed with saturated sodium chloride solution, dried (sodium sulfate) and the solvent was removed in vacuum. Silica gel chromatography gave 1.35 g of the title compound.

$^1$H-NMR (300 MHz, DMSO-$d_6$): δ [ppm]=1.35 (t, 3H), 3.22 (s, 3H), 4.20 (q, 2H), 7.37 (dd, 1H), 7.48 (d, 1H), 7.84 (d, 1H).

Intermediate Example Int05.01

1-bromo-4-fluoro-2-(2,2,2-trifluoroethoxy)benzene

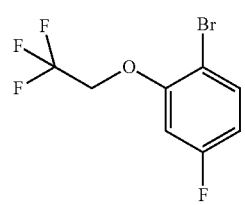 [SMILES: Fc1ccc(Br)c(OCC(F)(F)F)c1]

To a stirred solution of 2-bromo-5-fluorophenol (1.5 g) in acetonitrile (0.5 mL) and DMF (8.5 mL) in a microwave tube was added potassium carbonate (2.1 g) and 2,2,2-trifluoroethyl trifluoromethanesulfonate (2.37 g). The mixture was heated to 150° C. in a microwave oven for 30 minutes. In a second microwave tube the same reaction was repeated. Both mixtures were combined. The solvent was removed in vacuum, ethyl acetate and hexane (1:1) was added and the mixture was washed with water. The organic phase was washed with saturated sodium chloride solution, dried (sodium sulfate) and the solvent was removed in vacuum. Silica gel chromatography gave 4.0 g of the title compound.

$^1$H-NMR (300 MHz, CHLOROFORM-d): δ [ppm]=4.39 (q, 2H), 6.62-6.78 (m, 2H), 7.53 (dd, 1H).

Intermediate Example Int05.02

1-bromo-4-(methylsulfanyl)-2-(2,2,2-trifluoroethoxy)benzene

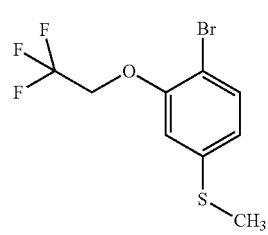

To a stirred solution of Int05.01 (4.0 g) in DMF (15 mL) was added sodium methanethiolate (1.0 g). The mixture was stirred for 2 h at 60° C. The mixture was cooled to room temperature. Water was added and the mixture was extracted with ethyl acetate. The organic phase was washed with saturated sodium chloride solution, dried (sodium sulfate) and the solvent was removed in vacuum to give 3.8 g of the crude title compound, that was used for the next step without purification.

$^1$H-NMR (300 MHz, CHLOROFORM-d): δ [ppm]=2.48 (s, 3H), 4.39 (q, 2H), 6.78-6.88 (m, 2H), 7.46 (d, 1H).

Intermediate Example Int05.03

1-bromo-4-(methylsulfonyl)-2-(2,2,2-trifluoroethoxy)benzene

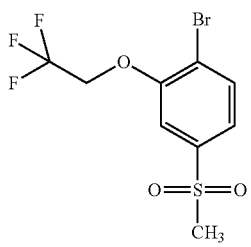

To a stirred solution of Int05.02 (3.8 g) in chloroform (100 mL) was added 3-chlorobenzenecarboperoxoic acid (mCPBA) (8.48 g). The mixture was stirred at room temperature for 16 h. With ice bath cooling, a half-saturated solution of sodium bicarbonate and a 0.2 M solution of sodium thiosulfate was added, the mixture was stirred for 30 minutes and the mixture was extracted with dichloromethane. The organic phase was washed with a 0.2 M solution of sodium thiosulfate and a saturated sodium chloride solution, dried (sodium sulfate) and the solvent was removed in vacuum. Silica gel chromatography gave a solid that was triturated with ether to give 2.1 g of the title compound.

$^1$H-NMR (400 MHz, CHLOROFORM-d): δ [ppm]=3.06 (s, 3H), 4.50 (q, 2H), 7.45 (d, 1H), 7.52 (dd, 1H), 7.81 (d, 1H).

Intermediate Example Int06.01 methyl 4-bromo-3-(2,2,2-trifluoroethoxy)benzoate

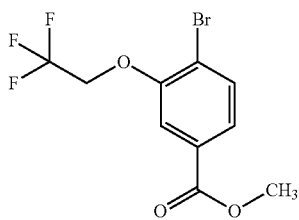 [SMILES: COC(=O)c1ccc(Br)c(OCC(F)(F)F)c1]

To a stirred solution of methyl 4-bromo-3-hydroxybenzoate (2.5 g) in acetonitrile (0.5 mL) and DMF (10 mL) in a microwave tube was added potassium carbonate (2.93 g) and 2,2,2-trifluoroethyl trifluoromethanesulfonate (2.79 g). The mixture was heated to 150° C. in a microwave oven for 30 minutes. The solvent was removed in vacuum, ethyl acetate was added and the mixture was washed with water. The organic phase was washed with saturated sodium chloride solution, dried (sodium sulfate) and the solvent was removed in vacuum. Recrystallization of the residue from ethanol gave 1.2 g of the title compound. The mother liquor was concentrated in vacuum and purified by aminophase-silica-gel chromatography followed by recrystallized from methanol and water to give further 0.64 g of the title compound.

$^1$H-NMR (300 MHz, CHLOROFORM-d): δ [ppm]=3.93 (s, 3H), 4.47 (q, 2H), 7.56 (d, 1H), 7.58-7.70 (m, 2H).

Intermediate Example Int06.02

4-bromo-3-(2,2,2-trifluoroethoxy)benzoic acid

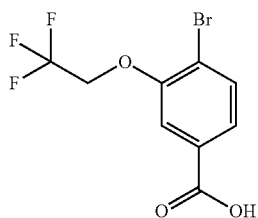 [SMILES: O=C(O)c1ccc(Br)c(OCC(F)(F)F)c1]

To a stirred solution of Int06.01 (1.83 g) in THF (30 mL), methanol (10 mL) and water (10 mL) was added a 1 M solution of lithium hydroxide in water (18 mL). The mixture was stirred at room temperature for 1 h. Water was added and 2 N hydrochloric acid was added until pH 4 was reached. The precipitated solid was collected by filtration, was washed with water. The solid was suspended with toluene and concentrated in vacuum. Trituration of the residue with hexane gave 1.6 g of the title compound.

$^1$H-NMR (300 MHz, DMSO-$d_6$): δ [ppm]=4.95 (q, 2H), 7.51 (dd, 1H), 7.65 (d, 1H), 7.74 (d, 1H), 13.29 (br. s., 1H).

Intermediate Example Int06.03

4-bromo-3-(2,2,2-trifluoroethoxy)benzamide

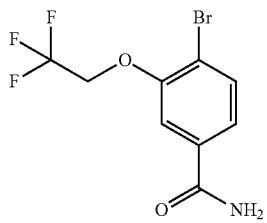 [SMILES: NC(=O)c1ccc(Br)c(OCC(F)(F)F)c1]

To a stirred suspension of Int06.02 (0.50 g) in THF (20 mL) was added DMF (0.2 mL) and oxalyl chloride (0.30 mL). The mixture was stirred at room temperature for 0.5 h. With ice bath cooling, ammonia gas was bubbled through the reaction mixture. A white solid precipitated. The mixture was stirred for further 15 minutes. Ethyl acetate was added and the mixture was washed with water and with a saturated solution of sodium chloride. The organic phase was dried (sodium sulfate) and the solvent was removed in vacuum to give a white solid. The solid was triturated with toluene and washed with toluene and hexanes to give 0.27 g of the title compound.

$^1$H-NMR (300 MHz, DMSO-$d_6$): δ [ppm]=4.88 (q, 2H), 7.45 (dd, 1H), 7.50 (br. s., 1H), 7.64 (d, 1H), 7.69 (d, 1H), 8.00 (br. s., 1H).

Intermediate Example Int06.04

[4-bromo-3-(2,2,2-trifluoroethoxy)phenyl](3-fluoroazetidin-1-yl)methanone

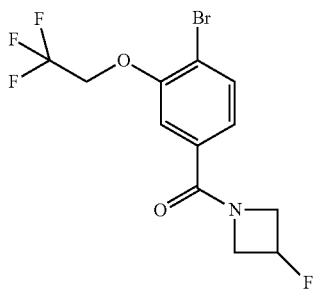 [SMILES: O=C(c1ccc(Br)c(OCC(F)(F)F)c1)N1CC(F)C1]

Starting with 4-bromo-3-(2,2,2-trifluoroethoxy)benzoic acid and 3-fluoroazetidine hydrochloride, Int06.04 was prepared analogously to the procedure for the preparation of Int02.06.

Intermediate Example Int06.05

[4-bromo-3-(2,2,2-trifluoroethoxy)phenyl](3-hydroxyazetidin-1-yl)methanone

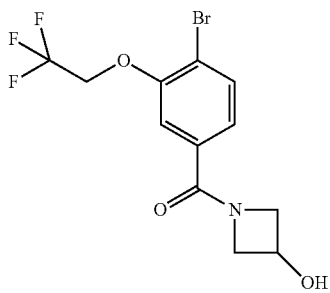 [SMILES: O=C(c1ccc(Br)c(OCC(F)(F)F)c1)N1CC(O)C1]

Starting with 4-bromo-3-(2,2,2-trifluoroethoxy)benzoic acid and azetidin-3-ol hydrochloride, Int06.05 was prepared analogously to the procedure for the preparation of Int02.03.

Intermediate Example Int06.06

[4-bromo-3-(2,2,2-trifluoroethoxy)phenyl](pyrrolidin-1-yl)methanone

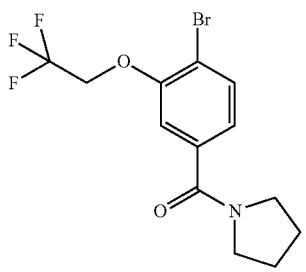 [SMILES: O=C(c1ccc(Br)c(OCC(F)(F)F)c1)N1CCCC1]

Starting with 4-bromo-3-(2,2,2-trifluoroethoxy)benzoic acid and pyrrolidin, Int06.06 was prepared analogously to the procedure for the preparation of Int02.05.

Intermediate Example Int07.01

3-(4-bromo-3-methoxyphenyl)-1,3-oxazolidin-2-one

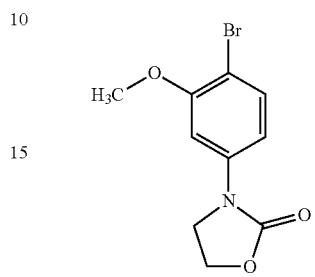

To a stirred solution of 4-Bromo-3-methoxy-aniline (10.0 g) in acetonitrile (176 mL) was added Hünig Base (25 mL) and 2-chloroethyl chloroformate (10.6 g). The mixture was stirred at room temperature for 0.5 h. The solvent was removed in vacuum. The residue was dissolved in tetrahydrofurane (250 mL), and potassium tert-butoxide (16.2 g) was added. The mixture was stirred at room temperature for 2 h. The solvent was removed in vacuum. The residue was dissolved in ethyl acetate and the mixture was washed with water and with saturated sodium chloride solution, dried (sodium sulfate) and the solvent was removed in vacuum. Silica gel chromatography gave a compound that was crystallized from ethanol. Yield: 7.7 g of the title compound. The mother liquor was concentrated in vacuum and aminophase-silica-gel chromatography gave a solid that was recrystallized from ethanol to give further 2.3 g of the title compound.
$^1$H-NMR (300 MHz, CHLOROFORM-d): δ [ppm]=4.00-4.10 (m, 2H), 4.45-4.55 (m, 2H), 6.66 (dd, 1H), 7.49 (d, 1H), 7.63 (d, 1H).

Intermediate Example Int08.010 tert-butyl [4-(2-{[2-methoxy-4-(methylsulfonyl)phenyl]amino}[1,2,4]triazolo-[1,5-a]pyridin-6-yl)phenyl]carbamate

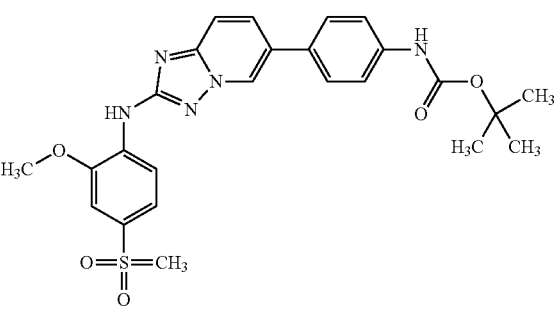

To a stirred suspension of Int01.03 (4.0 g) in toluene (250 mL) and NMP (25 mL) was added Int03.02 (8.31 g), chloro(2-dicyclohexylphosphino-2',4',6'-tri-isopropyl-1,1'-biphenyl)[2-(2-aminoethyl)phenyl] palladium(II) methyl-tert-butylether adduct (1.08 g), X-Phos (0.64 g) and powdered potassium phosphate (16.6 g). The flask was degassed twice and backfilled with argon. The mixture was heated to reflux for 16 h.

The reaction mixture was filtered through a microfilter and the solvent was removed in vacuum. The residue was triturated with dichloromethane to give 12.3 g of the title compound.

$^1$H-NMR (400 MHz, DMSO-d$_6$): δ [ppm]=1.46 (s, 9H), 3.16 (s, 3H), 3.96 (s, 3H), 7.43 (d, 1H), 7.48-7.59 (m, 3H), 7.63-7.72 (m, 3H), 7.92 (dd, 1H), 8.48 (d, 1H), 8.58 (s, 1H), 9.06-9.12 (m, 1H), 9.46 (s, 1H).

Intermediate Example Int08.010 (Procedure 1)

tert-butyl [4-(2-{[2-methoxy-4-(methylsulfonyl)phenyl]amino}[1,2,4]triazolo-[1,5-a]pyridin-6-yl)phenyl]carbamate

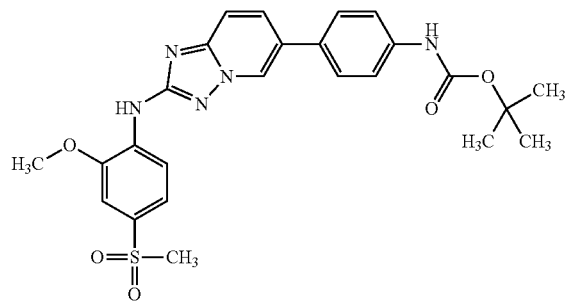

To a stirred suspension of Int21.03 (100 mg) in toluene (2.0 ml) was added {4-[(tert-butoxycarbonyl)amino]phenyl}boronic acid (100 mg), dicyclohexyl(2',6'-dimethoxybiphenyl-2-yl)phosphine (29 mg) and palladium acetate (6.5 mg) and the flask was degassed twice and backfilled with argon. The mixture was stirred for 5 minutes at r.t. Powdered potassium phosphate (120 mg) was added and the flask was degassed twice and backfilled with argon. The mixture was heated to 110° C. for 2 h. The reaction mixture was filtered through an aminophase-silica-gel column and the solvent was removed in vacuum. Aminophase-silica-gel chromatography gave 130 mg of the title compound.

$^1$H-NMR (300 MHz, DMSO-d$_6$), δ [ppm]=1.46 (9H), 3.16 (3H), 3.96 (3H), 7.42 (1H), 7.48-7.58 (3H), 7.63-7.71 (3H), 7.92 (1H), 8.48 (1H), 8.58 (1H), 9.06-9.10 (1H), 9.45 (1H).

Intermediate Example Int08.011

6-(4-aminophenyl)-N-[2-methoxy-4-(methylsulfonyl)phenyl][1,2,4]triazolo[1,5-a]pyridin-2-amine

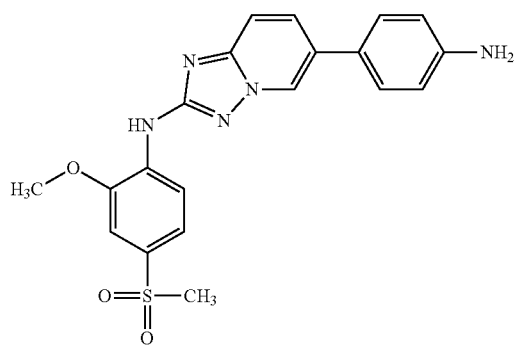 [SMILES: COc1cc(S(C)(=O)=O)ccc1Nc1nc2ccc(-c3ccc(N)cc3)cn2n1]

To a stirred suspension of Int08.010 (12.3 g) in dichloromethane (40 mL) was added TFA (46 mL). The mixture was stirred at room temperature for 16 h. Further TFA was added (1 mL) and the mixture was stirred at room temperature for 5 h. A saturated solution of potassium carbonate was added until pH 9 was reached. The mixture was extracted with dichloromethane and methanol (10:1 mixture). The solution was dried (sodium sulfate) and the solvent was removed in vacuum. The residue was triturated with ethanol to give 9.2 g of the title compound.

$^1$H-NMR (300 MHz, DMSO-d$_6$): δ [ppm]=3.16 (s, 3H), 3.95 (s, 3H), 5.30 (s, 2H), 6.63 (d, 2H), 7.38-7.46 (m, 3H), 7.51 (dd, 1H), 7.61 (d, 1H), 7.84 (dd, 1H), 8.48 (d, 1H), 8.55 (s, 1H), 8.93 (d, 1H).

Intermediate Example Int08.020 tert-butyl [4-(2-{[4-(methylsulfonyl)-2-(2,2,2-trifluoroethoxy)phenyl]amino}-[1,2,4]triazolo[1,5-a]pyridin-6-yl)phenyl]carbamate

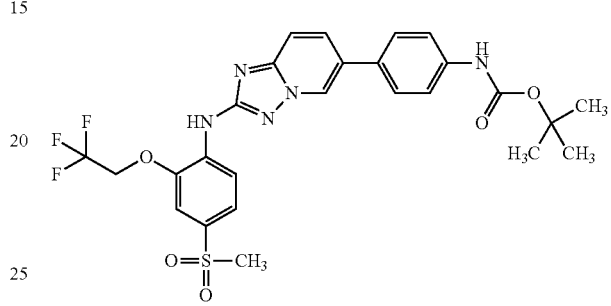

To a stirred suspension of Int01.03 (4.0 g) in toluene (77 mL) and NMP (7.7 mL) was added Int05.03 (4.91 g), chloro(2-dicyclohexylphosphino-2',4',6'-triisopropyl-1,1'-biphenyl)[2-(2-aminoethyl)phenyl] palladium(II) methyl-tert-butylether adduct (254 mg) and X-Phos (150 mg) and the flask was degassed twice and backfilled with argon. The mixture was stirred for 5 minutes at room temperature. Powdered potassium phosphate (9.13 g) was added and the flask was degassed twice and backfilled with argon. The mixture was heated to reflux for 1 h. The reaction mixture was filtered through an aminophase-silica-gel column and the solvent was removed in vacuum. Aminophase-silica-gel chromatography gave a solid that was triturated with a mixture of hexane and dichloromethane to give 6.05 g of the title compound.

$^1$H-NMR (400 MHz, DMSO-d$_6$): δ [ppm]=1.46 (s, 9H), 3.17 (s, 3H), 5.00 (q, 2H), 7.55 (d, 2H), 7.60-7.71 (m, 5H), 7.93 (dd, 1H), 8.50 (d, 1H), 8.54 (s, 1H), 9.09 (dd, 1H), 9.46 (s, 1H).

Intermediate Example Int08.021

6-(4-aminophenyl)-N-[4-(methylsulfonyl)-2-(2,2,2-trifluoroethoxy)phenyl]-[1,2,4]triazolo[1,5-a]pyridin-2-amine

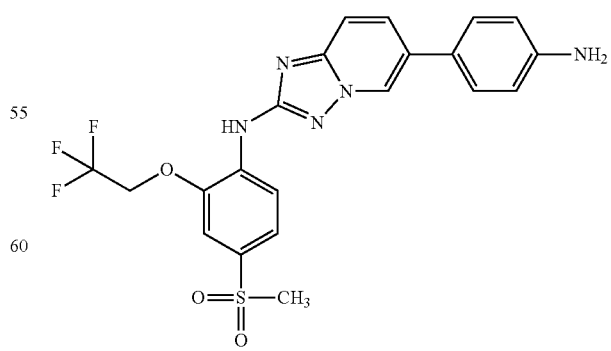

To a stirred suspension of Int08.020 (11.9 g) in dichloromethane (80 mL) was added TFA (40 mL). The mixture was stirred at room temperature for 24 h. The solvent was removed in vacuum, and the residue was dissolved in ethyl acetate. A half-saturated solution of sodium bicarbonate was added until pH 9 was reached. The precipitated solid was collected by filtration to give 9.7 g of the title compound.

$^1$H-NMR (400 MHz, DMSO-d$_6$): δ [ppm]=3.16 (s, 3H), 5.00 (q, 2H), 5.34 (br. s., 2H), 6.60-6.68 (m, 2H), 7.39-7.48 (m, 2H), 7.57-7.66 (m, 3H), 7.85 (dd, 1H), 8.48 (s, 1H), 8.51 (d, 1H), 8.89-8.96 (m, 1H).

Intermediate Example Int08.030 tert-butyl {4-[2-({2-methoxy-4-[(2,2,2-trifluoroethyl)carbamoyl]phenyl}-amino)[1,2,4]triazolo[1,5-a]pyridin-6-yl]phenyl}carbamate

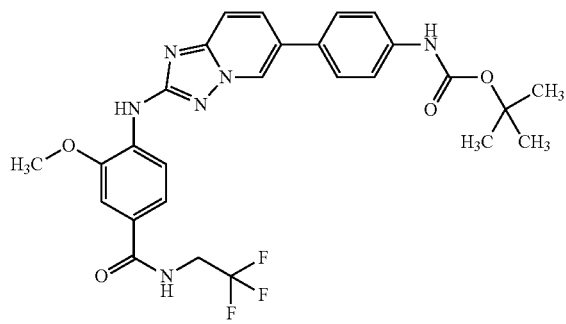 [SMILES: COc1cc(C(=O)NCC(F)(F)F)ccc1Nc1nc2ccc(-c3ccc(NC(=O)OC(C)(C)C)cc3)cn2n1]

To a stirred suspension of Int01.03 (500 mg) in toluene (10 mL) and NMP (0.5 mL) was added Int02.03 (576 mg), chloro(2-dicyclohexylphosphino-2',4',6'-tri-isopropyl-1,1'-biphenyl)[2-(2-aminoethyl)phenyl] palladium(II) methyl-tert-butylether adduct (64 mg), X-Phos (37 mg) and powdered potassium phosphate (1.14 g). The flask was degassed twice and backfilled with argon. The mixture was heated to reflux for 16 h. The solvent was removed in vacuum. Aminophase-silica-gel chromatography gave the title compound as a crude product (850 mg) that was used for the next step without further purification.

$^1$H-NMR (400 MHz, DMSO-d$_6$): δ [ppm]=1.46 (s, 9H), 3.93 (s, 3H), 4.01-4.15 (m, 2H), 7.51-7.60 (m, 4H), 7.62-7.71 (m, 3H), 7.90 (dd, 1H), 8.32 (s, 1H), 8.35 (d, 1H), 8.89 (t, 1H), 9.08 (d, 1H), 9.45 (s, 1H).

Intermediate Example Int08.031

4-{[6-(4-aminophenyl)[1,2,4]triazolo[1,5-a]pyridin-2-yl]amino}-3-methoxy-N-(2,2,2-trifluoroethyl)benzamide

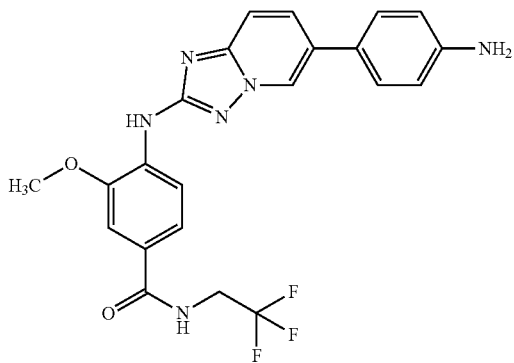 [SMILES: COc1cc(C(=O)NCC(F)(F)F)ccc1Nc1nc2ccc(-c3ccc(N)cc3)cn2n1]

To a stirred suspension of Int08.030 (850 mg) in dichloromethane (16 mL) was added TFA (3.0 mL). The mixture was stirred at room temperature for 4 h. Further TFA was added (1 mL) and the mixture was stirred at room temperature for 5 h. A saturated solution of potassium carbonate was added until pH 9 was reached. The mixture was extracted with dichloromethane and methanol (10:1 mixture). The solution was dried (sodium sulfate) and the solvent was removed in vacuum to give 690 mg of the title compound, that was used for the next step without further purification.

$^1$H-NMR (300 MHz, DMSO-d$_6$): δ [ppm]=3.92 (s, 3H), 3.98-4.16 (m, 2H), 5.29 (s, 2H), 6.63 (d, 2H), 7.43 (d, 2H), 7.50-7.62 (m, 3H), 7.82 (dd, 1H), 8.28 (s, 1H), 8.35 (d, 1H), 8.85-8.96 (m, 2H).

Intermediate Example Int08.040 tert-butyl (4-{2-[(4-carbamoyl-2-methoxyphenyl)amino][1,2,4]triazolo[1,5-a]-pyridin-6-yl}phenyl)carbamate

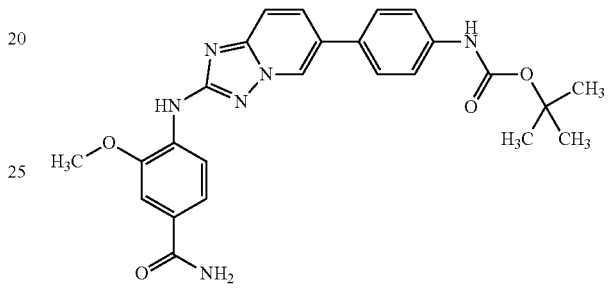

To a stirred suspension of Int01.03 (300 mg) in toluene (17 mL) and NMP (5.7 mL) was added 4-bromo-3-methoxybenzamide (276 mg), chloro(2-dicyclohexylphosphino-2',4',6'-triisopropyl-1,1'-biphenyl)[2-(2-aminoethyl)phenyl] palladium(II) methyl-tert-butylether adduct (38 mg) and X-Phos (22 mg) and the flask was degassed twice and backfilled with argon. The mixture was stirred for 5 minutes at room temperature. Powdered potassium phosphate (979 mg) was added and the flask was degassed twice and backfilled with argon. The mixture was heated to reflux for 1 h. The reaction mixture was filtered through an aminophase-silica-gel column and the solvent was removed in vacuum. Aminophase-silica-gel chromatography followed by preparative reverse phase HPLC gave a solid that was triturated with a mixture of dichloromethane and hexane to give 121 mg of the title compound.

$^1$H-NMR (400 MHz, DMSO-d$_6$): δ [ppm]=1.46 (s, 9H), 3.91 (s, 3H), 7.16 (br. s., 1H), 7.48-7.57 (m, 4H), 7.60-7.70 (m, 3H), 7.82 (br. s., 1H), 7.90 (dd, 1H), 8.22 (s, 1H), 8.31 (d, 1H), 9.03-9.13 (m, 1H), 9.45 (s, 1H).

Intermediate Example Int08.041

4-{[6-(4-aminophenyl)[1,2,4]triazolo[1,5-a]pyridin-2-yl]amino}-3-methoxybenzamide

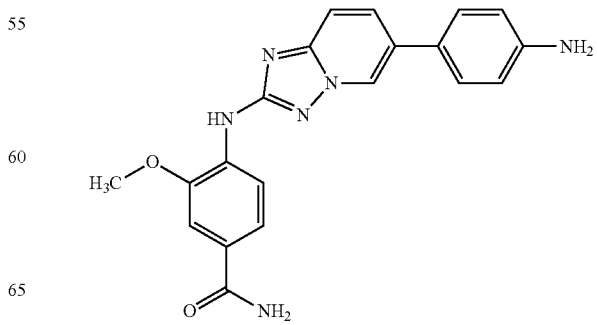

To a stirred suspension of Int08.040 (120 mg) in dichloromethane (3 mL) was added TFA (0.3 mL). The mixture was stirred at room temperature for 16 h. The solvent was removed in vacuum, and the residue was dissolved in ethyl acetate. A half-saturated solution of sodium bicarbonate was added until pH 9 was reached. The mixture was extracted with ethyl acetate. The organic phase was dried (sodium sulfate) and the solvent was removed in vacuum to give 84 mg of the title compound.

$^1$H-NMR (300 MHz, DMSO-d$_6$): δ [ppm]=3.90 (s, 3H), 5.29 (s, 2H), 6.63 (d, 2H), 7.18 (br. s., 1H), 7.43 (d, 2H), 7.47-7.62 (m, 3H), 7.75-7.89 (m, 2H), 8.19 (s, 1H), 8.31 (d, 1H), 8.93 (s, 1H).

Intermediate Example Int08.050 tert-butyl [4-(2-{[4-carbamoyl-2-(2,2,2-trifluoroethoxy)phenyl]amino}-[1,2,4]triazolo[1,5-a]pyridin-6-yl)phenyl]carbamate

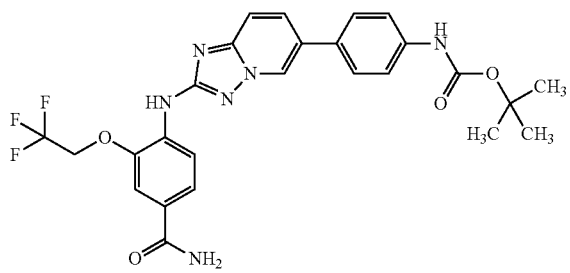 [SMILES: CC(C)(C)OC(=O)Nc1ccc(-c2ccc3nc(Nc4ccc(C(N)=O)cc4OCC(F)(F)F)nn3c2)cc1]

To a stirred suspension of Int01.03 (182 mg) in toluene (4 mL) and NMP (3 mL) was added chloro(2-dicyclohexylphosphino-2',4',6'-triisopropyl-1,1'-biphenyl)[2-(2-aminoethyl)phenyl] palladium(II) methyl-tert-butylether adduct (23 mg), X-Phos (13 mg) and powdered potassium phosphate (356 mg). The flask was degassed twice and backfilled with argon. The mixture was heated to reflux and Int06.03 (200 mg), dissolved in 1 mL NMP was added dropwise. The mixture was heated to reflux for 16 h. The solvent was removed in vacuum.

Aminophase-silica-gel chromatography followed by preparative reverse phase HPLC gave 150 mg of the title compound.

$^1$H-NMR (300 MHz, DMSO-d$_6$): δ [ppm]=1.46 (s, 9H), 4.89 (q, 2H), 7.26 (br. s., 1H), 7.54 (d, 2H), 7.59-7.72 (m, 5H), 7.83 (br. s., 1H), 7.91 (dd, 1H), 8.22 (s, 1H), 8.34 (d, 1H), 9.11 (s, 1H), 9.48 (s, 1H).

Intermediate Example Int08.051

4-{[6-(4-aminophenyl)[1,2,4]triazolo[1,5-a]pyridin-2-yl]amino}-3-(2,2,2-trifluoroethoxy)benzamide

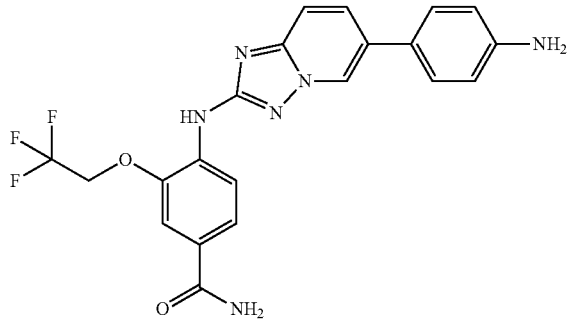 [SMILES: NC(=O)c1ccc(Nc2nc3ccc(-c4ccc(N)cc4)cn3n2)c(OCC(F)(F)F)c1]

To a stirred suspension of Int08.050 (130 mg) in dichloromethane (10 mL) was added TFA (0.5 mL). The mixture was stirred at room temperature for 2 h. Further TFA was added (3 mL) and the mixture was stirred at room temperature for 2 h. A saturated solution of potassium carbonate was added until pH 9 was reached. The mixture was extracted with dichloromethane and methanol (10:1 mixture). The solution was filtered through an aminophase-silica-gel column and the solvent was removed in vacuum to give 70 mg of the title compound. The crude product was used for the next step without further purification.

Intermediate Example Int08.060 tert-butyl {4-[2-({4-[(3-fluoroazetidin-1-yl)carbonyl]-2-methoxyphenyl}-amino)[1,2,4]triazolo[1,5-a]pyridin-6-yl]phenyl}carbamate

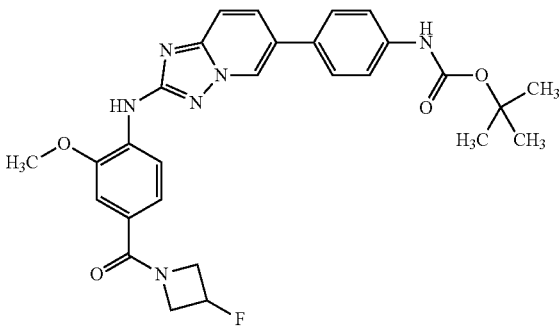 [SMILES: COc1cc(C(=O)N2CC(F)C2)ccc1Nc1nc2ccc(-c3ccc(NC(=O)OC(C)(C)C)cc3)cn2n1]

To a stirred suspension of Int01.03 (6.0 g) in toluene (350 mL) and NMP (29 mL) was added Int02.05 (6.91 g), chloro(2-dicyclohexylphosphino-2',4',6'-triisopropyl-1,1'-biphenyl)[2-(2-aminoethyl)phenyl] palladium(II) methyl-tert-butylether adduct (610 mg) and X-Phos (359 mg) and the flask was degassed twice and backfilled with argon. The mixture was stirred for 5 minutes at room temperature. Powdered potassium phosphate (13.7 g) was added and the flask was degassed twice and backfilled with argon. The mixture was heated to reflux for 1 h. The reaction mixture was filtered through an aminophase-silica-gel column and the solvent was removed in vacuum. Aminophase-silica-gel chromatography gave 7.9 g of the title compound.

$^1$H-NMR (300 MHz, DMSO-d$_6$): δ[ppm]=1.46 (s, 9H), 3.90 (s, 3H), 4.04-4.80 (m, 4H), 5.27-5.57 (m, 1H), 7.23 (d, 1H), 7.27 (dd, 1H), 7.54 (d, 2H), 7.59-7.71 (m, 3H), 7.89 (dd, 1H), 8.29 (s, 1H), 8.34 (d, 1H), 9.06 (d, 1H), 9.45 (s, 1H).

Intermediate Example Int08.061

(4-{[6-(4-aminophenyl)[1,2,4]triazolo[1,5-a]pyridin-2-yl]amino}-3-methoxy-phenyl)(3-fluoroazetidin-1-yl)methanone

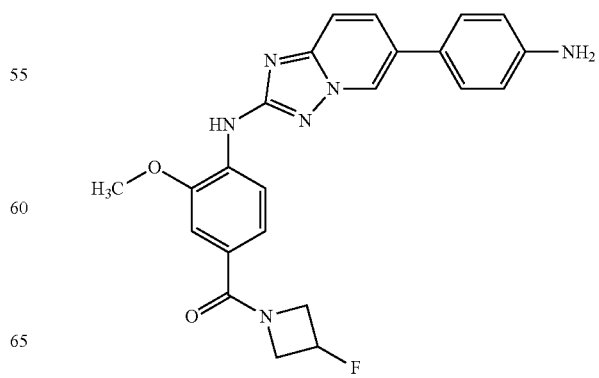

To a stirred suspension of Int08.060 (7.8 g) in dichloromethane (55 mL) was added TFA (28 mL). The mixture was stirred at room temperature for 16 h. The solvent was removed in vacuum and the residue was dissolved in ethyl acetate. A saturated solution of sodium bicarbonate was added until pH 9 was reached. The precipitated solid was collected by filtration to give 5.2 g of the title compound. The crude product was used for the next step without further purification.

$^1$H-NMR (300 MHz, DMSO-d$_6$): δ [ppm]=3.90 (s, 3H), 4.45 (br. s., 4H), 5.20-5.58 (m, 3H), 6.63 (d, 2H), 7.23 (d, 1H), 7.27 (dd, 1H), 7.42 (d, 2H), 7.52-7.61 (m, 1H), 7.81 (dd, 1H), 8.23 (s, 1H), 8.34 (d, 1H), 8.86-8.94 (m, 1H).

Intermediate Example Int08.070 tert-butyl [4-(2-{[4-(azetidin-1-ylcarbonyl)-2-methoxyphenyl]amino}[1,2,4]-triazolo[1,5-a]pyridin-6-yl)phenyl]carbamate

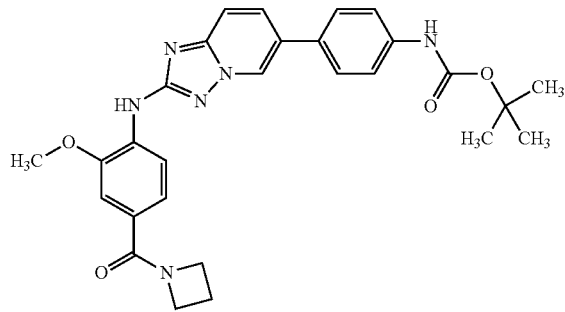 [SMILES: COc1cc(C(=O)N2CCC2)ccc1Nc1nc2ccc(-c3ccc(NC(=O)OC(C)(C)C)cc3)cn2n1]

To a stirred suspension of Int01.03 (672 mg) in toluene (13 mL) and NMP (1.3 mL) was added Int02.04 (670 mg), chloro(2-dicyclohexylphosphino-2',4',6'-tri-isopropyl-1,1'-biphenyl)[2-(2-aminoethyl)phenyl] palladium(II) methyl-tert-butylether adduct (85 g), X-Phos (50 mg) and powdered potassium phosphate (1.32 g). The flask was degassed twice and backfilled with argon. The mixture was heated to reflux for 16 h. Aminophase-silica-gel chromatography of the crude mixture gave 600 mg of the title compound, which contained a small amount of Int08.071. The crude product was used for the next step without further purification.

Intermediate Example Int08.071

(4-{[6-(4-aminophenyl)[1,2,4]triazolo[1,5-a]pyridin-2-yl]amino}-3-methoxy-phenyl)(azetidin-1-yl)methanone

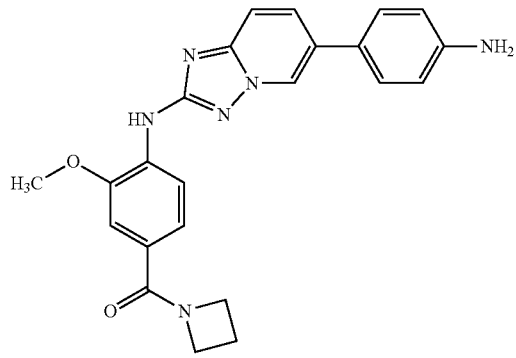 [SMILES: COc1cc(C(=O)N2CCC2)ccc1Nc1nc2ccc(-c3ccc(N)cc3)cn2n1]

To a stirred suspension of Int08.070 (600 mg) in dichloromethane (12 mL) was added TFA (2.2 mL). The mixture was stirred at room temperature for 16 h. A saturated solution of potassium carbonate was added until pH 9 was reached. The mixture was extracted with dichloromethane and methanol (10:1 mixture). The reaction mixture was filtered through an aminophase-silica-gel column and the solvent was removed in vacuum. The residue was triturated with ethanol to give 475 mg of the title compound.

$^1$H-NMR (300 MHz, DMSO-d$_6$): δ [ppm]=2.23 (quin, 2H), 3.88 (s, 3H), 4.00 (br. s., 2H), 4.33 (br. s., 2H), 5.30 (s, 2H), 6.62 (d, 2H), 7.18-7.28 (m, 2H), 7.42 (d, 2H), 7.57 (d, 1H), 7.81 (dd, 1H), 8.23 (s, 1H), 8.32 (d, 1H), 8.90 (d, 1H).

Intermediate Example Int08.080 tert-butyl [4-(2-{[2-methoxy-4-(2-oxo-1,3-oxazolidin-3-yl)phenyl]amino}-[1,2,4]triazolo[1,5-a]pyridin-6-yl)phenyl]carbamate

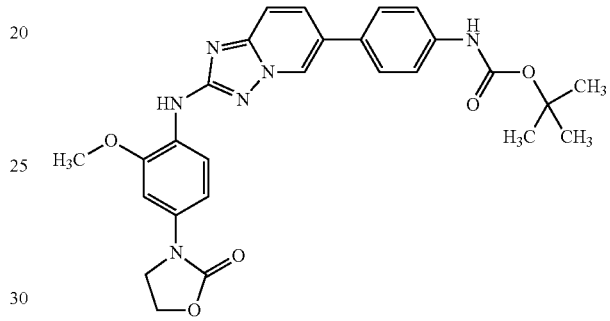

To a stirred suspension of Int01.03 (4.0 g) in toluene (80 mL) and NMP (8 mL) was added Int07.01 (4.4 g), chloro(2-dicyclohexylphosphino-2',4',6'-triisopropyl-1,1'-biphenyl) [2-(2-aminoethyl)phenyl] palladium(II) methyl-tert-butylether adduct (1.02 g), X-Phos (586 mg) and powdered potassium phosphate (9.13 g). The flask was degassed twice and backfilled with argon. The mixture was heated to reflux for 16 h. Aminophase-silica-gel chromatography of the crude mixture gave 2.0 g of the title compound.

$^1$H-NMR (400 MHz, DMSO-d$_6$): δ [ppm]=1.46 (s, 9H), 3.84 (s, 3H), 4.04 (dd, 2H), 4.34-4.47 (m, 2H), 6.98 (dd, 1H), 7.39 (d, 1H), 7.50-7.60 (m, 3H), 7.61-7.70 (m, 2H), 7.80-7.89 (m, 1H), 7.96 (s, 1H), 8.14 (d, 1H), 9.01 (dd, 1H), 9.44 (s, 1H).

Intermediate Example Int08.081

3-(4-{[6-(4-aminophenyl)[1,2,4]triazolo[1,5-a]pyridin-2-yl]amino}-3-methoxyphenyl)-1,3-oxazolidin-2-one

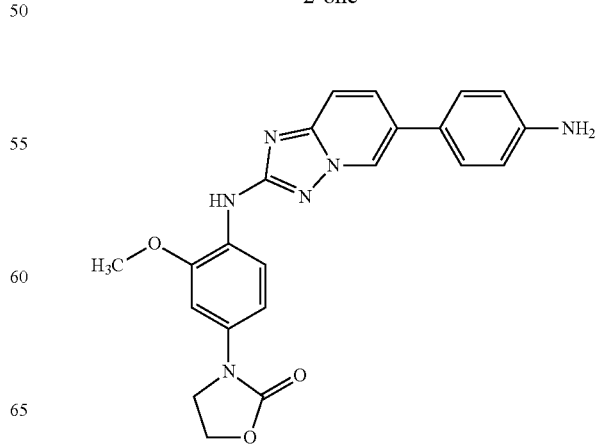

To a stirred suspension of Int08.080 (2.0 g) in DCM (10 mL) was added TFA (6.3 mL). The mixture was stirred at room temperature for 16 h. Further dichloromethane (10 mL) and TFA (6.3 mL) were added, and the mixture was stirred at room temperature for 24 h. The solvent was removed in vacuum and the residue was dissolved in ethyl acetate. A saturated solution of sodium bicarbonate was added until pH 9 was reached. The precipitated solid was collected by filtration to give 1.44 g of the title compound.

$^1$H-NMR (300 MHz, DMSO-d$_6$): δ [ppm]=3.84 (s, 3H), 3.99-4.09 (m, 2H), 4.34-4.46 (m, 2H), 5.25 (s, 2H), 6.63 (d, 2H), 6.97 (dd, 1H), 7.34-7.45 (m, 3H), 7.51 (dd, 1H), 7.77 (dd, 1H), 7.88 (s, 1H), 8.15 (d, 1H), 8.84 (d, 1H).

Intermediate Example Int08.090 tert-butyl [4-(2-{[4-(dimethylcarbamoyl)-2-methoxyphenyl]amino}[1,2,4]triazolo[1,5-a]pyridin-6-yl)phenyl]carbamate

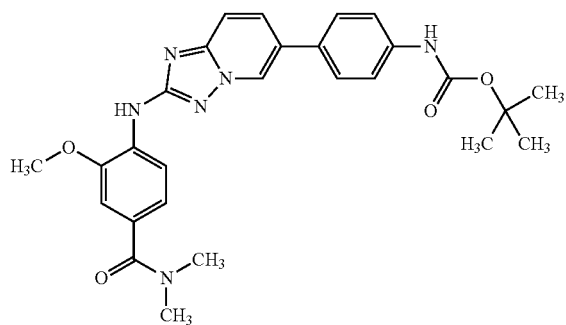 [SMILES: COc1cc(C(=O)N(C)C)ccc1Nc1nc2ccc(-c3ccc(NC(=O)OC(C)(C)C)cc3)cn2n1]

To a stirred suspension of Int01.03 (500 mg) in toluene (12 mL) and NMP (0.6 mL) was added Int02.06 (491 mg), chloro(2-dicyclohexylphosphino-2',4',6'-triisopropyl-1,1'-biphenyl)[2-(2-aminoethyl)phenyl] palladium(II) methyl-tert-butylether adduct (64 mg), X-Phos (37 mg) and powdered potassium phosphate (0.98 g). The flask was degassed twice and backfilled with argon. The mixture was heated to reflux for 16 h. The solvent was removed in vacuum. Aminophase-silica-gel chromatography gave a solid that was triturated with ether to give 650 mg of the title compound.

Intermediate Example Int08.091

4-{[6-(4-aminophenyl)[1,2,4]triazolo[1,5-a]pyridin-2-yl]amino}-3-methoxy-N,N-dimethylbenzamide

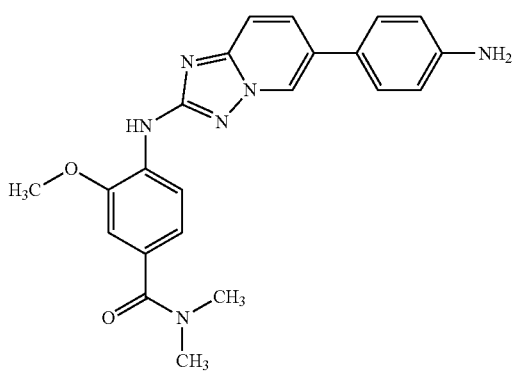 [SMILES: COc1cc(C(=O)N(C)C)ccc1Nc1nc2ccc(-c3ccc(N)cc3)cn2n1]

Starting with Int08.090, Int08.091 was prepared analogously to the procedure for the preparation of Int08.071.

Intermediate Example Int08.100 tert-butyl [4-(2-{[2-methoxy-4-(pyrrolidin-1-ylcarbonyl)phenyl]amino}[1,2,4]triazolo[1,5-a]pyridin-6-yl)phenyl]carbamate

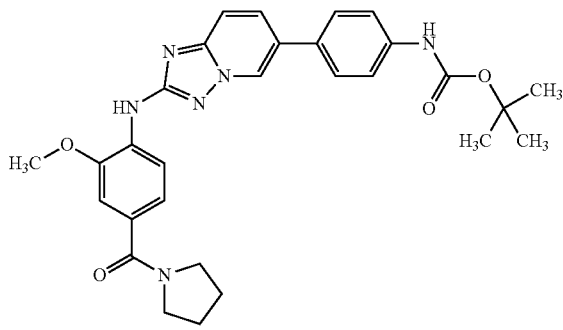 [SMILES: COc1cc(C(=O)N2CCCC2)ccc1Nc1nc2ccc(-c3ccc(NC(=O)OC(C)(C)C)cc3)cn2n1]

Starting with Int01.03 and Int02.07, Int08.100 was prepared analogously to the procedure for the preparation of Int08.090.

Intermediate Example Int08.101

(4-{[6-(4-aminophenyl)[1,2,4]triazolo[1,5-a]pyridin-2-yl]amino}-3-methoxyphenyl)(pyrrolidin-1-yl)methanone

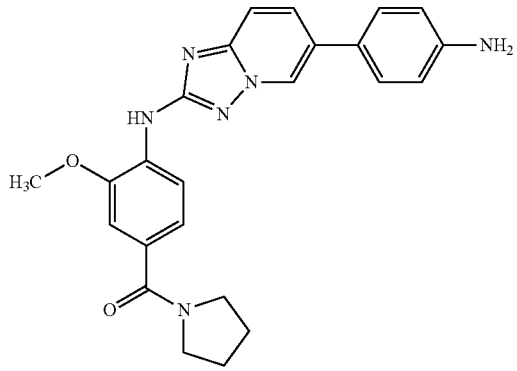 [SMILES: COc1cc(C(=O)N2CCCC2)ccc1Nc1nc2ccc(-c3ccc(N)cc3)cn2n1]

Starting with Int08.100, Int08.101 was prepared analogously to the procedure for the preparation of Int08.071.

Intermediate Example Int08.110 tert-butyl {4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}carbamate

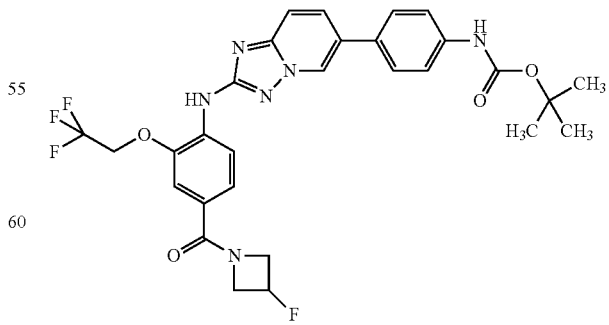

Starting with Int01.03 and Int06.04, Int08.110 was prepared analogously to the procedure for the preparation of Int08.090.

Intermediate Example Int08.111

[4-{[6-(4-aminophenyl)[1,2,4]triazolo[1,5-a]pyridin-2-yl]amino}-3-(2,2,2-trifluoroethoxy)phenyl]3-fluoroazetidin-1-yl)methanone

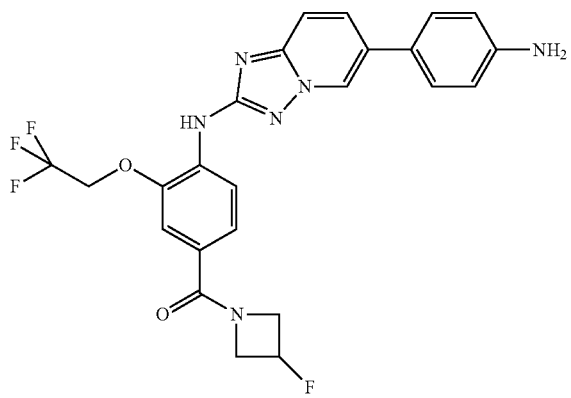 [SMILES: Nc1ccc(-c2ccc3nc(Nc4ccc(C(=O)N5CC(F)C5)cc4OCC(F)(F)F)nn3c2)cc1]

Starting with Int08.110, Int08.111 was prepared analogously to the procedure for the preparation of Int08.071.

Intermediate Example Int08.120 tert-butyl {4-[2-({4-[(3-hydroxyazetidin-1-yl)carbonyl]-2-(2,2,2-trifluoroethoxy)phenyl}amino)[1,2,4]triazolo[1,5-a]pyridin-6-yl]phenyl}carbamate

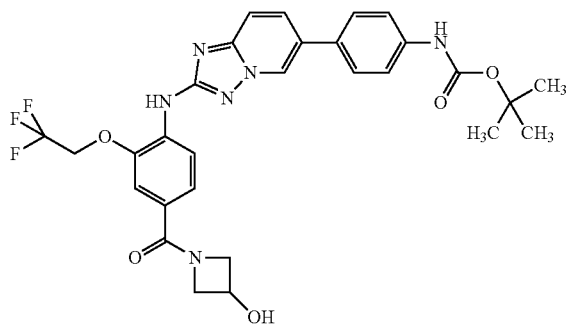 [SMILES: CC(C)(C)OC(=O)Nc1ccc(-c2ccc3nc(Nc4ccc(C(=O)N5CC(O)C5)cc4OCC(F)(F)F)nn3c2)cc1]

Starting with Int01.03 and Int06.05, Int08.120 was prepared analogously to the procedure for the preparation of Int08.090.

Intermediate Example Int08.121

[4-{[6-(4-aminophenyl)[1,2,4]triazolo[1,5-a]pyridin-2-yl]amino}-3-(2,2,2-trifluoroethoxy)phenyl]3-hydroxyazetidin-1-yl)methanone

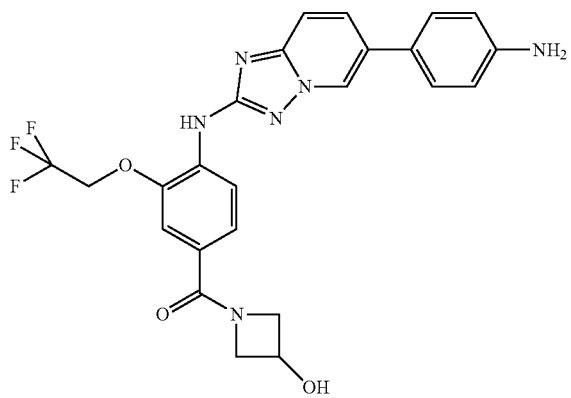

Starting with Int08.120, Int08.121 was prepared analogously to the procedure for the preparation of Int08.071.

Intermediate Example Int08.130 tert-butyl [4-(2-{[4-(pyrrolidin-1-ylcarbonyl)-2-(2,2,2-trifluoroethoxy)phenyl]amino}[1,2,4]triazolo[1,5-a]pyridin-6-yl)phenyl]carbamate

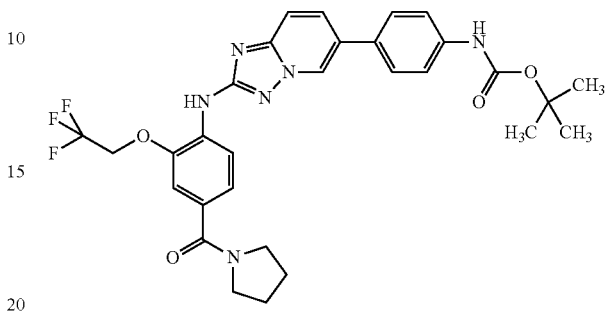

Starting with Int01.03 and Int06.06, Int08.130 was prepared analogously to the procedure for the preparation of Int08.090.

Intermediate Example Int08.131

[4-{[6-(4-aminophenyl)[1,2,4]triazolo[1,5-a]pyridin-2-yl]amino}-3-(2,2,2-trifluoroethoxy)phenyl](pyrrolidin-1-yl)methanone

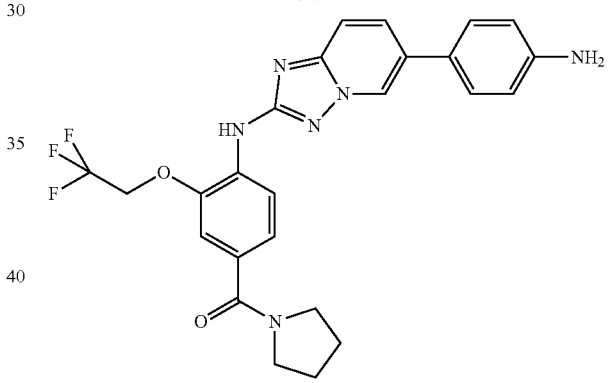

Starting with Int08.130, Int08.131 was prepared analogously to the procedure for the preparation of Int08.071.

Intermediate Example Int08.140 methyl 2-(4-fluorophenyl)-3-hydroxypropanoate

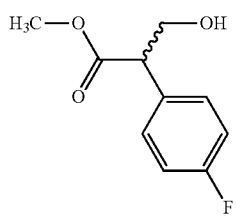

To a stirred solution of methyl (4-fluorophenyl)acetate (5.5 g) in DMSO (220 mL) was added 1,3,5-trioxane (3.24 g) and sodium methoxide (88 mg). The mixture was stirred at room temperature for 16 h. Water was added and the reaction mixture was extracted with ethyl acetate. The organic phase was washed with saturated sodium chloride solution, dried (sodium sulfate) and the solvent was removed in vacuum. Silicagel chromatography gave 3.8 g of the title compound.

¹H-NMR (400 MHz, DMSO-d₆): δ [ppm]=3.50-3.61 (m, 4H), 3.71-3.79 (m, 1H), 3.82-3.90 (m, 1H), 4.98 (t, 1H), 7.07-7.16 (m, 2H), 7.27-7.34 (m, 2H).

Intermediate Example Int08.141 methyl 3-{[tert-butyl(diphenyl)silyl]oxy}-2-(4-fluorophenyl)propanoate

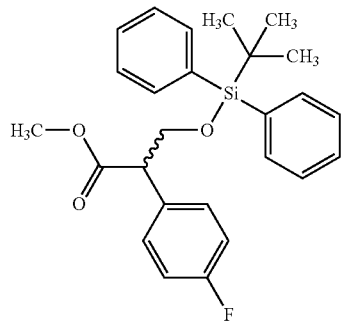 [SMILES: COC(=O)C(CO[Si](c1ccccc1)(c1ccccc1)C(C)(C)C)c1ccc(F)cc1]

To a stirred solution of imidazole (2.36 g) and tert-butyl (chloro)diphenylsilane (4.58 g) in DMF (90 mL) was added a solution of Int08.140 (2.75 g), dissolved in DMF (20 mL). The mixture was stirred at room temperature for 30 minutes. Water was added and the reaction mixture was extracted with ethyl acetate. The organic phase was washed with saturated sodium chloride solution, dried (sodium sulfate) and the solvent was removed in vacuum. Silicagel chromatography gave 5.3 g of the title compound.

¹H-NMR (300 MHz, DMSO-d₆): δ [ppm]=0.90 (s, 9H), 3.60 (s, 3H), 3.77 (dd, 1H), 3.92-4.00 (m, 1H), 4.02-4.11 (m, 1H), 7.05-7.16 (m, 2H), 7.24-7.33 (m, 2H), 7.33-7.46 (m, 6H), 7.46-7.57 (m, 4H).

Intermediate Example Int08.142

3-{[tert-butyl(diphenyl)silyl]oxy}-2-(4-fluorophenyl)propanoic acid

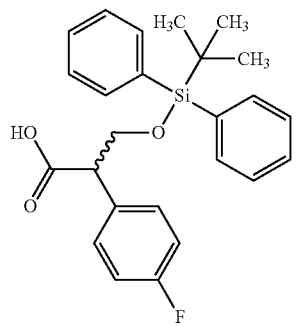 [SMILES: CC(C)(C)[Si](OCC(C(=O)O)c1ccc(F)cc1)(c1ccccc1)c1ccccc1]

To a stirred solution of Int08.141 (5.3 g) in 2-propanol (55 mL) was added a solution of sodium hydroxide (0.97 g), dissolved in water (18 mL). The mixture was stirred at 60° C. for 30 minutes. The solution was cooled to room temperature, saturated ammonium chloride solution was added and the reaction mixture was extracted with ethyl acetate. The organic phase was dried (sodium sulfate) and the solvent was removed in vacuum. Silicagel chromatography gave 5.3 g of the title compound.

¹H-NMR (300 MHz, DMSO-d₆): δ [ppm]=0.90 (s, 9H), 3.67-3.76 (m, 1H), 3.77-3.87 (m, 1H), 4.02-4.10 (m, 1H), 7.05-7.15 (m, 2H), 7.24-7.32 (m, 2H), 7.32-7.46 (m, 6H), 7.46-7.59 (m, 4H), 12.64 (br. s., 1H).

Intermediate Example Int08.143

3-{[tert-butyl(diphenyl)silyl]oxy}-2-(4-fluorophenyl)-N-[4-(2-{[4-(methylsulfonyl)-2-(2,2,2-trifluoroethoxy)phenyl]amino}[1,2,4]triazolo[1,5-a]pyridin-6-yl)phenyl]propanamide

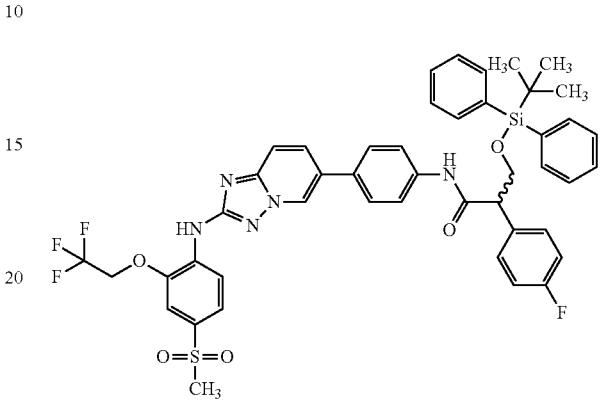

To a stirred solution of Int08.021 (400 mg) in DMF (10 mL) was added potassium carbonate (347 mg), Int08.142 (425 mg) and HATU (478 mg). The mixture was stirred at room temperature for 16 h. Water was added, the mixture was stirred for 15 minutes and the mixture was extracted with ethyl acetate. The organic phase was washed with saturated sodium chloride solution, dried (sodium sulfate) and the solvent was removed in vacuum. Aminophase-silica-gel chromatography gave 346 mg of the title compound.

¹H-NMR (400 MHz, DMSO-d₆): δ [ppm]=0.91 (s, 9H), 3.17 (s, 3H), 3.74 (dd, 1H), 4.07 (dd, 1H), 4.21-4.32 (m, 1H), 5.00 (q, 2H), 7.08-7.17 (m, 2H), 7.32-7.47 (m, 8H), 7.50-7.56 (m, 2H), 7.58-7.66 (m, 4H), 7.66-7.78 (m, 5H), 7.95 (dd, 1H), 8.51 (d, 1H), 8.57 (s, 1H), 9.13 (d, 1H), 10.38 (s, 1H).

Intermediate Example Int08.144

3-{[tert-butyl(diphenyl)silyl]oxy}-2-(4-fluorophenyl)-N-[4-(2-{[2-methoxy-4-(methylsulfonyl)phenyl]amino}[1,2,4]triazolo[1,5-a]pyridin-6-yl)phenyl]propanamide

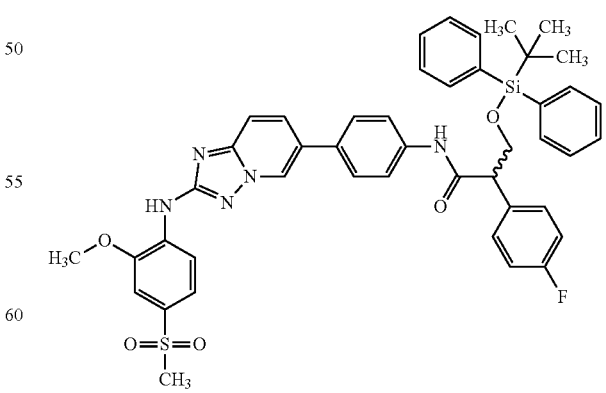

Starting with Int08.011 and Int08.142, Int08.144 was prepared analogously to the procedure for the preparation of Int08.143.

Intermediate Example Int08.145

3-{[tert-butyl(diphenyl)silyl]oxy}-N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)propanamide

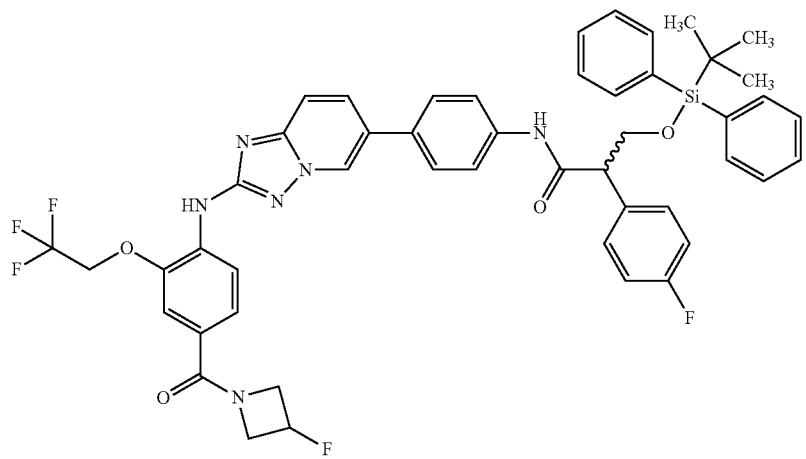 [SMILES: CC(C)(C)[Si](OCC(C(=O)Nc1ccc(-c2ccc3nc(Nc4ccc(C(=O)N5CC(F)C5)cc4OCC(F)(F)F)nn3c2)cc1)c1ccc(F)cc1)(c1ccccc1)c1ccccc1]

Starting with Int08.111 and Int08.142, Int08.145 was prepared analogously to the procedure for the preparation of Int08.143.

Intermediate Example Int08.146

(2S)-3-{[tert-butyl(diphenyl)silyl]oxy}-N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)propanamide

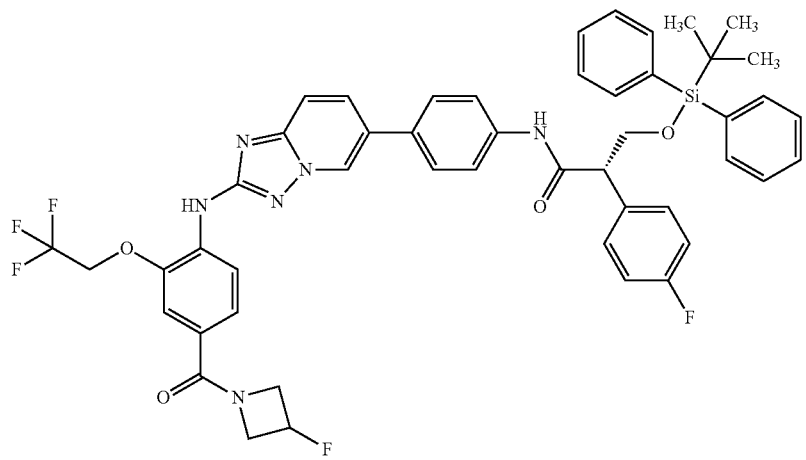 [SMILES: CC(C)(C)[Si](OC[C@@H](C(=O)Nc1ccc(-c2ccc3nc(Nc4ccc(C(=O)N5CC(F)C5)cc4OCC(F)(F)F)nn3c2)cc1)c1ccc(F)cc1)(c1ccccc1)c1ccccc1]

The enantiomers of 730 mg of Int08.145 were separated using chiral HPLC. Column: Chiralpak IA 5µ 250×30 mm; Flow: 50.0 mL/min; Solvent: A: Hexane, B: Ethanol; C: Formic acid; Solvent mixture: A:B:C=70:30:0.1. Retention time of the title compound: 20.4-25.2 min (Peak 2). Yield: 295 mg.

Column: Chiralpak IA 5µ 150×4.6; Flow: 1.00 mL/min; Solvent: A: Hexane, B: Ethanol; C: Formic acid; Solvent mixture: A:B:C=70:30:0.1. Run Time: 40 min. Retention Time: 32.59 min; UV 254 nm; Enantiomeric Ratio: 2.1%: 97.9%.

Intermediate Example Int08.150 tert-butyl [(1R)-1-(4-fluorophenyl)-2-{[4-(2-{[2-methoxy-4-(methylsulfonyl)-phenyl]amino}[1,2,4]triazolo[1,5-a]pyridin-6-yl)phenyl]amino}-2-oxoethyl]carbamate

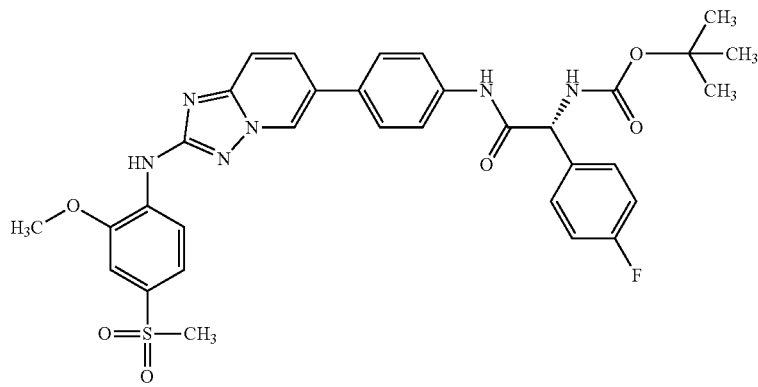 [SMILES: COc1cc(S(C)(=O)=O)ccc1Nc1nc2ccc(-c3ccc(NC(=O)[C@H](NC(=O)OC(C)(C)C)c4ccc(F)cc4)cc3)cn2n1]

To a stirred suspension of Int08.011 (200 mg) in DMF (1.6 mL) and dichloromethane (3.2 mL) was added sodium bicarbonate (82 mg), (2R)-[(tert-butoxycarbonyl)amino](4-fluorophenyl)acetic acid (166 mg) and HATU (279 mg). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave 300 mg of the title compound.

$^1$H-NMR (300 MHz, DMSO-$d_6$): δ [ppm]=1.36 (s, 9H), 3.16 (s, 3H), 3.95 (s, 3H), 5.34 (d, 1H), 7.17 (t, 2H), 7.42 (d, 1H), 7.47-7.55 (m, 3H), 7.58-7.78 (m, 6H), 7.92 (dd, 1H), 8.48 (d, 1H), 8.64 (s, 1H), 9.12 (d, 1H), 10.38 (s, 1H).

Intermediate Example Int08.151 tert-butyl [(1R)-1-(4-fluorophenyl)-2-{[4-(2-{[4-(methylsulfonyl)-2-(2,2,2-trifluoroethoxy)phenyl]amino}[1,2,4]triazolo[1,5-a]pyridin-6-yl)phenyl]amino}-2-oxoethyl]carbamate

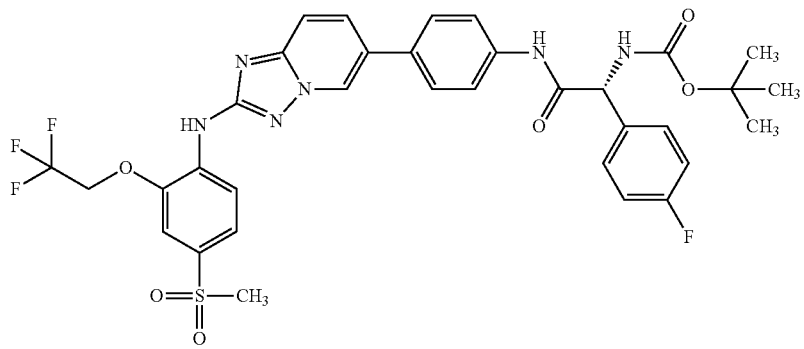 [SMILES: CC(C)(C)OC(=O)N[C@@H](C(=O)Nc1ccc(-c2ccc3nc(Nc4ccc(S(C)(=O)=O)cc4OCC(F)(F)F)nn3c2)cc1)c1ccc(F)cc1]

Starting with Int08.021, Int08.151 was prepared analogously to the procedure for the preparation of Int08.150.

Intermediate Example Int08.152 tert-butyl [(1R)-1-(4-fluorophenyl)-2-{[4-(2-{[2-methoxy-4-(2-oxo-1,3-oxazolidin-3-yl)phenyl]amino}[1,2,4]triazolo[1,5-a]pyridin-6-yl)phenyl]amino}-2-oxoethyl]carbamate

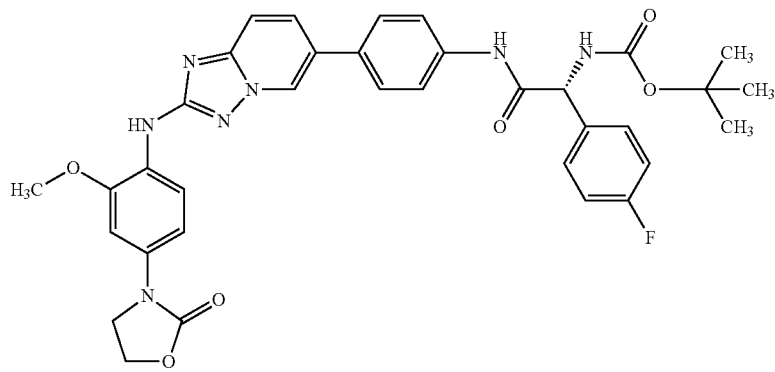 [SMILES: COc1cc(N2CCOC2=O)ccc1Nc1nc2ccc(-c3ccc(NC(=O)[C@H](NC(=O)OC(C)(C)C)c4ccc(F)cc4)cc3)cn2n1]

Starting with Int08.081, Int08.152 was prepared analogously to the procedure for the preparation of Int08.150.

Intermediate Example Int08.153 tert-butyl [(1R)-2-({4-[2-({4-[(3-fluoroazetidin-1-yl)carbonyl]-2-methoxyphenyl}amino)[1,2,4]triazolo[1,5-a]pyridin-6-yl]phenyl}amino)-1-(4-fluorophenyl)-2-oxoethyl]carbamate

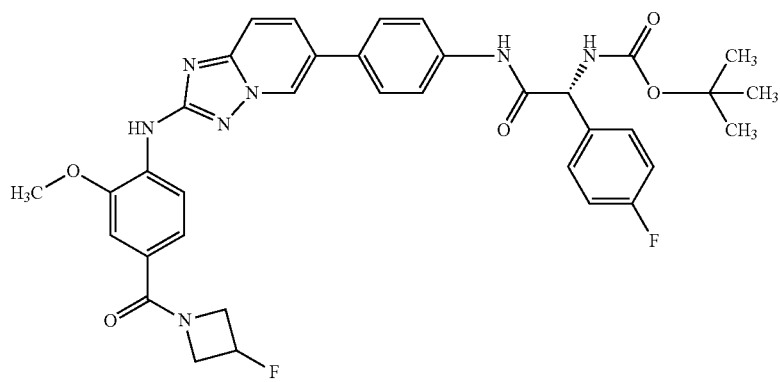 [SMILES: COc1cc(C(=O)N2CC(F)C2)ccc1Nc1nc2ccc(-c3ccc(NC(=O)[C@H](NC(=O)OC(C)(C)C)c4ccc(F)cc4)cc3)cn2n1]

Starting with Int08.061, Int08.153 was prepared analogously to the procedure for the preparation of Int08.150.

Intermediate Example Int08.154 tert-butyl [(1R)-2-{[4-(2-{[4-(azetidin-1-ylcarbonyl)-2-methoxyphenyl]amino}[1,2,4]triazolo[1,5-a]pyridin-6-yl)phenyl]amino}-1-(4-fluorophenyl)-2-oxoethyl]carbamate

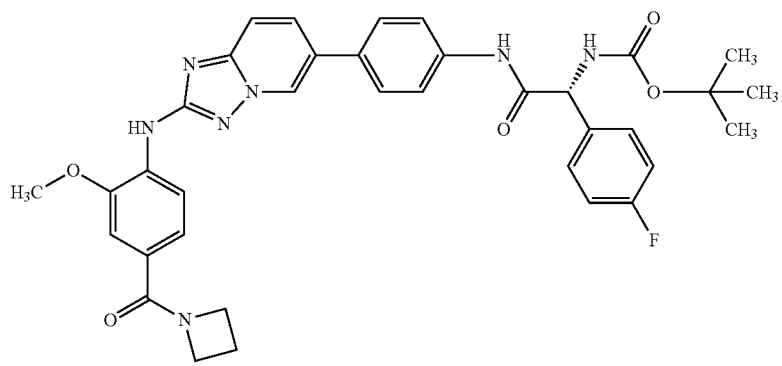 [SMILES: COc1cc(C(=O)N2CCC2)ccc1Nc1nc2ccc(-c3ccc(NC(=O)[C@H](NC(=O)OC(C)(C)C)c4ccc(F)cc4)cc3)cn2n1]

Starting with Int08.071, Int08.154 was prepared analogously to the procedure for the preparation of Int08.150.

Intermediate Example Int08.155 tert-butyl [(1R)-1-(4-fluorophenyl)-2-{[4-(2-{[2-methoxy-4-(pyrrolidin-1-ylcarbonyl)phenyl]amino}[1,2,4]triazolo[1,5-a]pyridin-6-yl)phenyl]amino}-2-oxoethyl]carbamate

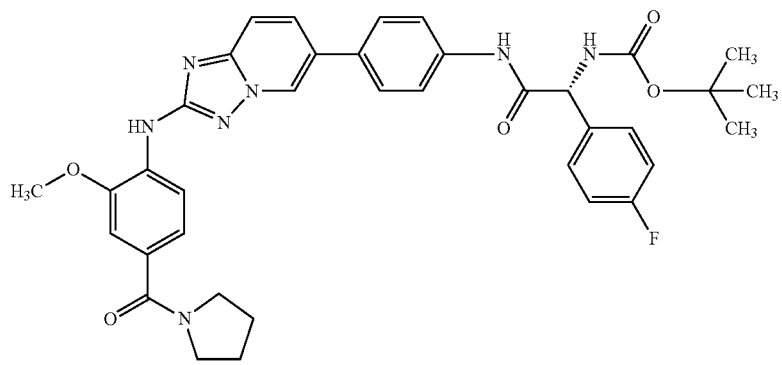 [SMILES: COc1cc(C(=O)N2CCCC2)ccc1Nc1nc2ccc(-c3ccc(NC(=O)[C@H](NC(=O)OC(C)(C)C)c4ccc(F)cc4)cc3)cn2n1]

Starting with Int08.101, Int08.155 was prepared analogously to the procedure for the preparation of Int08.150.

Intermediate Example Int08.156 tert-butyl [(1R)-2-({4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}amino)-1-(4-fluorophenyl)-2-oxoethyl]carbamate

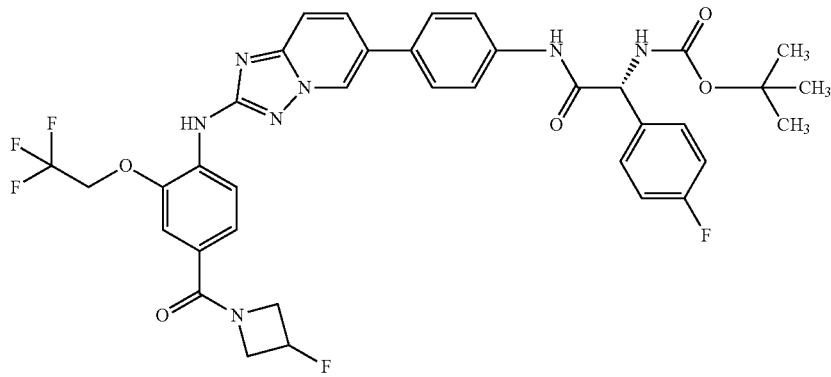 [SMILES: CC(C)(C)OC(=O)N[C@@H](C(=O)Nc1ccc(-c2ccc3nc(Nc4ccc(C(=O)N5CC(F)C5)cc4OCC(F)(F)F)nn3c2)cc1)c1ccc(F)cc1]

Starting with Int08.111, Int08.156 was prepared analogously to the procedure for the preparation of Int08.150.

Intermediate Example Int08.157 tert-butyl [(1R)-1-(4-fluorophenyl)-2-oxo-2-{[4-(2-{[4-(pyrrolidin-1-ylcarbonyl)-2-(2,2,2-trifluoroethoxy)phenyl]amino}[1,2,4]triazolo[1,5-a]pyridin-6-yl)phenyl]amino}ethyl]carbamate

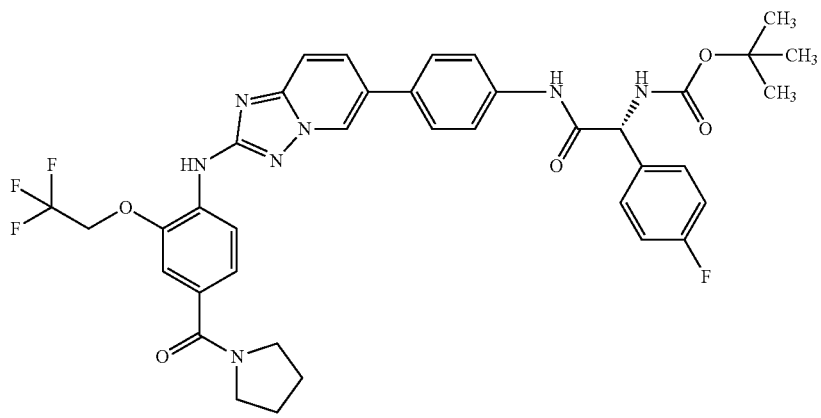 [SMILES: CC(C)(C)OC(=O)N[C@@H](C(=O)Nc1ccc(-c2ccc3nc(Nc4ccc(C(=O)N5CCCC5)cc4OCC(F)(F)F)nn3c2)cc1)c1ccc(F)cc1]

Starting with Int08.131, Int08.157 was prepared analogously to the procedure for the preparation of Int08.150.

Intermediate Example Int09.01

Rac-methyl 2-(4-fluorophenyl)propanoate

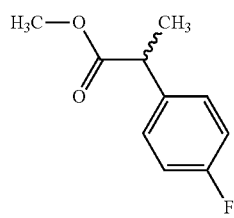

To a stirred solution of diisopropylamine (13.0 g) in tetrahydrofurane (160 mL) was added a solution of n-butyllithium in hexane (51.4 mL; c=2.5 M) at −78° C. The solution was stirred at 0° C. for 15 minutes. The solution was cooled to −78° C. and a solution of methyl (4-fluorophenyl)acetate (18.0 g), dissolved in tetrahydrofurane (40 mL) was added. The solution was stirred at −78° C. for 30 minutes. Methyl iodide (10.0 mL) was added at −78° C., and the solution was allowed to warm up to 0° C. within 1 h. Water was added and the reaction mixture was extracted with ethyl acetate. The organic phase was dried (sodium sulfate) and the solvent was removed in vacuum. Silicagel chromatography gave 18.9 g of the title compound.

$^1$H-NMR (400 MHz, DMSO-d$_6$): δ [ppm]=1.34 (d, 3H), 3.55 (s, 3H), 3.79 (q, 1H), 7.08-7.15 (m, 2H), 7.25-7.32 (m, 2H).

Intermediate Example Int09.02

Rac-2-(4-fluorophenyl)propanoic acid

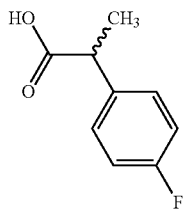

To a stirred solution of Int09.01 (18.9 g) in ethanol (200 mL) was added a solution of potassium hydroxide (35 g), dissolved in water (200 mL). The mixture was stirred at 0° C. for 4 h. Hydrochloric acid (c=4.0 M) was added until pH 5 was reached and the reaction mixture was extracted with ethyl acetate. The organic phase was separated and the solvent was removed in vacuum to give 15.64 g of the title product. The crude product was used without further purification.

$^1$H-NMR (300 MHz, DMSO-$d_6$): δ [ppm]=1.31 (d, 3H), 3.66 (q, 1H), 7.05-7.15 (m, 2H), 7.24-7.33 (m, 2H), 12.30 (s, 1H).

Intermediate Example Int09.03

(2R)-2-(4-fluorophenyl)propanoic acid

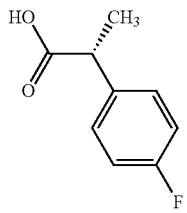

To a stirred solution of Int09.02 (23.6 g) in refluxing ethyl acetate (250 mL) was added a solution of (1S)-1-phenylethanamine (17.35 g) in ethyl acetate. The mixture was allowed to cool down to room temperature within 1 h. A white solid was collected by filtration, was washed with ethyl acetate and dried in vacuum to give 27.5 g of a solid. The solid was recrystallized from 400 mL refluxing ethyl acetate. The mixture was allowed to cool down to room temperature. A white solid was collected by filtration, was washed with ethyl acetate and dried in vacuum to give 18.3 g of a solid. The solid was twice recrystallized from refluxing ethyl acetate (350 mL; 300 mL). A white solid was collected by filtration, was washed with ethyl acetate and dried in vacuum to give 10.51 g of a solid. The solid was dissolved in water, hydrochloric acid (c=2.0 M) was added until pH 5 was reached and the reaction mixture was extracted with dichloromethane. The organic phase was dried (sodium sulfate) and the solvent was removed in vacuum to give 5.6 g of the title product. The crude product was used without further purification.

$^1$H-NMR (300 MHz, DMSO-$d_6$): δ [ppm]=1.31 (d, 3H), 3.66 (q, 1H), 7.05-7.16 (m, 2H), 7.24-7.33 (m, 2H), 12.28 (br. s., 1H).

$[α]_D^{20}$: −79.3° (in DMSO)

Column: Chiralcel OJ-H 150×4.6; Flow: 1.00 mL/min; Solvent: A: Hexane, B: 2-propanol with 0.1% formic acid; Solvent mixture: 80% A+20% B. Run Time: 30 min. Retention Time: 3.41 min; UV 254 nm; Enantiomeric Ratio: 99.8%:0.2%.

Intermediate Example Int10.01

1-bromo-2-(cyclopropyloxy)-4-fluorobenzene

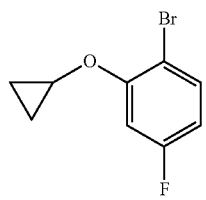 [SMILES: Fc1ccc(Br)c(OC2CC2)c1]

To a stirred solution of 2-bromo-5-fluorophenol (1.0 g) in DMF (15 mL) in a microwave tube was added cesium carbonate (5.0 g), potassium iodide (130 mg) and bromocyclopropane (1.82 g). The mixture was heated in a microwave oven to 180° C. for 1 h, to 200° C. for 1 h and to 220° C. for 1 h. Ethyl acetate was added and the mixture was washed with water. The organic phase was washed with saturated sodium chloride solution, dried (sodium sulfate) and the solvent was removed in vacuum. Silica gel chromatography gave 1.14 g of the title compound.

$^1$H-NMR (300 MHz, DMSO-$d_6$): δ [ppm]=0.62-0.88 (m, 4H), 3.90-4.00 (m, 1H), 6.77 (td, 1H), 7.23 (dd, 1H), 7.48-7.63 (m, 1H).

Intermediate Example Int10.02

1-bromo-2-(cyclopropyloxy)-4-(methylsulfanyl)benzene

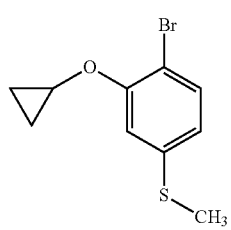

To a stirred solution of Int10.01 (1.4 g) in DMF (12 mL) was added sodium methanethiolate (546 mg). The mixture was for 2 h at 90° C. The mixture was cooled to room temperature, water was added and the mixture was extracted with ethyl acetate. The organic phase was washed with saturated sodium chloride solution, dried (sodium sulfate) and the solvent was removed in vacuum. Silica gel chromatography gave 1.17 g of the title compound.

$^1$H-NMR (300 MHz, DMSO-$d_6$): δ [ppm]=0.59-0.85 (m, 4H), 2.46 (s, 3H), 3.95 (tt, 1H), 6.77 (dd, 1H), 7.18 (d, 1H), 7.43 (d, 1H).

Intermediate Example Int1 0.03

1-bromo-2-(cyclopropyloxy)-4-(methylsulfonyl)benzene

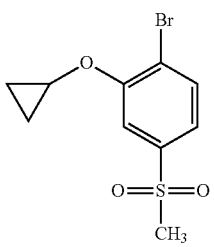

To a stirred solution of Int10.02 (1.15 g) in chloroform (45 mL) was added 3-chlorobenzenecarboperoxoic acid (mCPBA) (2.98 g). The mixture was stirred at room temperature for 2 h. With ice bath cooling, a half-saturated solution of sodium bicarbonate and a 0.2 M solution of sodium thiosulfate was added, the mixture was stirred for 30 minutes and the mixture was extracted with dichloromethane. The organic phase was washed with saturated sodium chloride solution, dried (sodium sulfate) and the solvent was removed in vacuum. Silica gel chromatography gave 0.91 g of the title compound.

$^1$H-NMR (300 MHz, DMSO-$d_6$): δ [ppm]=0.66-0.93 (m, 4H), 3.23 (s, 3H), 4.09 (tt, 1H), 7.43 (dd, 1H), 7.77 (d, 1H), 7.84 (d, 1H).

Intermediate Example Int21.01

Ethyl [(5-chloropyridin-2-yl)carbamothioyl]carbamate

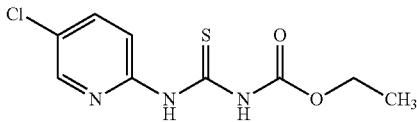 [SMILES: CCOC(=O)NC(=S)Nc1ccc(Cl)cn1]

Ethoxycarbonylisothiocyanate (3.37 g) was added to a stirred solution of 2-amino-5-chloropyridine (3.0 g) in dioxane (100 mL). The mixture was stirred at r.t. for 14 h. The solvent was removed in vacuum. The solid was dissolved in dichloromethane and methanol (100:1), filtered and the solvent was removed in vacuum to give a solid that was recrystallized from ethyl acetate to give 4.4 g of the title compound.

$^1$H-NMR (400 MHz, CHLOROFORM-d): δ [ppm]=1.35 (3H), 4.31 (2H), 7.71 (1H), 8.03 (1H), 8.34 (1H), 8.83 (1H), 12.09 (1H).

Intermediate Example Int21.02

6-chloro[1,2,4]triazolo[1,5-a]pyridin-2-amine

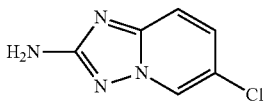 [SMILES: Nc1nc2ccc(Cl)cn2n1]

Hydroxylammonium chloride (4.4 g) was suspended in methanol (35 mL) and ethanol (35 mL) and Hünig Base (10.2 mL) was added at r.t. The mixture was heated to 60° C., Int21.01 (4.4 g) was added portionwise, and the mixture was stirred at 60° C. for 2 h. The solvent was removed in vacuum and water (150 mL) was added. A solid was collected by filtration and was washed with water and dried in vacuum.

Yield: 2.0 g of the title compound.

$^1$H-NMR (300 MHz, DMSO-$d_6$): δ [ppm]=6.09 (2H), 7.28-7.37 (1H), 7.39-7.49 (1H), 8.84 (1H).

Intermediate Example Int21.03

6-chloro-N-[2-methoxy-4-(methylsulfonyl)phenyl][1,2,4]triazolo[1,5-a]pyridin-2-amine

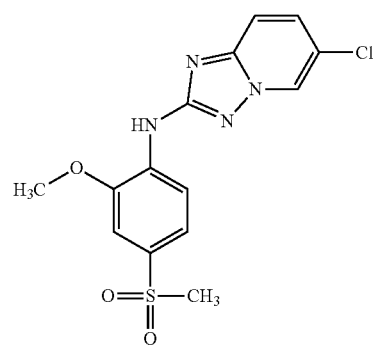 [SMILES: COc1cc(S(C)(=O)=O)ccc1Nc1nc2ccc(Cl)cn2n1]

To a stirred suspension of Int21.02 (0.7 g) in toluene (28 mL) was added Int03.02 (1.27 g), chloro(2-dicyclohexylphosphino-2',4',6'-tri-isopropyl-1,1'-biphenyl)[2-(2-aminoethyl)phenyl] palladium(II) methyl-tert-butylether adduct (343 mg), X-Phos (202 mg) and powdered potassium phosphate (3.09 g). The flask was degassed twice and backfilled with argon. The mixture was heated to reflux for 3 h. Further chloro(2-dicyclohexylphosphino-2',4',6'-tri-isopropyl-1,1'-biphenyl)[2-(2-aminoethyl)phenyl] palladium(II) methyl-tert-butylether adduct (30 mg) and X-Phos (19 mg) were added and the mixture was heated to reflux for 15 h. The solvent was removed in vacuum. Silicagel chromatography gave a solid that was triturated ethyl acetate to give 1.0 g of the title compound.

$^1$H-NMR (400 MHz, DMSO-$d_6$): δ [ppm]=3.16 (3H), 3.95 (3H), 7.42 (1H), 7.50 (1H), 7.62-7.69 (2H), 8.41 (1H), 8.70 (1H), 9.17 (1H).

Intermediate Example Int21.04

4-(2-{[2-methoxy-4-(methylsulfonyl)phenyl]amino}[1,2,4]triazolo[1,5-a]pyridin-6-yl)benzoic acid

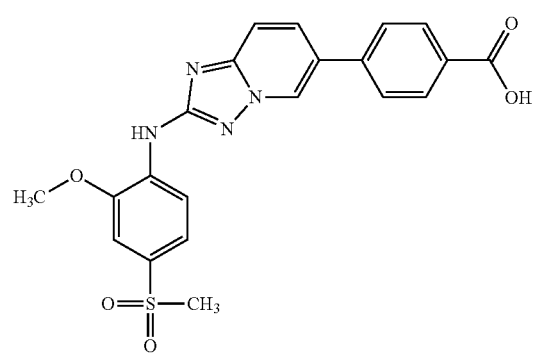 [SMILES: COc1cc(S(C)(=O)=O)ccc1Nc1nc2ccc(-c3ccc(C(=O)O)cc3)cn2n1]

To a stirred solution of Int21.03 (70 mg) in 1-propanol (1.5 mL) was added 2M potassium carbonate solution (0.3 mL), 4-carboxyphenylboronic acid (37 mg), triphenylphosphine (2.6 mg) and $PdCl_2(PPh_3)_2$ (14.0 mg). The mixture was heated to reflux for 1.5 h. Further triphenylphosphine (3.0 mg) and $PdCl_2(PPh_3)_2$ (14.0 mg) were added and the mixture was heated to reflux for 18 h. Again, further triphenylphosphine (3.0 mg) and $PdCl_2(PPh_3)_2$ (14.0 mg) were added and the mixture was heated to reflux for further 24 h. The solvent was removed in vacuum. Silicagel chromatography gave 47 mg of the title compound as crude product, that was used for the next step without further purification.

Intermediate Example Int21.05

2-(4-fluorophenyl)-N-[4-(4,4,5,5-tetramethyl-1,3,2-dioxaborolan-2-yl)phenyl]acetamide

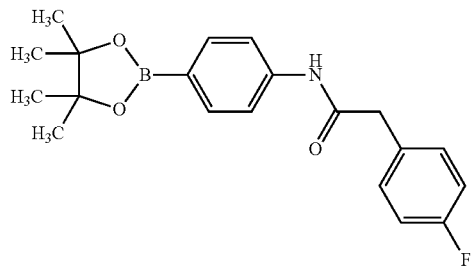 [SMILES: CC1(C)OB(c2ccc(NC(=O)Cc3ccc(F)cc3)cc2)OC1(C)C]

To a stirred solution of 4-(4,4,5,5-tetramethyl-1,3,2-dioxaborolan-2-yl)aniline (200 mg) in DMF (9 mL) and dichloromethane (18 mL) was added sodium bicarbonate (153 mg), (4-fluorophenyl)acetic acid (155 mg) and HATU (521 mg). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave 120 mg of the title compound.
$^1$H-NMR (300 MHz, DMSO-$d_6$), δ [ppm]=1.24 (12H), 3.61 (2H), 7.03-7.17 (2H), 7.26-7.37 (2H), 7.57 (4H), 10.24 (1H).

Intermediate Example Int21.06

(2R)-2-(4-fluorophenyl)-N-[4-(4,4,5,5-tetramethyl-1,3,2-dioxaborolan-2-yl)phenyl]propanamide

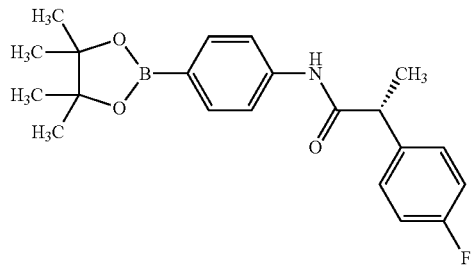 [SMILES: C[C@@H](C(=O)Nc1ccc(B2OC(C)(C)C(C)(C)O2)cc1)c1ccc(F)cc1]

To a stirred solution of 4-(4,4,5,5-tetramethyl-1,3,2-dioxaborolan-2-yl)aniline (1.0 g) in DMF (45 mL) and dichloromethane (90 mL) was added sodium bicarbonate (766 mg), (2R)-2-(4-fluorophenyl)propanoic acid (844 mg) and HATU (2.6 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Silica-gel chromatography gave 1.53 g of the title compound.
$^1$H-NMR (400 MHz, DMSO-$d_6$), δ [ppm]=1.23 (12H), 1.37 (3H), 3.74-3.87 (1H), 7.06-7.16 (2H), 7.31-7.42 (2H), 7.51-7.61 (4H), 10.12 (1H).

Intermediate Example Int21.07

(4-{[(2R)-2-(4-fluorophenyl)propanoyl]amino}phenyl)boronic acid

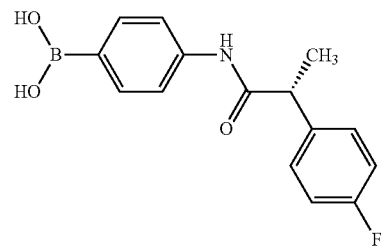 [SMILES: C[C@@H](C(=O)Nc1ccc(B(O)O)cc1)c1ccc(F)cc1]

To a stirred solution of (4-aminophenyl)boronic acid hydrochloride (2.00 g) in DMF (42 mL) was added sodium bicarbonate (2.9 g), (2R)-2-(4-fluorophenyl)propanoic acid (2.04 g) and HATU (6.58 g). The mixture was stirred at room temperature for 72 h. Water (140 mL) was added, and the mixture was stirred for 2 h. The white precipitate was collected by filtration and was washed with water and was dried in vacuum to give 2.86 g of the title compound.
$^1$H-NMR (300 MHz, DMSO-$d_6$), δ [ppm]=1.39 (3H), 3.84 (1H), 7.08-7.21 (2H), 7.35-7.44 (2H), 7.52 (2H), 7.69 (2H), 7.88 (2H), 10.07 (1H).

Intermediate Example Int21.08

6-chloro-N-[4-(methylsulfonyl)-2-(2,2,2-trifluoroethoxy)phenyl][1,2,4]triazolo[1,5-a]pyridin-2-amine

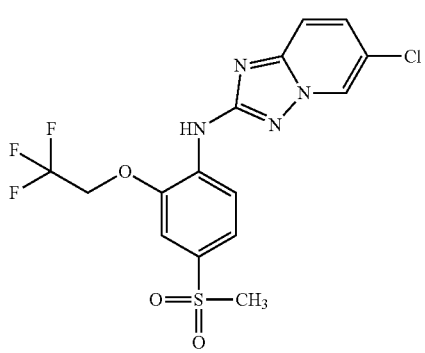 [SMILES: CS(=O)(=O)c1ccc(Nc2nc3ccc(Cl)cn3n2)c(OCC(F)(F)F)c1]

To a stirred suspension of Int21.02 (75 mg) in toluene (3 mL) and NMP (0.19 mL) was added Int05.03 (170 mg), chloro(2-dicyclohexylphosphino-2',4',6'-tri-isopropyl-1,1'- biphenyl)[2-(2-aminoethyl)phenyl] palladium(II) methyl-tert-butylether adduct (11.0 mg), X-Phos (6.49 mg) and powdered potassium phosphate (330 mg). The flask was degassed twice and backfilled with argon. The mixture was heated to reflux for 2 h. The reaction mixture was filtered through an aminophase-silicagel column and the solvent was removed in vacuum to give 96 mg of the title compound.

$^1$H-NMR (300 MHz, DMSO-$d_6$), δ [ppm]=3.19 (3H), 5.01 (2H), 7.59-7.75 (4H), 8.45 (1H), 8.74 (1H), 9.21 (1H).

Intermediate Example Int21.09

{4-[(6-chloro[1,2,4]triazolo[1,5-a]pyridin-2-yl)amino]-3-methoxyphenyl}(3-fluoroazetidin-1-yl)methanone

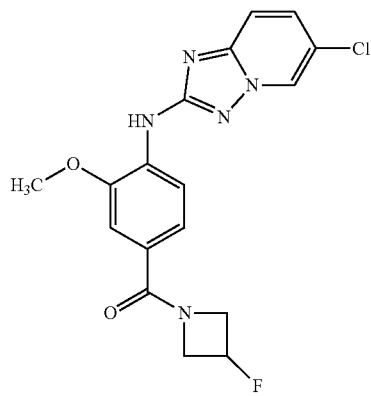 [SMILES: COc1cc(C(=O)N2CC(F)C2)ccc1Nc1nc2ccc(Cl)cn2n1]

To a stirred suspension of Int21.02 (76.3 mg) in toluene (3 mL) and NMP (0.3 mL) was added Int02.05 (150 mg), chloro(2-dicyclohexylphosphino-2',4',6'-tri-isopropyl-1,1'-biphenyl)[2-(2-aminoethyl)phenyl] palladium(II) methyl-tert-butylether adduct (37.4 mg), X-Phos (22.0 mg) and powdered potassium phosphate (336 mg). The flask was degassed twice and backfilled with argon. The mixture was heated to reflux for 2 h. The reaction mixture was filtered through an aminophase-silicagel column and the solvent was removed in vacuum. Silicagel chromatography gave a solid that was triturated with ethanol to give 120 mg of the title compound.

$^1$H-NMR (300 MHz, DMSO-$d_6$), δ [ppm]=3.91 (3H), 3.96-4.78 (4H), 5.28-5.58 (1H), 7.23-7.32 (2H), 7.61-7.72 (2H), 8.29 (1H), 8.47 (1H), 9.15-9.21 (1H).

Intermediate Example Int21.10

4-[(6-chloro[1,2,4]triazolo[1,5-a]pyridin-2-yl)amino]-3-methoxy-N,N-dimethylbenzamide

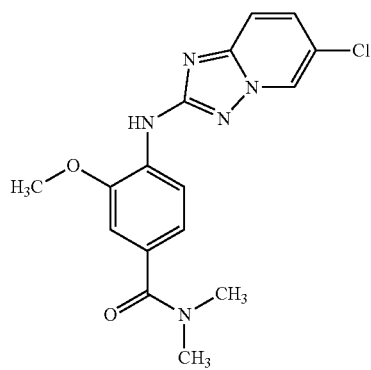 [SMILES: COc1cc(C(=O)N(C)C)ccc1Nc1nc2ccc(Cl)cn2n1]

To a stirred suspension of Int21.02 (82.6 mg) in toluene (3.2 mL) and NMP (0.32 mL) was added Int02.06 (150 mg), chloro(2-dicyclohexylphosphino-2',4',6'-tri-isopropyl-1,1'-biphenyl)[2-(2-aminoethyl)phenyl] palladium(II) methyl-tert-butylether adduct (40.5 mg), X-Phos (23.8 mg) and powdered potassium phosphate (364 mg). The flask was degassed twice and backfilled with argon. The mixture was heated to reflux for 2 h. The reaction mixture was filtered through an aminophase-silicagel column and the solvent was removed in vacuum. Silicagel chromatography gave a solid that was triturated with ethanol to give 150 mg of the title compound.

$^1$H-NMR (400 MHz, DMSO-$d_6$), δ [ppm]=2.97 (6H), 3.89 (3H), 7.00-7.08 (2H), 7.58-7.70 (2H), 8.23 (1H), 8.29 (1H), 9.15 (1H).

Intermediate Example Int21.11

(2-{[2-methoxy-4-(methylsulfonyl)phenyl]amino}[1,2,4]triazolo[1,5-a]pyridin-6-yl)boronic acid

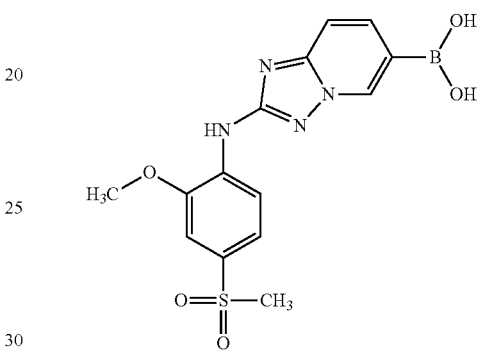

To a stirred suspension of 6-chloro-N-[2-methoxy-4-(methylsulfonyl)phenyl][1,2,4]triazolo[1,5-a]pyridin-2-amine (17.6 g) and bispinacolatodiboron (19.0 g) in toluene (250 g) were added tris(dibenzylideneacetone)dipalladium (0.9 g) and X-Phos (0.95 g). Then potassium acetate (14.7 g) and toluene (10.5 g) were added and the mixture was stirred at reflux for 1 h. The resulting mixture was cooled to 70° C. and 200 ml 1N aqueous sodium hydroxide solution was added followed by stirring for 1.5 h. Then an additional amount of 100 ml 1N aqueous sodium hydroxide solution was added and stirring was continued for 30 min at 40° C. The mixture was filtrated through diatomaceous earth. The diatomaceous earth was washed with toluene (100 g) and water (100 g). The combined filtrate was separated and the organic phase was extracted with water (150 g). The combined aqueous phase was re-extracted with toluene (150 g) and 1N aqueous solution of hydrogen chloride was added to the resulting aqueous phase until pH=3 with stirring. The precipitated solid was collected by filtration, washed with water (200 g) and dried at 50° C. in the vacuum overnight to give 15.1 g (83.4% of theory) of the title compound.

Intermediate Example Int21.12

(2R)—N-(4-bromophenyl)-2-(4-fluorophenyl)propanamide

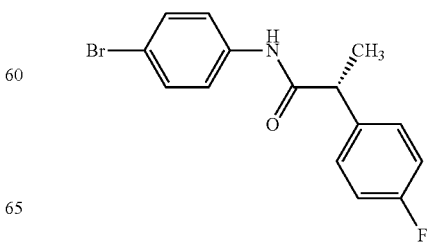

To a stirred solution of (2R)-2-(4-fluorophenyl)propanoic acid (30.79 g) and 4-bromoaniline (30.0 g) in dimethylformamide (522 g) were added sodium bicarbonate (43.9 g) and HATU (99.5 g). The mixture was stirred at room temperature overnight. Then water (1000 g) was added followed by stirring at room temperature for 1 h. The precipitated solid was collected by filtration and washed with water (500 g) and dried by 50° C. in the vacuum overnight to give 52.59 g (93.6% of theory) of the title compound.

Compounds of the Present Invention

Example 01.01

(2R)-2-(4-fluorophenyl)-N-[4-(2-{[2-methoxy-4-(methylsulfonyl)phenyl]-amino}[1,2,4]triazolo[1,5-a]pyridin-6-yl)phenyl]propanamide

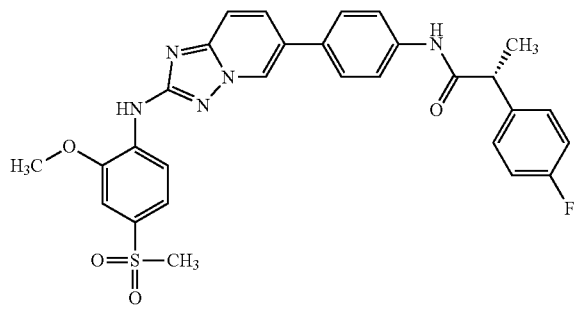

Route 1:

To a stirred suspension of Int08.011 (6.0 g) in DMF (48 mL) and dichloromethane (96 mL) was added sodium bicarbonate (3.69 g), (2R)-2-(4-fluorophenyl)propanoic acid (2.71 g) and HATU (8.36 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Silicagel chromatography gave a solid that was triturated with ethyl acetate to give 7.44 g of the title compound.

$^1$H-NMR (400 MHz, DMSO-d$_6$): δ [ppm]=1.40 (d, 3H), 3.16 (s, 3H), 3.84 (q, 1H), 3.96 (s, 3H), 7.09-7.18 (m, 2H), 7.36-7.44 (m, 3H), 7.51 (dd, 1H), 7.63-7.76 (m, 5H), 7.92 (dd, 1H), 8.48 (d, 1H), 8.60 (s, 1H), 9.10 (d, 1H), 10.16 (s, 1H).

$[α]_D^{20}$: −77.0° (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 30 min. Retention Time: 12.83 min; UV 254 nm; Enantiomeric Ratio: <1%:>99%.

Route 2:

To a stirred suspension of Int21.06 (550 mg) in toluene (18 mL) was added potassium fluoride (260 mg) and powdered potassium phosphate (842 mg) and the flask was degassed twice and backfilled with argon. The mixture was stirred for 15 minutes at r.t. Int21.03 (350 mg), dicyclohexyl(2',6'-dimethoxybiphenyl-2-yl)phosphine (81 mg) and palladium acetate (22 mg) were added and the flask was degassed twice and backfilled with argon. The mixture was heated to 85° C. for 3 h. Water was added and the reaction mixture was extracted with ethyl acetate. The organic phase was washed with saturated sodium chloride solution, dried (sodium sulfate) and the solvent was removed in vacuum. Aminophase-silica-gel chromatography gave a solid that was triturated with a mixture of dichloromethane and hexane to give 452 mg of the title compound.

$^1$H-NMR (300 MHz, DMSO-d$_6$), δ [ppm]=1.39 (3H), 3.16 (3H), 3.83 (1H), 3.95 (3H), 7.08-7.20 (2H), 7.34-7.45 (3H), 7.51 (1H), 7.63-7.77 (5H), 7.92 (1H), 8.48 (1H), 8.64 (1H), 9.11 (1H), 10.19 (1H).

$[α]_D^{20}$: −78.9° (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 30 min. Retention Time: 12.83 min; UV 254 nm; Enantiomeric Ratio: <1%:>99%.

Route 3:

To a stirred solution of S-Phos (452 mg) and palladium(II) acetate (112 mg) in n-propanol (35.5 g) were added 6-chloro-N-[2-methoxy-4-(methylsulfonyl)phenyl][1,2,4]triazolo[1,5-a]pyridin-2-amine (1.764 g) and (4-{[(2R)-2-(4-fluorophenyl)propanoyl]amino}phenyl)boronic acid (1.665 g). Then n-propanol (5.0 g) and 2M aqueous potassium carbonate solution (12.14 g) were added and the mixture was stirred at reflux for 6 h. The mixture was cooled with stirring. The precipitated solid was collected by filtration, washed with n-propanol and water and dried at 60° C. in the vacuum for 16 h to give 2.59 g (92.6% of theory) of the title compound.

Route 4:

To a stirred solution of X-Phos (524 mg) and palladium(II) acetate (112 mg) in n-propanol (70.0 g) were added (2-{[2-methoxy-4-(methylsulfonyl)phenyl]amino}[1,2,4]triazolo[1,5-a]pyridin-6-yl)boronic acid (Int21.11) (1.610 g) and (2R)—N-(4-bromophenyl)-2-(4-fluorophenyl)propanamide (Int21.12) (1.955 g). Then n-propanol (5.0 g) and 2M aqueous potassium carbonate solution (12.14 g) were added and the mixture was stirred at reflux for 1.5 h. The mixture was cooled with stirring. The precipitated solid was collected by filtration, washed with n-propanol and water and dried at 60° C. in the vacuum for 16 h to give 1.63 g (58.4% of theory) of the title compound.

Racemate01.01.r

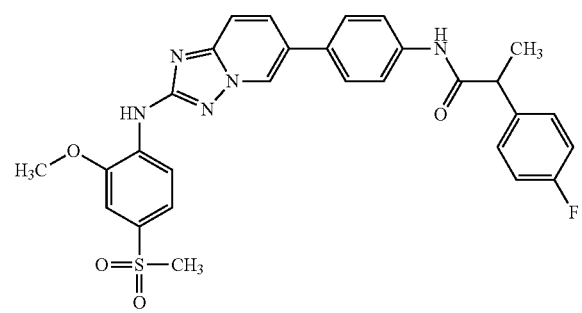 [SMILES: COc1cc(S(C)(=O)=O)ccc1Nc1nc2ccc(-c3ccc(NC(=O)[C@H](C)c4ccc(F)cc4)cc3)cn2n1]

Starting with Int01.05 and Int03.02, Racemate01.01.r was prepared analogously to the procedure for the preparation of Int08.020.

Racemate01.02.r

N-[4-(2-{[2-ethoxy-4-(methylsulfonyl)phenyl]amino}[1,2,4]triazolo[1,5-a]-pyridin-6-yl)phenyl]-2-(4-fluorophenyl)propanamide

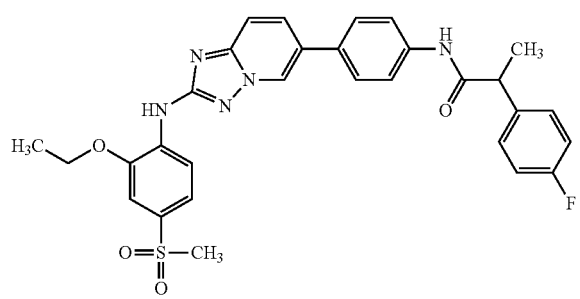 [SMILES: CCOc1cc(S(C)(=O)=O)ccc1Nc1nc2ccc(-c3ccc(NC(=O)[C@H](C)c4ccc(F)cc4)cc3)cn2n1]

Starting with Int01.05 and Int04.03, Racemate01.02.r was prepared analogously to the procedure for the preparation of Int08.020.

Example 01.02

(2R)—N-[4-(2-{[2-ethoxy-4-(methylsulfonyl)phenyl]amino}[1,2,4]triazolo[1,5-a]pyridin-6-yl)phenyl]-2-(4-fluorophenyl)propanamide

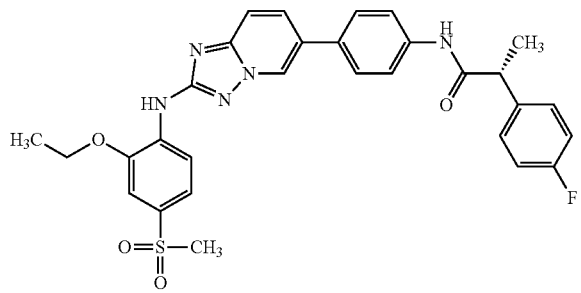

The enantiomers of 180 mg of Racemate01.02.r were separated using chiral HPLC.

Column: Chiralpak IA 5μ 250×30; Flow: 20.0 mL/min; Solvent: A: Ethanol with 0.1% formic acid; Solvent: 100% A. Retention time of the title compound: 37.2-49.1 min (Peak 2). Yield: 74 mg.

$^1$H-NMR (300 MHz, DMSO-d$_6$): δ [ppm]=1.35-1.49 (m, 6H), 3.15 (s, 3H), 3.84 (q, 1H), 4.22 (q, 2H), 7.07-7.19 (m, 2H), 7.36-7.44 (m, 3H), 7.50 (dd, 1H), 7.61-7.78 (m, 5H), 7.93 (dd, 1H), 8.44-8.54 (m, 2H), 9.10 (d, 1H), 10.19 (s, 1H).

$[\alpha]_D^{20}$: −72.7° (in DMSO).

Column: Chiralpak IA 5μ 150×4.6; Flow: 1.00 mL/min; Solvent: A: Ethanol with 0.1% formic acid; Solvent: 100% A. Run Time: 30 min. Retention Time: 14.3 min; UV 254 nm; Enantiomeric Ratio: <1%:>99%.

Example 01.03

(2R)-2-(4-fluorophenyl)-N-[4-(2-{[4-(methylsulfonyl)-2-(2,2,2-trifluoro-ethoxy)phenyl]amino}[1,2,4]triazolo[1,5-a]pyridin-6-yl)phenyl]propanamide

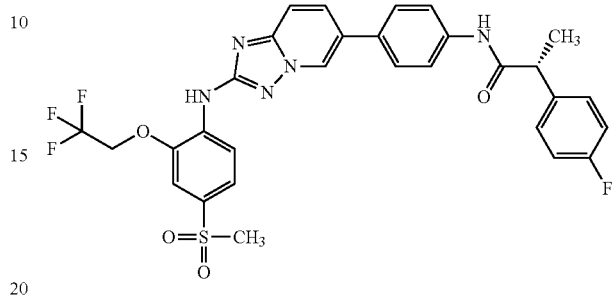

Route 1:

To a stirred suspension of Int08.021 (5.6 g) in DMF (45 mL) and dichloromethane (90 mL) was added sodium bicarbonate (1.97 g), (2R)-2-(4-fluorophenyl)propanoic acid (2.17 g) and HATU (6.69 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave a solid that was triturated with a mixture of ethyl acetate and cyclohexane to give 6.60 g of the title compound.

$^1$H-NMR (300 MHz, DMSO-d$_6$): δ [ppm]=1.39 (d, 3H), 3.17 (s, 3H), 3.83 (q, 1H), 5.00 (q, 2H), 7.08-7.19 (m, 2H), 7.35-7.45 (m, 2H), 7.58-7.76 (m, 7H), 7.93 (dd, 1H), 8.50 (d, 1H), 8.59 (s, 1H), 9.11 (d, 1H), 10.19 (s, 1H).

$[\alpha]_D^{20}$: −69.3° (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 20 min. Retention Time: 12.28 min; UV 254 nm; Enantiomeric Ratio: <1%:>99%.

Route 2:

To a stirred suspension of Int21.08 (88.0 mg) in toluene (3.0 mL) and NMP (0.3 mL) was added Int21.07 (66.0 mg), powdered potassium phosphate monohydrate (133 mg), dicyclohexyl(2',6'-dimethoxybiphenyl-2-yl)phosphine (17.2 mg) and palladium acetate (4.7 mg) and the flask was degassed twice and backfilled with argon. The mixture was heated to reflux for 1 h. The reaction mixture was filtered through an aminophase-silicagel column and the solvent was removed in vacuum. Preparative reverse phase HPLC gave a solid that was triturated with a mixture of dichloromethane and hexane to give 43 mg of the title compound.

$^1$H-NMR (400 MHz, DMSO-d$_6$), δ [ppm]=1.42 (3H), 3.19 (3H), 3.86 (1H), 5.02 (2H), 7.12-7.20 (2H), 7.39-7.46 (2H), 7.62-7.67 (2H), 7.68-7.77 (5H), 7.96 (1H), 8.53 (1H), 8.59 (1H), 9.13 (1H), 10.19 (1H).

$[\alpha]_D^{20}$: −68.4° (in DMSO).

Column: Chiralcel OD-RH 150×4.6; Flow: 1.00 mL/min; Solvent: A: Water with 0.1% formic acid, B: Acetonitrile;

Solvent mixture: 40% A+60% B. Run Time: 20 min.; UV 254 nm; Enantiomeric Ratio: <1%:>99%.

Racemate01.03.r 2-(4-fluorophenyl)-N-[4-(2-{[4-(methylsulfonyl)-2-(2,2,2-trifluoroethoxy)-phenyl]amino}[1,2,4]triazolo[1,5-a]pyridin-6-yl)phenyl]propanamide

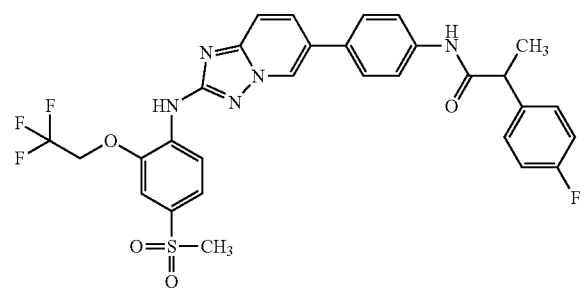 [SMILES: CC(C(=O)Nc1ccc(-c2ccc3nc(Nc4ccc(S(C)(=O)=O)cc4OCC(F)(F)F)nn3c2)cc1)c1ccc(F)cc1]

Starting with Int01.05 and Int05.03, Racemate01.03.r was prepared analogously to the procedure for the preparation of Int08.020.

Example 01.04

4-{[6-(4-{[(2R)-2-(4-fluorophenyl)propanoyl]amino}phenyl)[1,2,4]triazolo[1,5-a]pyridin-2-yl]amino}-3-methoxy-N-(2,2,2-trifluoroethyl)benzamide

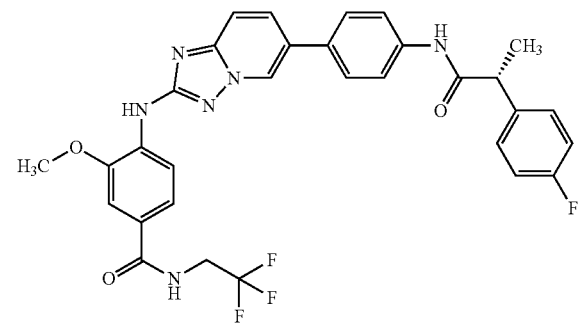 [SMILES: COc1cc(C(=O)NCC(F)(F)F)ccc1Nc1nc2ccc(-c3ccc(NC(=O)[C@H](C)c4ccc(F)cc4)cc3)cn2n1]

To a stirred suspension of Int08.031 (500 mg) in DMF (4.3 mL) and dichloromethane (8.6 mL) was added sodium bicarbonate (184 mg), (2R)-2-(4-fluorophenyl)propanoic acid (203 mg) and HATU (625 mg). The mixture was stirred at room temperature for 4 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was triturated with warm ethanol to give 300 mg of the title compound.

$^1$H-NMR (300 MHz, DMSO-$d_6$): δ [ppm]=1.39 (d, 3H), 3.83 (q, 1H), 3.92 (s, 3H), 3.99-4.16 (m, 2H), 7.09-7.18 (m, 2H), 7.36-7.44 (m, 2H), 7.51-7.60 (m, 2H), 7.62-7.76 (m, 5H), 7.91 (dd, 1H), 8.30-8.40 (m, 2H), 8.90 (t, 1H), 9.11 (d, 1H), 10.18 (s, 1H)

$[α]_D^{20}$: −70.5° (in DMSO).

Column: Chiralpak IA 5μ 150×4.6; Flow: 1.00 mL/min; Solvent: A: Ethanol, B: Methanol; Solvent mixture: 50% A+50% B. Run Time: 20 min. Retention Time: 6.67 min; UV 254 nm; Enantiomeric Ratio: <2%:>98%.

Racemate01.04.r

4-{[6-(4-{[2-(4-fluorophenyl)propanoyl]amino}phenyl)[1,2,4]triazolo[1,5-a]-pyridin-2-yl]amino}-3-methoxy-N-(2,2,2-trifluoroethyl)benzamide

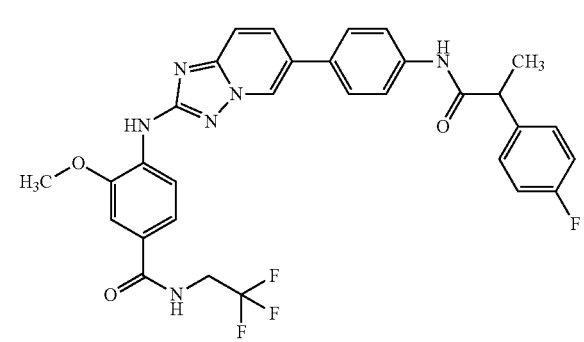 [SMILES: COc1cc(C(=O)NCC(F)(F)F)ccc1Nc1nc2ccc(-c3ccc(NC(=O)C(C)c4ccc(F)cc4)cc3)cn2n1]

Starting with Int01.05 and Int02.03, Racemate01.04.r was prepared analogously to the procedure for the preparation of Int08.020.

Example 01.05

4-{[6-(4-{[(2R)-2-(4-fluorophenyl)propanoyl]amino}phenyl)[1,2,4]triazolo[1,5-a]pyridin-2-yl]amino}-3-methoxybenzamide

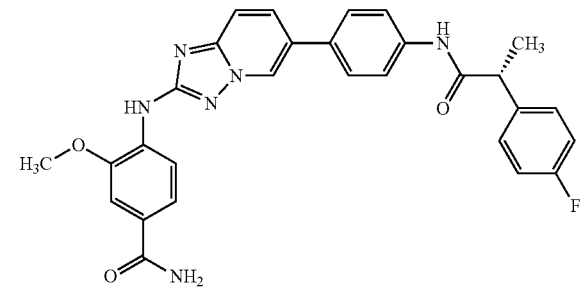 [SMILES: COc1cc(C(N)=O)ccc1Nc1nc2ccc(-c3ccc(NC(=O)[C@H](C)c4ccc(F)cc4)cc3)cn2n1]

To a stirred suspension of Int08.041 (65 mg) in DMF (0.5 mL) and dichloromethane (1.0 mL) was added sodium bicarbonate (44 mg), (2R)-2-(4-fluorophenyl)propanoic acid (32 mg) and HATU (99 mg). The mixture was stirred at room temperature for 2 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave a solid that was triturated with dichloromethane to give 78 mg of the title compound.

¹H-NMR (400 MHz, DMSO-d₆): δ [ppm]=1.42 (d, 3H), 3.86 (q, 1H), 3.93 (s, 3H), 7.12-7.22 (m, 3H), 7.39-7.46 (m, 2H), 7.51-7.59 (m, 2H), 7.63-7.68 (m, 1H), 7.68-7.77 (m, 4H), 7.85 (br. s., 1H), 7.92 (dd, 1H), 8.26 (s, 1H), 8.33 (d, 1H), 9.13 (d, 1H), 10.19 (s, 1H).

Column: Chiralcel OD-RH 150×4.6; Flow: 1.00 mL/min; Solvent: A: Water with 0.1% formic acid, B: Acetonitrile; Solvent mixture: 50% A+50% B. Run Time: 30 min. Retention Time: 14.34 min; UV 254 nm; Enantiomeric Ratio: <1%:>99%.

Racemate01.05.r

4-{[6-(4-{[2-(4-fluorophenyl)propanoyl]amino}phenyl)[1,2,4]triazolo[1,5-a]pyridin-2-yl]amino}-3-methoxybenzamide

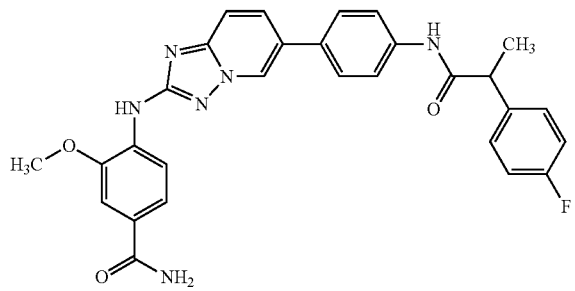 [SMILES: COc1cc(C(N)=O)ccc1Nc1nc2ccc(-c3ccc(NC(=O)C(C)c4ccc(F)cc4)cc3)cn2n1]

Starting with Int01.05 and 4-bromo-3-methoxybenzamide, Racemate01.05.r was prepared analogously to the procedure for the preparation of Int08.020.

Example 01.06

4-{[6-(4-{[(2R)-2-(4-fluorophenyl)propanoyl]amino}phenyl)[1,2,4]triazolo[1,5-a]pyridin-2-yl]amino}-3-(2,2,2-trifluoroethoxy)benzamide

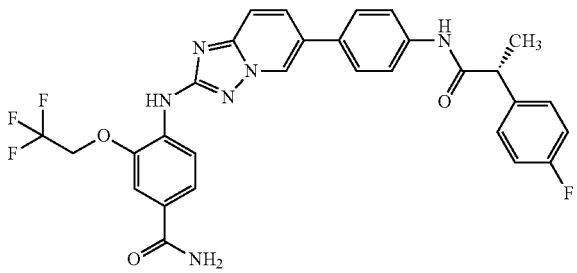 [SMILES: C[C@@H](C(=O)Nc1ccc(-c2ccc3nc(Nc4ccc(C(N)=O)cc4OCC(F)(F)F)nn3c2)cc1)c1ccc(F)cc1]

To a stirred suspension of Int08.051 (70 mg) in DMF (0.5 mL) and dichloromethane (1.0 mL) was added sodium bicarbonate (27 mg), (2R)-2-(4-fluorophenyl)propanoic acid (32 mg) and HATU (90 mg). The mixture was stirred at room temperature for 4 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was recrystallized from ethyl acetate to give 80 mg of the title compound.

¹H-NMR (400 MHz, DMSO-d₆): δ [ppm]=1.40 (d, 3H), 3.84 (q, 1H), 4.88 (q, 2H), 7.09-7.17 (m, 2H), 7.23 (br. s., 1H), 7.36-7.44 (m, 2H), 7.59-7.74 (m, 7H), 7.81 (br. s., 1H), 7.91 (dd, 1H), 8.20 (s, 1H), 8.33 (d, 1H), 9.11 (d, 1H), 10.16 (s, 1H).

$[\alpha]_D^{20}$: −56.4° (in DMSO).

Column: Chiralpak IA 5μ 150×4.6; Flow: 1.00 mL/min; Solvent: A: Ethanol, B: Methanol; Solvent mixture: 50% A+50% B. Run Time: 20 min. Retention Time: 5.98 min; UV 254 nm; Enantiomeric Ratio: <1%:>99%.

Racemate01.06.r

4-{[6-(4-{[2-(4-fluorophenyl)propanoyl]amino}phenyl)[1,2,4]triazolo[1,5-a]pyridin-2-yl]amino}-3-(2,2,2-trifluoroethoxy)benzamide

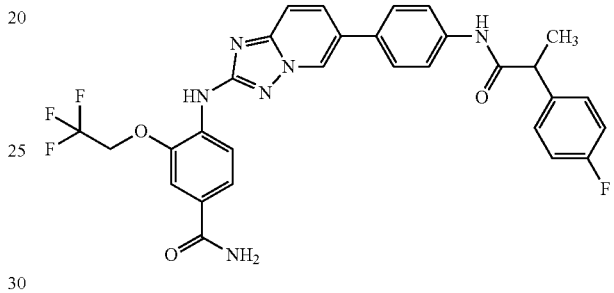

Starting with Int01.05 and Int06.03, Racemate01.06.r was prepared analogously to the procedure for the preparation of Int08.020.

Example 01.07

(2R)—N-{4-[2-({4-[(3-fluoroazetidin-1-yl)carbonyl]-2-methoxyphenyl}amino)-[1,2,4]triazolo[1,5-a]pyridin-6-yl)]phenyl}-2-(4-fluorophenyl)propanamide

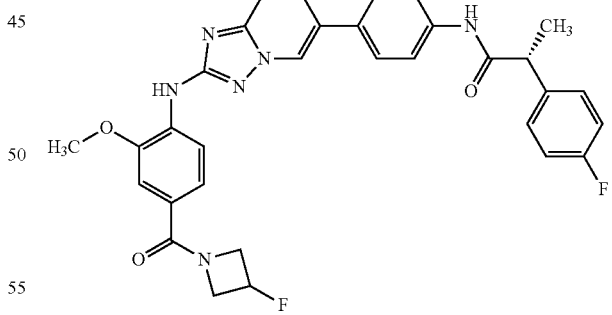

Route 1:

To a stirred suspension of Int08.061 (1.10 g) in DMF (8.5 mL) and dichloromethane (17 mL) was added sodium bicarbonate (427 mg), (2R)-2-(4-fluorophenyl)propanoic acid (470 mg) and HATU (1.45 g). The mixture was stirred at room temperature for 4 h. Water was added, and the mixture was stirred for 30 minutes. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave 1.13 g of the title compound.

$^1$H-NMR (400 MHz, DMSO-d$_6$): δ [ppm]=1.42 (d, 3H), 3.86 (q, 1H), 3.93 (s, 3H), 3.98-4.80 (m, 4H), 5.44 (m, 1H, J=57.5 Hz), 7.12-7.20 (m, 2H), 7.26 (d, 1H), 7.30 (dd, 1H), 7.40-7.46 (m, 2H), 7.63-7.76 (m, 5H), 7.93 (dd, 1H), 8.31-8.39 (m, 2H), 9.11 (d, 1H), 10.19 (s, 1H).

[α]$_D^{20}$: −70.0° (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 20 min. Retention Time: 13.88 min; UV 254 nm; Enantiomeric Ratio: <1%: >99%.

Route 2:

To a stirred suspension of Int21.09 (90.0 mg) in toluene (3.0 mL) was added Int21.07 (103.0 mg), powdered potassium phosphate monohydrate (203 mg), potassium fluoride (63 mg), dicyclohexyl(2',6'-dimethoxybiphenyl-2-yl)phosphine (19.7 mg) and palladium acetate (5.4 mg) and the flask was degassed twice and backfilled with argon. The mixture was heated to reflux for 2 h. The reaction mixture was filtered through an aminophase-silicagel column and the solvent was removed in vacuum. Silicagel chromatography followed by aminophase-silicagel chromatography gave 80 mg of the title compound.

$^1$H-NMR (300 MHz, DMSO-d$_6$), δ [ppm]=1.42 (3H), 3.80-3.96 (4H), 3.98-4.75 (4H), 5.28-5.60 (1H), 7.10-7.21 (2H), 7.23-7.34 (2H), 7.43 (2H), 7.63-7.79 (5H), 7.93 (1H), 8.32-8.42 (2H), 9.12 (1H), 10.20 (1H).

[α]$_D^{20}$: −81.6° (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 20 min. Retention Time: 13.88 min; UV 254 nm; Enantiomeric Ratio: <1%:>99%.

Racemate01.07.r

N-{4-[2-({4-[(3-fluoroazetidin-1-yl)carbonyl]-2-methoxyphenyl}amino)-[1,2,4]triazolo[1,5-a]pyridin-6-yl]phenyl}-2-(4-fluorophenyl)propanamide

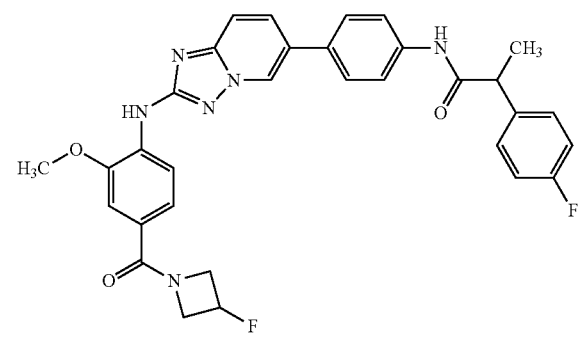 [SMILES: COc1cc(C(=O)N2CC(F)C2)ccc1Nc1nc2ccc(-c3ccc(NC(=O)C(C)c4ccc(F)cc4)cc3)cn2n1]

Starting with Int01.05 and Int02.05, Racemate01.07.r was prepared analogously to the procedure for the preparation of Int08.020.

Example 01.08

(2R)—N-[4-(2-{[4-(azetidin-1-ylcarbonyl)-2-methoxyphenyl]amino}[1,2,4]-triazolo[1,5-a]pyridin-6-yl)phenyl]-2-(4-fluorophenyl)propanamide

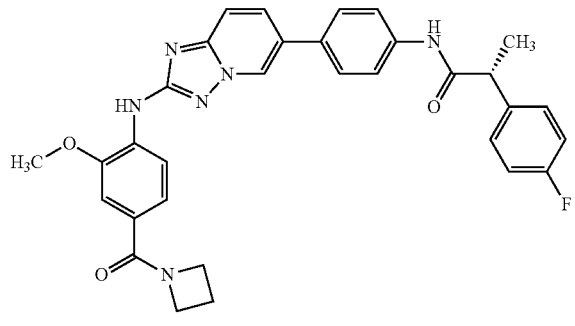 [SMILES: COc1cc(C(=O)N2CCC2)ccc1Nc1nc2ccc(-c3ccc(NC(=O)[C@H](C)c4ccc(F)cc4)cc3)cn2n1]

To a stirred suspension of Int08.071 (200 mg) in DMF (1.6 mL) and dichloromethane (3.2 mL) was added sodium bicarbonate (122 mg), (2R)-2-(4-fluorophenyl)propanoic acid (89 mg) and HATU (275 mg). The mixture was stirred at room temperature for 4 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography followed by silica gel chromatography gave a solid that was triturated with ether to give 250 mg of the title compound.

$^1$H-NMR (300 MHz, DMSO-d$_6$): δ [ppm]=1.39 (d, 3H), 2.22 (quin, 2H), 3.78-3.92 (m, 4H), 4.00 (br. s., 2H), 4.32 (br. s, 2H), 7.09-7.17 (m, 2H), 7.20-7.26 (m, 2H), 7.36-7.44 (m, 2H), 7.59-7.75 (m, 5H), 7.89 (dd, 1H), 8.24-8.36 (m, 2H), 9.08 (d, 1H), 10.18 (s, 1H).

[α]$_D^{20}$: −63.5° D (in DMSO).

Column: Chiralcel OD-RH 150×4.6; Flow: 1.00 mL/min; Solvent: A: Water with 0.1% formic acid, B: Acetonitrile; Solvent mixture: 40% A+60% B. Run Time: 30 min. Retention Time: 14.22 min; UV 254 nm; Enantiomeric Ratio: <2%:>98%.

Racemate01.08.r

N-[4-(2-{[4-(azetidin-1-ylcarbonyl)-2-methoxyphenyl]amino}[1,2,4]triazolo[1,5-a]pyridin-6-yl)phenyl]-2-(4-fluorophenyl)propanamide

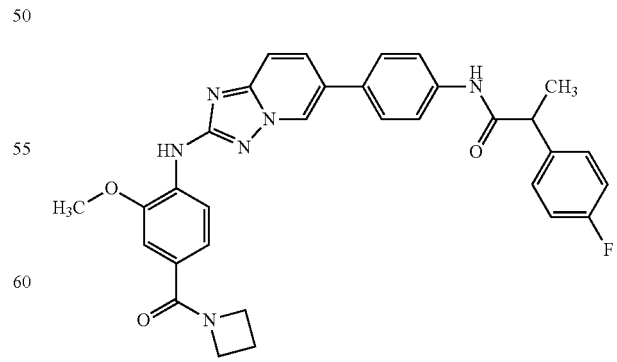

Starting with Int01.05 and Int02.04, Racemate01.08.r was prepared analogously to the procedure for the preparation of Int08.020.

Example 01.09

(2R)-2-(4-fluorophenyl)-N-[4-(2-{[2-methoxy-4-(2-oxo-1,3-oxazolidin-3-yl)phenyl]amino}[1,2,4]triazolo[1,5-a]pyridin-6-yl)phenyl]propanamide

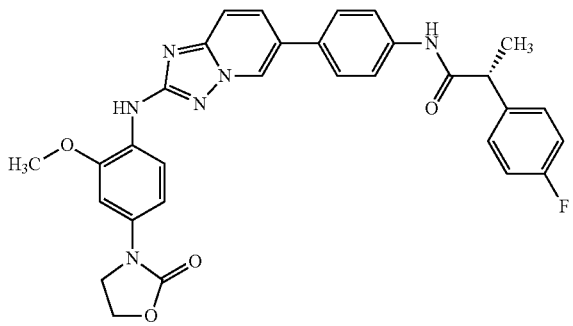 [SMILES: COc1cc(N2CCOC2=O)ccc1Nc1nc2ccc(-c3ccc(NC(=O)[C@H](C)c4ccc(F)cc4)cc3)cn2n1]

To a stirred suspension of Int08.081 (100 mg) in DMF (0.8 mL) and dichloromethane (1.6 mL) was added sodium bicarbonate (41 mg), (2R)-2-(4-fluorophenyl)propanoic acid (44 mg) and HATU (137 mg). The mixture was stirred at room temperature for 16 h. Water was added, and the mixture was stirred for 30 minutes. A half-saturated solution of sodium bicarbonate was added and the mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was triturated with ethyl acetate to give 85 mg of the title compound.

$^1$H-NMR (400 MHz, DMSO-$d_6$): δ [ppm]=1.39 (d, 3H), 3.77-3.89 (m, 4H), 4.04 (dd, 2H), 4.36-4.45 (m, 2H), 6.98 (dd, 1H), 7.10-7.16 (m, 2H), 7.36-7.43 (m, 3H), 7.54-7.59 (m, 1H), 7.63-7.72 (m, 4H), 7.85 (dd, 1H), 7.97 (s, 1H), 8.13 (d, 1H), 8.97-9.07 (m, 1H), 10.15 (s, 1H).

$[α]_D^{20}$: −72.1° (in DMSO).

Column: Chiralpak IB 5μ 150×4.6; Flow: 1.00 mL/min; Solvent: A: Ethanol, B: Methanol; Solvent mixture: 50% A+50% B. Run Time: 20 min. Retention Time: 5.74 min; UV 254 nm; Enantiomeric Ratio: <1%:>99%.

Racemate01.09.r 2-(4-fluorophenyl)-N-[4-(2-{[2-methoxy-4-(2-oxo-1,3-oxazolidin-3-yl)-phenyl]amino}[1,2,4]triazolo[1,5-a]pyridin-6-yl)phenyl]propanamide

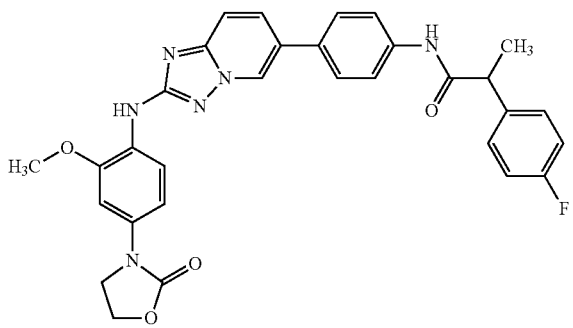 [SMILES: COc1cc(N2CCOC2=O)ccc1Nc1nc2ccc(-c3ccc(NC(=O)C(C)c4ccc(F)cc4)cc3)cn2n1]

Starting with Int01.05 and Int07.01, Racemate01.09.r was prepared analogously to the procedure for the preparation of Int08.020.

Racemate01.10.r 2-(4-fluorophenyl)-3-hydroxy-N-[4-(2-{[4-(methylsulfonyl)-2-(2,2,2-tri-fluoroethoxy)phenyl]amino}[1,2,4]triazolo[1,5-a]pyridin-6-yl)phenyl]-propanamide

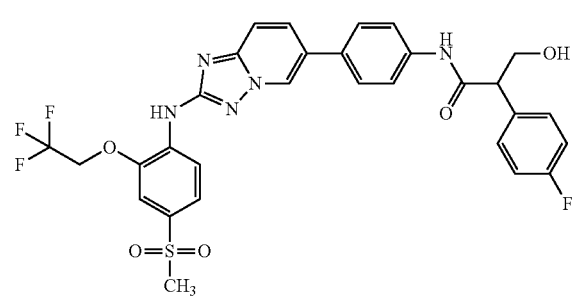 [SMILES: CS(=O)(=O)c1ccc(Nc2nc3ccc(-c4ccc(NC(=O)C(CO)c5ccc(F)cc5)cc4)cn3n2)c(OCC(F)(F)F)c1]

To a stirred solution of Int08.143 (340 mg) in tetrahydrofurane (20 mL) was added a solution of TBAF in THF (0.77 mL; c=1.0 M). The mixture was stirred at room temperature for 1 h. Water was added and the reaction mixture was extracted with ethyl acetate. The organic phase was washed with saturated sodium chloride solution, dried (sodium sulfate) and the solvent was removed in vacuum. Aminophase-silica-gel chromatography gave 193 mg of the title compound.

Example 01.10

(−)-2-(4-fluorophenyl)-3-hydroxy-N-[4-(2-{[4-(methylsulfonyl)-2-(2,2,2-tri-fluoroethoxy)phenyl]amino}[1,2,4]triazolo[1,5-a]pyridin-6-yl)phenyl]propanamide

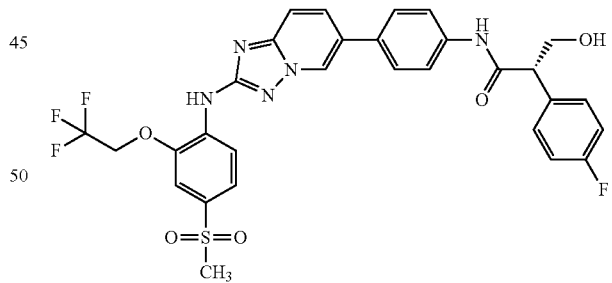

The enantiomers of 176 mg of Racemate01.10.r were separated using chiral HPLC.

Column: Chiralpak IB 5μ 250×20 mm; Flow: 20.0 mL/min; Solvent: A: Hexane, B: Ethanol; Solvent mixture: 50% A+50% B. Retention time of the title compound: 9.7-11.1 min (Peak 1). Yield: 75 mg.

$^1$H-NMR (400 MHz, DMSO-$d_6$): δ [ppm]=3.18 (s, 3H), 3.50-3.60 (m, 1H), 3.81-3.90 (m, 1H), 3.98-4.08 (m, 1H), 4.92-5.08 (m, 3H), 7.10-7.19 (m, 2H), 7.36-7.45 (m, 2H), 7.59-7.77 (m, 7H), 7.95 (dd, 1H), 8.52 (d, 1H), 8.58 (s, 1H), 9.13 (d, 1H), 10.26 (s, 1H).

$[α]_D^{20}$: −72.9° (in DMSO).

Column: Chiralpak IB 5μ 150×4.6; Flow: 1.00 mL/min; Solvent: A: Hexane, B: Ethanol; Solvent mixture: 50% A+50% B. Run Time: 30 min. Retention Time: 6.80 min; UV 254 nm; Enantiomeric Ratio: >99%:<1%.

Example 01.11

(2R)-2-amino-2-(4-fluorophenyl)-N-[4-(2-{[2-methoxy-4-(methylsulfonyl)-phenyl]amino}[1,2,4]triazolo[1,5-a]pyridin-6-yl)phenyl]ethanamide

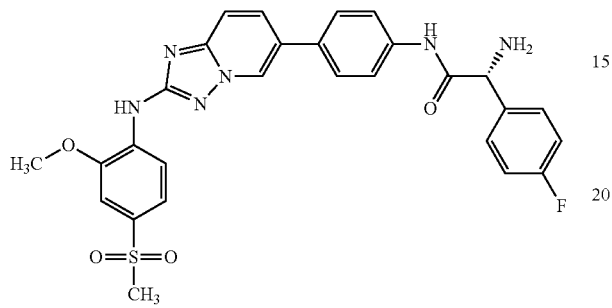

To a stirred solution of Int08.150 (260 mg) in dichloromethane (16 mL) was added TFA (0.76 mL). The mixture was stirred at room temperature for 2 h. Further TFA was added (1 mL) and the mixture was stirred at room temperature for 72 h. A half-saturated solution of potassium carbonate was added until pH 9 was reached. The mixture was extracted with dichloromethane and methanol (10:1 mixture). The solution was filtered through an aminophase-silica-gel column. The solvent was removed in vacuum to give a solid that was recrystallized from ethanol to give 210 mg of the title compound.

$^1$H-NMR (300 MHz, DMSO-d$_6$, detected signals): δ [ppm]=3.16 (s, 3H), 3.95 (s, 3H), 4.53 (s, 1H), 7.08-7.19 (m, 2H), 7.42 (d, 1H), 7.45-7.55 (m, 3H), 7.67 (d, 1H), 7.73 (br. s, 4H), 7.93 (dd, 1H), 8.48 (d, 1H), 8.63 (s, 1H), 9.12 (d, 1H), 10.17 (br. s, 1H)

$[α]_D^{20}$: −43.1° (in DMSO).

Example 01.12

4-{[6-(4-{[(2R)-2-(4-fluorophenyl)propanoyl]amino}phenyl)[1,2,4]triazolo[1,5-a]pyridin-2-yl]amino}-3-methoxy-N,N-dimethylbenzamide

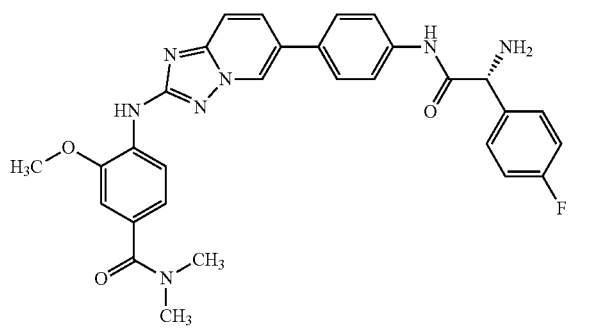 [SMILES: COc1cc(C(=O)N(C)C)ccc1Nc1nc2ccc(-c3ccc(NC(=O)[C@H](N)c4ccc(F)cc4)cc3)cn2n1]

Route 1:
Starting with Int08.091, Example 01.12 was prepared analogously to the procedure for the preparation of Example 01.04.

$^1$H-NMR (400 MHz, DMSO-d$_6$): δ [ppm]=1.40 (d, 3H), 2.95 (s, 6H), 3.83 (q, 1H), 3.88 (s, 3H), 6.99-7.06 (m, 2H), 7.10-7.17 (m, 2H), 7.37-7.43 (m, 2H), 7.59-7.64 (m, 1H), 7.65-7.74 (m, 4H), 7.89 (dd, 1H), 8.17 (s, 1H), 8.28 (d, 1H), 9.03-9.10 (m, 1H), 10.16 (s, 1H).

Route 2:
To a stirred suspension of Int21.10 (130 mg) in toluene (3.0 mL) and NMP (0.3 mL) was added Int21.07 (162 mg), powdered potassium phosphate monohydrate (319 mg), dicyclohexyl(2',6'-dimethoxybiphenyl-2-yl)phosphine (30.9 mg) and Pd$_2$dba$_3$ (17.2 mg) and the flask was degassed twice and backfilled with argon. The mixture was heated to reflux for 2 h. The reaction mixture was filtered through an aminophase-silicagel column and the solvent was removed in vacuum. The residue was dissolved in ethyl acetat and the solution was washed with water. The solvent was removed in vacuum.

Example 01.13

(2R)-2-(4-fluorophenyl)-N-[4-(2-{[2-methoxy-4-(pyrrolidin-1-ylcarbonyl)phenyl]amino}[1,2,4]triazolo[1,5-a]pyridin-6-yl)phenyl]propanamide

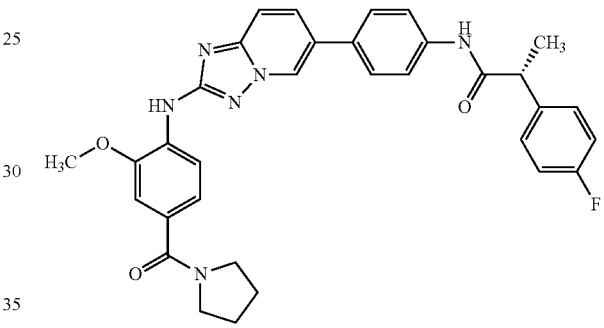

Starting with Int08.101, Example 01.13 was prepared analogously to the procedure for the preparation of Example 01.08.

$^1$H-NMR (300 MHz, DMSO-d$_6$): δ [ppm]=1.39 (d, 3H), 1.80 (br. s., 4H), 3.45 (br. s., 4H), 3.79-3.85 (m, 1H), 3.88 (s, 3H), 7.08-7.19 (m, 4H), 7.40 (dd, 2H), 7.58-7.75 (m, 5H), 7.89 (dd, 1H), 8.21 (s, 1H), 8.28 (d, 1H), 9.08 (s, 1H), 10.17 (s, 1H).

$[α]_D^{20}$: −69.3° (in DMSO).

Example 01.14

(2R)—N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)propanamide

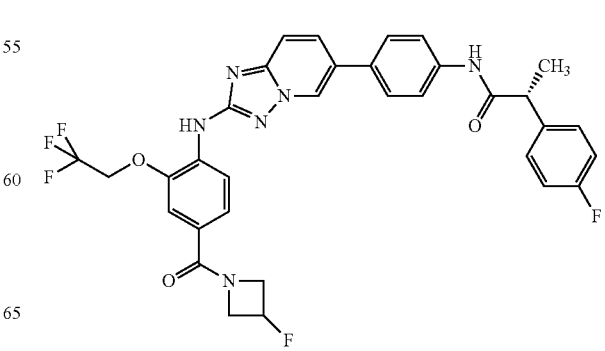

Starting with Int08.111, Example 01.14 was prepared analogously to the procedure for the preparation of Example 01.04.

$^1$H-NMR (300 MHz, DMSO-d$_6$): δ [ppm]=1.39 (d, 3H), 3.83 (q, 1H), 3.91-4.73 (m, 4H), 4.92 (d, 2H), 5.25-5.58 (m, 1H), 7.13 (t, 2H), 7.33-7.46 (m, 4H), 7.59-7.76 (m, 5H), 7.91 (dd, 1H), 8.27 (s, 1H), 8.32-8.40 (m, 1H), 9.10 (s, 1H), 10.18 (s, 1H).

$[α]_D^{20}$: −47.2° (in DMSO).

Example 01.15

(2R)-2-(4-fluorophenyl)-N-{4-[2-({4-[(3-hydroxyazetidin-1-yl)carbonyl]-2-(2,2,2-trifluoroethoxy)phenyl}amino)[1,2,4]triazolo[1,5-a]pyridin-6-yl]phenyl}propanamide

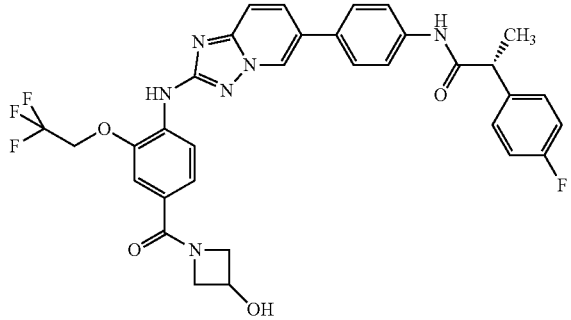 [SMILES: C[C@@H](C(=O)Nc1ccc(-c2ccc3nc(Nc4ccc(C(=O)N5CC(O)C5)cc4OCC(F)(F)F)nn3c2)cc1)c1ccc(F)cc1]

Starting with Int08.121, Example 01.15 was prepared analogously to the procedure for the preparation of Example 01.05.

$^1$H-NMR (300 MHz, DMSO-d$_6$): δ [ppm]=1.35-1.43 (m, 3H), 3.70-3.91 (m, 3H), 3.97-4.31 (m, 2H), 4.48 (br. s., 2H), 4.91 (q, 2H), 7.07-7.19 (m, 2H), 7.31-7.45 (m, 4H), 7.60-7.75 (m, 5H), 7.91 (dd, 1H), 8.21 (s, 1H), 8.34 (d, 1H), 9.08 (d, 1H), 10.16 (s, 1H).

Example 01.16

(2R)-2-(4-fluorophenyl)-N-[4-(2-{[4-(pyrrolidin-1-ylcarbonyl)-2-(2,2,2-trifluoroethoxy)phenyl]amino}[1,2,4]triazolo[1,5-a]pyridin-6-yl)phenyl]propanamide

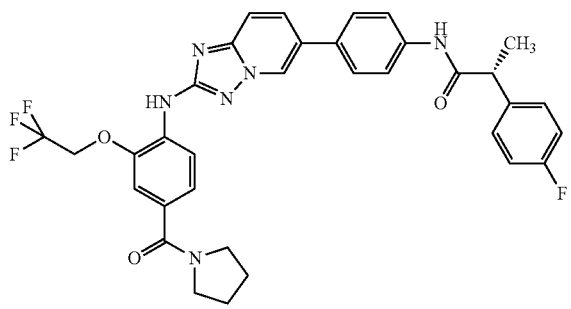 [SMILES: C[C@@H](C(=O)Nc1ccc(-c2ccc3nc(Nc4ccc(C(=O)N5CCCC5)cc4OCC(F)(F)F)nn3c2)cc1)c1ccc(F)cc1]

Starting with Int08.131, Example 01.16 was prepared analogously to the procedure for the preparation of Example 01.09.

$^1$H-NMR (300 MHz, DMSO-d$_6$): δ [ppm]=1.39 (d, 3H), 1.81 (br. s., 4H), 3.44 (d, 4H), 3.83 (q, 1H), 4.89 (q, 2H), 7.07-7.19 (m, 2H), 7.23-7.34 (m, 2H), 7.35-7.45 (m, 2H), 7.59-7.74 (m, 5H), 7.90 (dd, 1H), 8.15 (s, 1H), 8.31 (d, 1H), 9.09 (s, 1H), 10.18 (s, 1H).

$[α]_D^{20}$: −69.6° (in DMSO).

Racemate01.17.r 2-(4-fluorophenyl)-3-hydroxy-N-[4-(2-{[2-methoxy-4-(methylsulfonyl)phenyl]amino}[1,2,4]triazolo[1,5-a]pyridin-6-yl)phenyl]propanamide

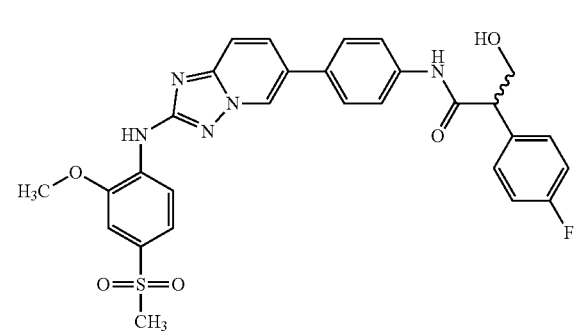 [SMILES: COc1cc(S(C)(=O)=O)ccc1Nc1nc2ccc(-c3ccc(NC(=O)C(CO)c4ccc(F)cc4)cc3)cn2n1]

Starting with Int08.144, Racemate01.17.r was prepared analogously to the procedure for the preparation of Racemate01.10.r.

Example 01.17

(2S)-2-(4-fluorophenyl)-3-hydroxy-N-[4-(2-{[2-methoxy-4-(methylsulfonyl)phenyl]amino}[1,2,4]triazolo[1,5-a]pyridin-6-yl)phenyl]propanamide

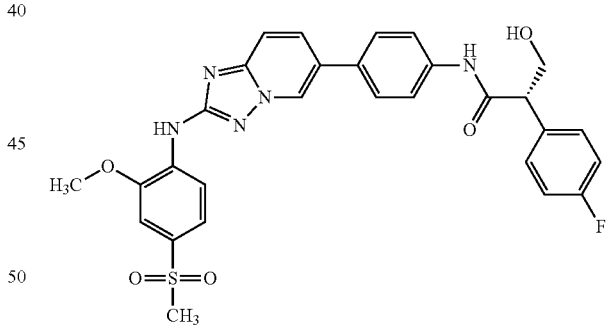

The enantiomers of 175 mg of Racemate01.17.r were separated using chiral HPLC.

Column: Chiralpak IB 5μ 250×20 mm; Flow: 20.0 mL/min; Solvent: A: Hexane, B: Ethanol; Solvent mixture: 50% A+50% B. Retention time of the title compound: 15.2-17.4 min (Peak 1). Yield: 71 mg.

$^1$H-NMR (300 MHz, DMSO-d$_6$): δ [ppm]=3.16 (s, 3H), 3.54 (dt, 1H), 3.84 (dd, 1H), 3.92-4.09 (m, 4H), 4.96 (t, 1H), 7.08-7.19 (m, 2H), 7.35-7.45 (m, 3H), 7.51 (dd, 1H), 7.63-7.77 (m, 5H), 7.92 (dd, 1H), 8.48 (d, 1H), 8.60 (s, 1H), 9.10 (d, 1H), 10.23 (s, 1H).

$[α]_D^{20}$: −59.6° (in DMSO).

Column: Chiralpak IB 5μ 150×4.6; Flow: 1.00 mL/min; Solvent: A: Hexane, B: Ethanol; Solvent mixture: 50%

Example 01.18

(2S)—N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)-3-hydroxypropanamide

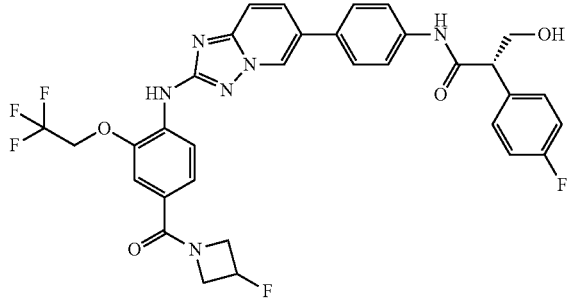 [SMILES: O=C(Nc1ccc(-c2ccc3nc(Nc4ccc(C(=O)N5CC(F)C5)cc4OCC(F)(F)F)nn3c2)cc1)[C@H](CO)c1ccc(F)cc1]

To a stirred solution of Int08.146 (290 mg) in tetrahydrofurane (18 mL) at 0° C. was added a solution of TBAF in THF (0.64 mL; c=1.0 M). The mixture was stirred at 0° C. for 30 minutes. A saturated solution of ammonium chloride was added and the reaction mixture was extracted with ethyl acetate. The organic phase was washed with saturated sodium chloride solution, dried (sodium sulfate) and the solvent was removed in vacuum. Aminophase-silica-gel chromatography gave a solid that was triturated with a mixture of dichloromethane and hexane to give 155 mg of the title compound.

$^1$H-NMR (300 MHz, DMSO-d$_6$): δ [ppm]=3.53 (dt, 1H), 3.83 (dd, 1H), 3.93-4.73 (m, 5H), 4.84-5.03 (m, 3H), 5.26-5.57 (m, 1H), 7.13 (t, 2H), 7.32-7.45 (m, 4H), 7.61-7.76 (m, 5H), 7.92 (dd, 1H), 8.27 (s, 1H), 8.33-8.41 (m, 1H), 9.10 (s, 1H), 10.25 (s, 1H).

$[\alpha]_D^{20}$: −61.7° (in DMSO).

Column: Chiralpak IC 3 µm 100×4.6; Flow: 1.00 mL/min; Solvent: A: Ethanol; Solvent mixture: 100% A. Run Time: 30 min. Retention Time: 2.63 min; UV 280 nm; Enantiomeric Ratio: 97.3%:2.7%.

Example 01.19

(2R)-2-amino-2-(4-fluorophenyl)-N-[4-(2-{[4-(methylsulfonyl)-2-(2,2,2-trifluoroethoxy)phenyl]amino}[1,2,4]triazolo[1,5-a]pyridin-6-yl)phenyl]ethanamide

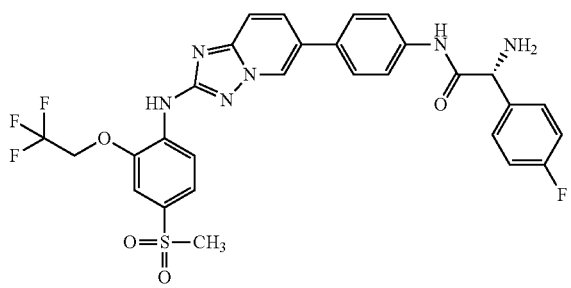 [SMILES: CS(=O)(=O)c1ccc(Nc2nc3ccc(-c4ccc(NC(=O)[C@H](N)c5ccc(F)cc5)cc4)cn3n2)c(OCC(F)(F)F)c1]

Starting with Int08.151, Example 01.19 was prepared analogously to the procedure for the preparation of Example 01.11.

$^1$H-NMR (400 MHz, DMSO-d$_6$ detected signals): δ [ppm]=3.17 (s, 3H), 4.54 (s, 1H), 5.00 (q, 2H), 7.10-7.18 (m, 2H), 7.45-7.53 (m, 2H), 7.59-7.65 (m, 2H), 7.68 (d, 1H), 7.73 (s, 4H), 7.94 (dd, 1H), 8.50 (d, 1H), 8.56 (s, 1H), 9.12 (d, 1H), 9.67-10.60 (br. s, 1H).

$[\alpha]_D^{20}$: −36.3° (in DMSO).

Example 01.20

(2R)-2-amino-2-(4-fluorophenyl)-N-[4-(2-{[2-methoxy-4-(2-oxo-1,3-oxazolidin-3-yl)phenyl]amino}[1,2,4]triazolo[1,5-a]pyridin-6-yl)phenyl]ethanamide

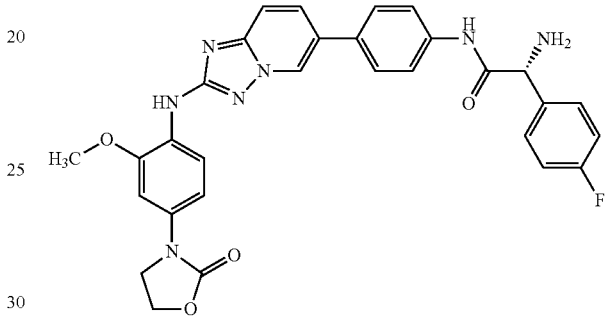

Starting with Int08.152, Example 01.20 was prepared analogously to the procedure for the preparation of Example 01.11.

$^1$H-NMR (400 MHz, DMSO-d$_6$ detected signals): δ [ppm]=3.84 (s, 3H), 4.04 (dd, 2H), 4.33-4.45 (m, 2H), 4.54 (s, 1H), 6.98 (dd, 1H), 7.08-7.18 (m, 2H), 7.39 (d, 1H), 7.45-7.52 (m, 2H), 7.57 (d, 1H), 7.67-7.77 (m, 4H), 7.86 (dd, 1H), 7.97 (s, 1H), 8.13 (d, 1H), 9.03 (d, 1H), 10.16 (br. s., 1H).

$[\alpha]_D^{20}$: −42.5° (in DMSO).

Example 01.21

(2R)-2-amino-N-{4-[2-({4-[(3-fluoroazetidin-1-yl)carbonyl]-2-methoxyphenyl}amino)[1,2,4]triazolo[1,5-a]pyridin-6-yl]phenyl}-2-(4-fluorophenyl)ethanamide

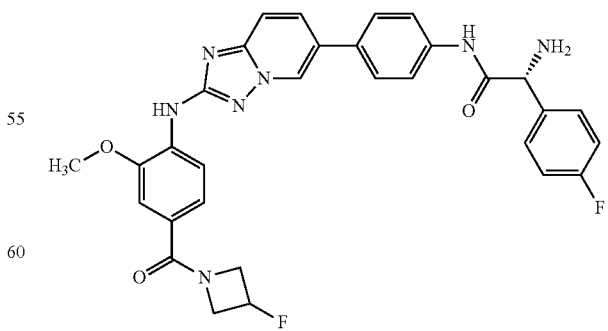

Starting with Int08.153, Example 01.21 was prepared analogously to the procedure for the preparation of Example 01.11.

$^1$H-NMR (300 MHz, DMSO-$d_6$ detected signals): δ [ppm]=3.90 (s, 3H), 4.03-4.75 (m, 5H), 5.23-5.60 (m, 1H), 7.14 (t, 2H), 7.19-7.32 (m, 2H), 7.49 (dd, 2H), 7.64 (d, 1H), 7.72 (s, 4H), 7.91 (d, 1H), 8.25-8.42 (m, 2H), 9.09 (s, 1H), 9.69-10.77 (br. s, 1H)

$[α]_D^{20}$: −38.2° (in DMSO).

Example 01.22

(2R)-2-amino-N-[4-(2-{[4-(azetidin-1-ylcarbonyl)-2-methoxyphenyl]amino}[1,2,4]triazolo[1,5-a]pyridin-6-yl)phenyl]-2-(4-fluorophenyl)ethanamide

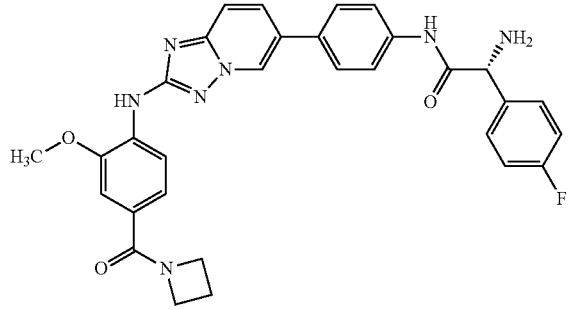 [SMILES: COc1cc(C(=O)N2CCC2)ccc1Nc1nc2ccc(-c3ccc(NC(=O)[C@H](N)c4ccc(F)cc4)cc3)cn2n1]

Starting with Int08.154, Example 01.22 was prepared analogously to the procedure for the preparation of Example 01.11.

$^1$H-NMR (300 MHz, DMSO-$d_6$ detected signals): δ [ppm]=2.23 (quin, 2H), 3.89 (s, 3H), 4.00 (br. s., 2H), 4.25-4.42 (m, 2H), 4.54 (s, 1H), 7.07-7.18 (m, 2H), 7.19-7.28 (m, 2H), 7.49 (dd, 2H), 7.63 (d, 1H), 7.72 (s, 4H), 7.90 (dd, 1H), 8.26 (s, 1H), 8.31 (d, 1H), 9.08 (d, 1H), 10.19 (br. s, 1H).

$[α]_D^{20}$: −43.8° (in DMSO).

Example 01.23

(2R)-2-amino-2-(4-fluorophenyl)-N-[4-(2-{[2-methoxy-4-(pyrrolidin-1-ylcarbonyl)phenyl]amino}[1,2,4]triazolo[1,5-a]pyridin-6-yl)phenyl]ethanamide

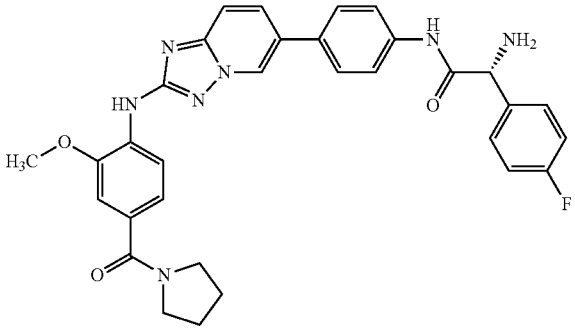

Starting with Int08.155, Example 01.23 was prepared analogously to the procedure for the preparation of Example 01.11.

$^1$H-NMR (400 MHz, DMSO-$d_6$ detected signals): δ [ppm]=1.80 (br. s., 4H), 3.45 (br. s., 4H), 3.88 (s, 3H), 4.53 (s, 1H), 7.05-7.20 (m, 4H), 7.43-7.55 (m, 2H), 7.62 (d, 1H), 7.72 (s, 4H), 7.90 (dd, 1H), 8.19 (s, 1H), 8.29 (d, 1H), 9.09 (d, 1H), 9.65-10.60 (br. s, 1H).

$[α]_D^{20}$: −40.5° (in DMSO).

Example 01.24

(2R)-2-amino-N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)ethanamide

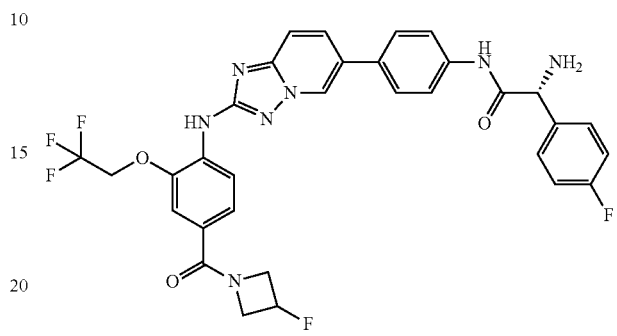

Starting with Int08.156, Example 01.24 was prepared analogously to the procedure for the preparation of Example 01.11.

$^1$H-NMR (400 MHz, DMSO-$d_6$ detected signals): δ [ppm]=3.95-4.70 (m, 5H), 4.92 (q, 2H), 5.29-5.55 (m, 1H), 7.14 (t, 2H), 7.33-7.44 (m, 2H), 7.49 (dd, 2H), 7.65 (d, 1H), 7.72 (s, 4H), 7.92 (dd, 1H), 8.25 (s, 1H), 8.37 (d, 1H), 9.10 (s, 1H), 10.17 (br. s, 1H)

$[α]_D^{20}$: −32.5° (in DMSO).

Example 01.25

(2R)-2-amino-2-(4-fluorophenyl)-N-[4-(2-{[4-(pyrrolidin-1-ylcarbonyl)-2-(2,2,2-trifluoroethoxy)phenyl]amino}[1,2,4]triazolo[1,5-a]pyridin-6-yl)phenyl]ethanamide

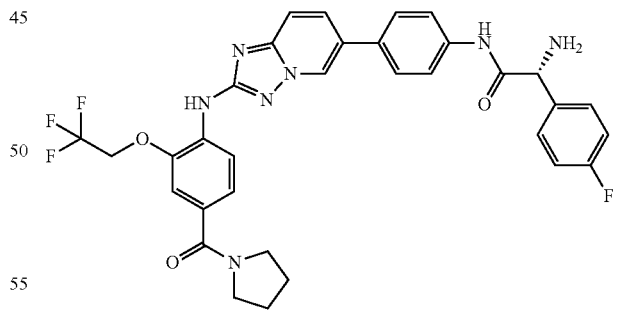

Starting with Int08.157, Example 01.25 was prepared analogously to the procedure for the preparation of Example 01.11.

$^1$H-NMR (300 MHz, DMSO-$d_6$ detected signals): δ [ppm]=1.81 (br. s, 4H), 3.44 (d, 4H), 4.53 (s, 1H), 4.89 (q, 2H), 7.14 (t, 2H), 7.22-7.34 (m, 2H), 7.49 (dd, 2H), 7.63 (d, 1H), 7.72 (s, 4H), 7.91 (dd, 1H), 8.15 (s, 1H), 8.31 (d, 1H), 9.10 (s, 1H), 10.13 (br. s, 1H).

$[α]_D^{20}$: −38.8° (in DMSO).

Example 01.26

2-(4-fluorophenyl)-N-[4-(2-{[2-methoxy-4-(methylsulfonyl)phenyl]amino}-[1,2,4]triazolo[1,5-a]pyridin-6-yl)phenyl]acetamide

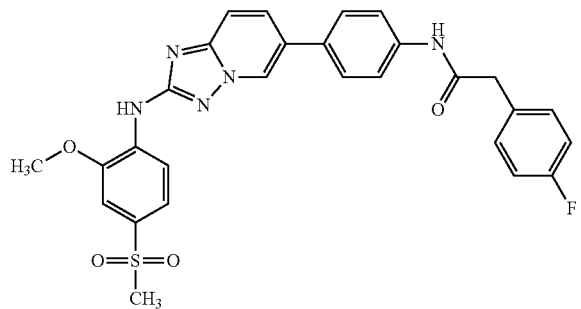 [SMILES: COc1cc(S(C)(=O)=O)ccc1Nc1nc2ccc(-c3ccc(NC(=O)Cc4ccc(F)cc4)cc3)cn2n1]

To a stirred suspension of Int21.03 (75 mg) in toluene (2.0 ml) was added Int21.05 (113 mg), (1S,3R,5R,7S)-adamantan-1-yl[(3S,5S,7S)-adamantan-1-yl]butylphosphine (8 mg), palladium acetate (2.4 mg) and potassium fluoride (27 mg) and the flask was degassed twice and backfilled with argon. The mixture was stirred for 5 minutes at r.t. Powdered potassium phosphate (90 mg) was added and the flask was degassed twice and backfilled with argon. The mixture was heated to 100° C. for 1 h. The reaction mixture was filtered through an aminophase-silica-gel column and the solvent was removed in vacuum. Aminophase-silica-gel chromatography gave 47 mg of the title compound.

$^1$H-NMR (300 MHz, DMSO-d$_6$), δ [ppm]=3.16 (3H), 3.64 (2H), 3.96 (3H), 7.08-7.18 (2H), 7.30-7.39 (2H), 7.42 (1H), 7.51 (1H), 7.64-7.77 (5H), 7.93 (1H), 8.48 (1H), 8.63 (1H), 9.12 (1H), 10.29 (1H).

Example 01.28

N-(2,4-difluorobenzyl)-4-(2-{[2-methoxy-4-(methylsulfonyl)phenyl]amino}[1,2,4]triazolo[1,5-a]pyridin-6-yl)benzamide

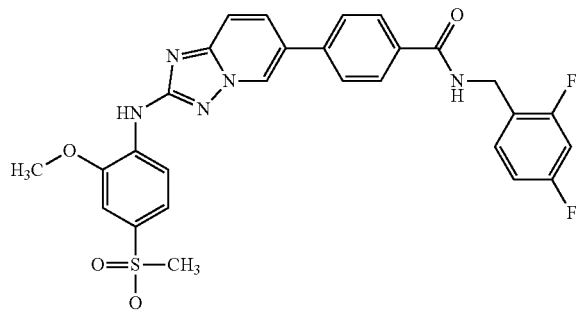

To a stirred suspension of Int21.04 (47 mg) in DMF (1 mL) was added potassium carbonate (47 mg), 2,4-Difluorbenzylamine (17 μL) and TBTU (48 mg). The mixture was stirred at room temperature for 16 h. Further 2,4-Difluorbenzylamine (17 μL) and TBTU (48 mg) were added and the mixture was stirred at room temperature for 3 h. Further 2,4-Difluorbenzylamine (17 μL) and TBTU (48 mg) were added and the mixture was stirred at room temperature for 16 h. The mixture was concentrated in vacuum. Water was added and the reaction mixture was extracted with a mixture of dichloromethane and methanol (100:1). The organic phase was dried (sodium sulfate) and the solvent was removed in vacuum. Aminophase-silica-gel chromatography gave 10 mg of the title compound as a solid.

$^1$H-NMR (400 MHz, DMSO-d$_6$): δ [ppm]=3.20 (3H), 4.00 (3H), 4.51 (2H), 7.07 (1H), 7.19-7.28 (1H), 7.40-7.49 (2H), 7.56 (1H), 7.76 (1H), 7.92-8.04 (4H), 8.07 (1H), 8.52 (1H), 8.70 (1H), 9.11 (1H), 9.32 (1H).

The following compounds were synthesized according to the methods disclosed in WO2012/143329, which is incorporated herein by reference:

N,N-diethyl-4-{[6-(4-{[(4-fluorophenyl)acetyl]amino}phenyl)[1,2,4]triazolo[1,5-a]-pyridin-2-yl]amino}-3-methoxybenzamide, N-(4-{2-[(4-cyano-2-methoxyphenyl)amino][1,2,4]triazolo[1,5-a]pyridin-6-yl}-phenyl)-2-(4-fluorophenyl)acetamide, N-(4-{2-[(2-ethoxy-4-fluorophenyl)amino][1,2,4]triazolo[1,5-a]pyridin-6-yl}phenyl)-2-(4-fluorophenyl)acetamide, N-ethyl-4-{[6-(4-{[(4-fluorophenyl)acetyl]amino}phenyl)[1,2,4]triazolo[1,5-a]pyridin-2-yl]amino}-3-methoxybenzamide, N-tert-butyl-4-{[6-(4-{[(4-fluorophenyl)acetyl]amino}phenyl)[1,2,4]triazolo[1,5-a]pyridin-2-yl]amino}-3-methoxybenzamide, 4-{[6-(4-{[(4-fluorophenyl)acetyl]amino}phenyl)[1,2,4]triazolo[1,5-a]pyridin-2-yl]amino}-N-(2-hydroxyethyl)-3-methoxybenzamide, N-(2-ethoxyethyl)-4-{[6-(4-{[(4-fluorophenyl)acetyl]amino}phenyl)[1,2,4]triazolo-[1,5-a]pyridin-2-yl]amino}-3-methoxybenzamide, 3-ethoxy-4-{[6-(4-{[(4-fluorophenyl)acetyl]amino}phenyl)[1,2,4]triazolo[1,5-a]pyridin-2-yl]amino}-N-(2-hydroxyethyl)benzamide, 3-ethoxy-4-{[6-(4-{[(4-fluorophenyl)acetyl]amino}phenyl)[1,2,4]triazolo[1,5-a]pyridin-2-yl]amino}-N-(1-hydroxy-2-methylpropan-2-yl)benzamide, 3-ethoxy-N,N-diethyl-4-{[6-(4-{[(4-fluorophenyl)acetyl]amino}phenyl)[1,2,4]triazolo-[1,5-a]pyridin-2-yl]amino}benzamide, 4-{[6-(4-{[(4-fluorophenyl)acetyl]amino}phenyl)[1,2,4]triazolo[1,5-a]pyridin-2-yl]-amino}-N-(2-hydroxyethyl)-3-(2,2,2-trifluoroethoxy)benzamide, 4-{[6-(4-{[(4-fluorophenyl)acetyl]amino}phenyl)[1,2,4]triazolo[1,5-a]pyridin-2-yl]amino}-N-(2-hydroxy-2-methylpropyl)-3-methoxybenzamide, 4-{[6-(4-{[(4-fluorophenyl)acetyl]amino}phenyl)[1,2,4]triazolo[1,5-a]pyridin-2-yl]amino}-N-(1-hydroxy-2-methylpropan-2-yl)-3-methoxybenzamide, N-{2-[acetyl(methyl)amino]ethyl}-4-{[6-(4-{[(4-fluorophenyl)acetyl]amino}phenyl)-[1,2,4]triazolo[1,5-a]pyridin-2-yl]amino}-3-methoxy-N-methylbenzamide, 2-(4-fluorophenyl)-N-[4-(2-{[2-methoxy-4-(methylsulfonyl)phenyl]amino}[1,2,4]-triazolo[1,5-a]pyridin-6-yl)phenyl]acetamide, 3-ethoxy-N-ethyl-4-{[6-(4-{[(4-fluorophenyl)acetyl]amino}phenyl)[1,2,4]triazolo[1,5-a]pyridin-2-yl]amino}benzamide, 3-ethoxy-4-{[6-(4-{[(4-fluorophenyl)acetyl]amino}phenyl)[1,2,4]triazolo[1,5-a]pyridin-2-yl]amino}-N-(2-hydroxy-2-methylpropyl)benzamide, 3-ethoxy-N-ethyl-4-{[6-(4-{[(4-fluorophenyl)acetyl]amino}phenyl)[1,2,4]triazolo[1,5-a]pyridin-2-yl]amino}-N-(2-methoxyethyl)benzamide, 3-ethoxy-4-{[6-(4-{[(4-fluorophenyl)acetyl]amino}phenyl)[1,2,4]triazolo[1,5-a]pyridin-2-yl]amino}-N-(2-hydroxyethyl)-N-methylbenzamide, 4-{[6-(4-{[(4-fluorophenyl)acetyl]amino}phenyl)[1,2,4]triazolo[1,5-a]pyridin-2-yl]-amino}-3-methoxy-N-methyl-N-[2-(methylamino)ethyl]benzamide, N-tert-butyl-4-{[6-(4-{[(4-fluorophenyl)acetyl]amino}phenyl)[1,2,4]triazolo[1,5-a]pyridin-2-yl]amino}-3-(2,2,2-trifluoroethoxy)benzamide, N,N-diethyl-4-{[6-(4-{[(4-fluorophenyl)acetyl]amino}phenyl)[1,2,4]triazolo[1,5-a]pyridin-2-yl]amino}-3-(2,2,2-trifluoroethoxy)benzamide, N,N-diethyl-4-{[6-(4-{[(4-fluorophenyl)acetyl]amino}phenyl)[1,2,4]triazolo[1,5-a]pyridin-2-yl]amino}-3-propoxybenzamide, 3-(cyclopropylmethoxy)-N,N-diethyl-4-{[6-(4-{[(4-fluorophenyl)acetyl]amino}-phenyl)[1,2,4]triazolo[1,5-a]pyridin-2-yl]amino}benzamide, N,N-diethyl-4-{[6-(4-{[(4-fluorophenyl)acetyl]amino}phenyl)[1,2,4]triazolo[1,5-a]pyridin-2-yl]amino}-3-isopropoxybenzamide, N,N-diethyl-4-{[6-(4-{[(4-fluorophenyl)acetyl]amino}phenyl)[1,2,4]triazolo[1,5-a]pyridin-2-yl]amino}-3-(2-methoxyethoxy)benzamide, 4-{[6-(4-{[(4-fluorophenyl)acetyl]amino}phenyl)[1,2,4]triazolo[1,5-a]pyridin-2-yl]-amino}-3-(2,2,2-trifluoroethoxy)-N-(2,2,2-trifluoroethyl)benzamide, 3-ethoxy-4-{[6-(4-{[(4-fluorophenyl)acetyl]amino}phenyl)[1,2,4]triazolo[1,5-a]pyridin-2-yl]amino}-N-[2-(methylsulfonyl)ethyl]benzamide, 4-{[6-(4-{[(4-fluorophenyl)acetyl]amino}phenyl)[1,2,4]triazolo[1,5-a]pyridin-2-yl]amino}-N-(2-hydroxy-2-methylpropyl)-3-(2,2,2-trifluoroethoxy)benzamide, 4-{[6-(4-{[(4-fluorophenyl)acetyl]amino}phenyl)[1,2,4]triazolo[1,5-a]pyridin-2-yl]amino}-3-methoxy-N-methylbenzamide, 4-[(6-{4-[(4-fluorobenzyl)carbamoyl]phenyl}[1,2,4]triazolo[1,5-a]pyridin-2-yl)-amino-N-(2-hydroxyethyl)-3-methoxybenzamide, 3-ethoxy-4-[(6-{4-[(4-fluorobenzyl)carbamoyl]phenyl}[1,2,4]triazolo[1,5-a]pyridin-2-yl)amino]-N-(2-hydroxyethyl)benzamide, 3-ethoxy-4-[(6-{4-[(4-fluorobenzyl)carbamoyl]phenyl}[1,2,4]triazolo[1,5-a]pyridin-2-yl)amino]-N-(1-hydroxy-2-methylpropan-2-yl)benzamide, 4-[(6-{4-[(4-fluorobenzyl)carbamoyl]phenyl}[1,2,4]triazolo[1,5-a]pyridin-2-yl)-amino]-N-(2-hydroxyethyl)-3-(2,2,2-trifluoroethoxy)benzamide, 4-[(6-{4-[(4-fluorobenzyl)carbamoyl]phenyl}[1,2,4]triazolo[1,5-a]pyridin-2-yl)-amino]-N-(2-hydroxy-2-methylpropyl)-3-methoxybenzamide, N-(4-fluorobenzyl)-4-(2-{[2-methoxy-4-(methylsulfonyl)phenyl]amino}[1,2,4]-triazolo[1,5-a]pyridin-6-yl)benzamide, 3-ethoxy-4-[(6-{4-[(4-fluorobenzyl)carbamoyl]phenyl}[1,2,4]triazolo[1,5-a]pyridin-2-yl)amino]-N-(2-hydroxy-2-methylpropyl)benzamide, 4-[(6-{4-[(4-fluorobenzyl)carbamoyl]phenyl}[1,2,4]triazolo[1,5-a]pyridin-2-yl)-amino]-N-(1-hydroxy-2-methylpropan-2-yl)-3-methoxybenzamide, N-{2-[acetyl(methyl)amino]ethyl}-4-[(6-{4-[(4-fluorobenzyl)carbamoyl]phenyl}-[1,2,4]triazolo[1,5-a]pyridin-2-yl)amino]-3-methoxy-N-methylbenzamide, N-(2-ethoxyethyl)-4-[(6-{4-[(4-fluorobenzyl)carbamoyl]phenyl}[1,2,4]triazolo[1,5-a]pyridin-2-yl)amino]-3-methoxybenzamide, 4-[(6-{4-[(4-fluorobenzyl)carbamoyl]phenyl}[1,2,4]triazolo[1,5-a]pyridin-2-yl)-amino]-3-methoxy-N-methyl-N-[2-(methylamino)ethyl]benzamide, 3-ethoxy-4-[(6-{4-[(4-fluorobenzyl)carbamoyl]phenyl}[1,2,4]triazolo[1,5-a]pyridin-2-yl)amino]-N-(2-hydroxyethyl)-N-methylbenzamide, 4-[(6-{4-[(4-fluorobenzyl)carbamoyl]phenyl}[1,2,4]triazolo[1,5-a]pyridin-2-yl)-amino]-3-methoxy-N-methylbenzamide, N-tert-butyl-4-[(6-{4-[(4-fluorobenzyl)carbamoyl]phenyl}[1,2,4]triazolo[1,5-a]-pyridin-2-yl)amino]-3-methoxybenzamide, 4-[(6-{4-[(4-fluorobenzyl)carbamoyl]phenyl}[1,2,4]triazolo[1,5-a]pyridin-2-yl)-amino]-3-methoxy-N-[2-(methylsulfonyl)ethyl]benzamide, 4-{2-[(2,4-dimethoxyphenyl)amino][1,2,4]triazolo[1,5-a]pyridin-6-yl}-N-(4-fluoro-benzyl)benzamide, 4-[(6-{4-[(4-fluorobenzyl)carbamoyl]phenyl}[1,2,4]triazolo[1,5-a]pyridin-2-yl)-amino]-3-methoxy-N-(2,2,2-trifluoroethyl)benzamide, 4-[(6-{4-[(4-fluorobenzyl)carbamoyl]phenyl}[1,2,4]triazolo[1,5-a]pyridin-2-yl)-amino]-N-(1-hydroxy-2-methylpropan-2-yl)-3-(2,2,2-trifluoroethoxy)benzamide, 3-ethoxy-4-[(6-{4-[(4-fluorobenzyl)carbamoyl]phenyl}[1,2,4]triazolo[1,5-a]pyridin-2-yl)amino]-N-[2-(methylsulfonyl)ethyl]benzamide, N-ethyl-4-[(6-{4-[(4-fluorobenzyl)carbamoyl]phenyl}[1,2,4]triazolo[1,5-a]pyridin-2-yl)amino]-3-methoxybenzamide, N-tert-butyl-3-ethoxy-4-[(6-{4-[(4-fluorobenzyl)carbamoyl]phenyl}[1,2,4]-triazolo[1,5-a]pyridin-2-yl)amino]benzamide, 4-[(6-{4-[(4-fluorobenzyl)carbamoyl]phenyl}[1,2,4]triazolo[1,5-a]pyridin-2-yl)-amino]-N-(2-hydroxy-2-methylpropyl)-3-(2,2,2-trifluoroethoxy)benzamide, 4-[(6-{4-[(4-fluorobenzyl)carbamoyl]phenyl}[1,2,4]triazolo[1,5-a]pyridin-2-yl)-amino]-3-(2,2,2-trifluoroethoxy)-N-(2,2,2-trifluoroethyl)benzamide, 4-(2-{[4-(dimethylamino)-2-methylphenyl]amino}[1,2,4]triazolo[1,5-a]pyridin-6-yl)-N-(4-fluorobenzyl)benzamide, 2-fluoro-N-(4-fluorobenzyl)-4-[2-({4-[(1-hydroxy-2-methylpropan-2-yl)carbamoyl]-2-methoxyphenyl}amino)[1,2,4]triazolo[1,5-a]pyridin-6-yl]benzamide, N-(4-fluorobenzyl)-4-[2-({4-[(1-hydroxy-2-methylpropan-2-yl)carbamoyl]-2-methoxyphenyl}amino)[1,2,4]triazolo[1,5-a]pyridin-6-yl]-2-methylbenzamide, 2-chloro-N-(4-fluorobenzyl)-4-[2-({4-[(1-hydroxy-2-methylpropan-2-yl)carbamoyl]-2-methoxyphenyl}amino)[1,2,4]triazolo[1,5-a]pyridin-6-yl]benzamide, 4-[(6-{4-[(cyclopropylmethyl)carbamoyl]phenyl}[1,2,4]triazolo[1,5-a]pyridin-2-yl)-amino]-3-ethoxy-N-ethylbenzamide, 4-[(6-{4-[(cyclopropylmethyl)carbamoyl]phenyl}[1,2,4]triazolo[1,5-a]pyridin-2-yl)-amino]-3-ethoxy-N-ethyl-N-(2-methoxyethyl)benzamide, 4-[(6-{4-[(cyclopropylmethyl)carbamoyl]phenyl}[1,2,4]triazolo[1,5-a]pyridin-2-yl)-amino]-3-ethoxy-N-(2-hydroxyethyl)benzamide, 4-[(6-{4-[(cyclopropylmethyl)carbamoyl]phenyl}[1,2,4]triazolo[1,5-a]pyridin-2-yl)amino]-N-(2-hydroxyethyl)-3-(2,2,2-trifluoroethoxy)benzamide, 4-[(6-{4-[(cyclopropylmethyl)carbamoyl]phenyl}[1,2,4]triazolo[1,5-a]pyridin-2-yl)-amino]-N-ethyl-3-(2,2,2-trifluoroethoxy)benzamide, N-ethyl-4-[(6-{4-[(3-fluorobenzyl)carbamoyl]phenyl}[1,2,4]triazolo[1,5-a]pyridin-2-yl)amino]-3-methoxybenzamide, N-(4-fluorobenzyl)-4-[2-({4-[(1-hydroxy-2-methylpropan-2-yl)carbamoyl]-2-methoxyphenyl}amino)[1,2,4]triazolo[1,5-a]pyridin-6-yl]-2-methoxybenzamide, 4-{[6-(4-{[(4-fluorophenyl)acetyl]amino}phenyl)[1,2,4]triazolo[1,5-a]pyridin-2-yl]-amino}-3-methoxy-N-(2,2,2-trifluoroethyl)benzamide, N-[4-(2-{[2-ethoxy-4-(methylsulfonyl)phenyl]amino}[1,2,4]triazolo[1,5-a]pyridin-6-yl)phenyl]-2-(4-fluorophenyl)acetamide, N-[4-(2-{[2-ethoxy-4-(ethylsulfonyl)phenyl]amino}[1,2,4]triazolo[1,5-a]pyridin-6-yl)phenyl]-2-(4-fluorophenyl)acetamide, 2-(4-fluorophenyl)-N-[4-(2-{[4-(methylsulfonyl)-2-(2,2,2-trifluoroethoxy)phenyl]-amino}[1,2,4]triazolo[1,5-a]pyridin-6-yl)phenyl]acetamide, N-[4-(2-{[2-(difluoromethoxy)-4-(methylsulfonyl)phenyl]amino}[1,2,4]triazolo[1,5-a]pyridin-6-yl)phenyl]-2-(4-fluorophenyl)acetamide, N-[4-(2-{[2-(difluoromethoxy)-4-(ethylsulfonyl)phenyl]amino}[1,2,4]triazolo[1,5-a]pyridin-6-yl)phenyl]-2-(4-fluorophenyl)acetamide, N-[4-(2-{[2-(cyclopropyloxy)-4-(methylsulfonyl)phenyl]amino}[1,2,4]triazolo[1,5-a]-pyridin-6-yl)phenyl]-2-(4-fluorophenyl)acetamide, 4-(2-{[2-ethoxy-4-(methylsulfonyl)phenyl]amino}[1,2,4]triazolo[1,5-a]pyridin-6-yl)-N-(4-fluorobenzyl)benzamide, 4-(2-{[2-ethoxy-4-(ethylsulfonyl)phenyl]amino}[1,2,4]triazolo[1,5-a]pyridin-6-yl)-N-(4-fluorobenzyl)benzamide, N-(4-fluorobenzyl)-4-(2-{[4-(methylsulfonyl)-2-(2,2,2-trifluoroethoxy)phenyl]amino}-[1,2,4]triazolo[1,5-a]pyridin-6-yl)benzamide, 4-(2-{[2-(difluoromethoxy)-4-(methylsulfonyl)phenyl]amino}[1,2,4]triazolo[1,5-a]-pyridin-6-yl)-N-(4-fluorobenzyl)benzamide, 4-(2-{[2-(cyclopropyloxy)-4-(methylsulfonyl)phenyl]amino}[1,2,4]triazolo[1,5-a]-pyridin-6-yl)-N-(4-fluorobenzyl)benzamide, N-(4-fluorobenzyl)-2-methyl-4-(2-{[4-(methylsulfonyl)-2-(2,2,2-trifluoroethoxy)-phenyl]amino}[1,2,4]triazolo[1,5-a]pyridin-6-yl)benzamide, N-(4-fluorobenzyl)-2-methoxy-4-(2-{[2-methoxy-4-(methylsulfonyl)phenyl]amino}-[1,2,4]triazolo[1,5-a]pyridin-6-yl)benzamide, 2-(2,4-difluorophenyl)-N-[4-(2-{[2-methoxy-4-(methylsulfonyl)phenyl]amino}-[1,2,4]triazolo[1,5-a]pyridin-6-yl)phenyl]acetamide, N-(2,4-difluorobenzyl)-4-(2-{[2-methoxy-4-(methylsulfonyl)phenyl]amino}-[1,2,4]triazolo[1,5-a]pyridin-6-yl)benzamide, 4-{[6-(4-{[(4-fluorophenyl)acetyl]amino}phenyl)[1,2,4]triazolo[1,5-a]pyridin-2-yl]amino}-3-methoxy-N-(2-methoxyethyl)benzamide, 4-{[6-(4-{[(4-fluorophenyl)acetyl]amino}phenyl)[1,2,4]triazolo[1,5-a]pyridin-2-yl]amino}-3-methoxy-N,N-dimethylbenzamide, 4-{[6-(4-{[(4-fluorophenyl)acetyl]amino}phenyl)[1,2,4]triazolo[1,5-a]pyridin-2-yl]amino}-3-methoxy-N-[2-(methylsulfonyl)ethyl]benzamide, 4-{[6-(4-{[(4-fluorophenyl)acetyl]amino}phenyl)[1,2,4]triazolo[1,5-a]pyridin-2-yl]amino}-3-methoxybenzamide, N-(2-fluoroethyl)-4-{[6-(4-{[(4-fluorophenyl)acetyl]amino}phenyl)[1,2,4]-triazolo[1,5-a]pyridin-2-yl]amino}-3-methoxybenzamide, N-ethyl-4-{[6-(4-{[(4-fluorophenyl)acetyl]amino}phenyl)[1,2,4]triazolo[1,5-a]-pyridin-2-yl]amino}-3-methoxy-N-methylbenzamide, N-(2,2-difluoroethyl)-4-{[6-(4-{[(4-fluorophenyl)acetyl]amino}phenyl)[1,2,4]-triazolo[1,5-a]pyridin-2-yl]amino}-3-methoxybenzamide, N-[2-(dimethylamino)ethyl]-4-{[6-(4-{[(4-fluorophenyl)acetyl]amino}phenyl)[1,2,4]-triazolo[1,5-a]pyridin-2-yl]amino}-3-methoxy-N-methylbenzamide, 4-{[6-(4-{[(4-fluorophenyl)acetyl]amino}phenyl)[1,2,4]triazolo[1,5-a]pyridin-2-yl]-amino}-3-methoxy-N-methyl-N-(2,2,2-trifluoroethyl)benzamide, N-[2-(dimethylamino)ethyl]-4-{[6-(4-{[(4-fluorophenyl)acetyl]amino}phenyl)-[1,2,4]triazolo[1,5-a]pyridin-2-yl]amino}-3-methoxybenzamide, 4-{[6-(4-{[(4-fluorophenyl)acetyl]amino}phenyl)[1,2,4]triazolo[1,5-a]pyridin-2-yl]amino}-N-(3-fluoropropyl)-3-methoxybenzamide, N-[4-(2-{[5-fluoro-2-methoxy-4-(methylsulfonyl)phenyl]amino}[1,2,4]triazolo[1,5-a]pyridin-6-yl)phenyl]-2-(4-fluorophenyl)acetamide, 2-(4-fluorophenyl)-N-[4-(2-{[2-methoxy-4-(methylsulfinyl)phenyl]amino}[1,2,4]-triazolo[1,5-a]pyridin-6-yl)phenyl]acetamide, N-[4-(2-{[5-fluoro-2-methoxy-4-(methylsulfinyl)phenyl]amino}[1,2,4]triazolo[1,5-a]pyridin-6-yl)phenyl]-2-(4-fluorophenyl)acetamide, N-[4-(2-{[4-(tert-butylsulfamoyl)-2-methoxyphenyl]amino}[1,2,4]triazolo[1,5-a]-pyridin-6-yl)phenyl]-2-(4-fluorophenyl)acetamide, 2-(4-fluorophenyl)-N-[4-(2-{[4-(2-hydroxypropan-2-yl)-2-methoxyphenyl]amino}-[1,2,4]triazolo[1,5-a]pyridin-6-yl)phenyl]acetamide, N-(4-{2-[(2,4-dimethoxyphenyl)amino][1,2,4]triazolo[1,5-a]pyridin-6-yl}phenyl)-2-(4-fluorophenyl)acetamide, 3-ethoxy-N-ethyl-4-{[6-(4-{[(4-fluorophenyl)acetyl]amino}phenyl)[1,2,4]triazolo-[1,5-a]pyridin-2-yl]amino}-N-methylbenzamide, N-[2-(dimethylamino)ethyl]-3-ethoxy-4-{[6-(4-{[(4-fluorophenyl)acetyl]amino}-phenyl)[1,2,4]triazolo[1,5-a]pyridin-2-yl]amino}benzamide, 4-{[6-(4-{[(4-fluorophenyl)acetyl]amino}phenyl)[1,2,4]triazolo[1,5-a]pyridin-2-yl]-amino}-N-[2-(methylsulfonyl)ethyl]-3-(2,2,2-trifluoroethoxy)benzamide, 4-{[6-(4-{[(4-fluorophenyl)acetyl]amino}phenyl)[1,2,4]triazolo[1,5-a]pyridin-2-yl]amino}-N-(1-hydroxy-2-methylpropan-2-yl)-3-(2,2,2-trifluoroethoxy)benzamide, N-[2-(dimethylamino)ethyl]-4-{[6-(4-{[(4-fluorophenyl)acetyl]amino}phenyl)-[1,2,4]triazolo[1,5-a]pyridin-2-yl]amino}-3-(2,2,2-trifluoroethoxy)benzamide, 2-(4-fluorophenyl)-N-[4-(2-{[4-(methylsulfinyl)-2-(2,2,2-trifluoroethoxy)phenyl]-amino}[1,2,4]triazolo[1,5-a]pyridin-6-yl)phenyl]acetamide, 4-{[6-(4-{[(4-fluorophenyl)acetyl]amino}phenyl)[1,2,4]triazolo[1,5-a]pyridin-2-yl]amino}-3-(trifluoromethoxy)benzamide, N-[4-(2-{[2-(difluoromethoxy)-4-(propan-2-ylsulfonyl)phenyl]amino}[1,2,4]triazolo[1,5-a]pyridin-6-yl)phenyl]-2-(4-fluorophenyl)acetamide, N-[4-(2-{[2-(difluoromethoxy)-4-fluorophenyl]amino}[1,2,4]triazolo[1,5-a]pyridin-6-yl)phenyl]-2-(4-fluorophenyl)acetamide, 4-{[6-(4-{[(4-fluorophenyl)acetyl]amino}phenyl)[1,2,4]triazolo[1,5-a]pyridin-2-yl]amino}-3-methylbenzamide, 4-{[6-(4-{[(4-fluorophenyl)acetyl]amino}phenyl)[1,2,4]triazolo[1,5-a]pyridin-2-yl]amino}-3-methyl-N-(2,2,2-trifluoroethyl)benzamide, N-(2-fluoroethyl)-4-{[6-(4-{[(4-fluorophenyl)acetyl]amino}phenyl)[1,2,4]-triazolo[1,5-a]pyridin-2-yl]amino}-3-methylbenzamide, 4-{[6-(4-{[(4-fluorophenyl)acetyl]amino}phenyl)[1,2,4]triazolo[1,5-a]pyridin-2-yl]amino}-N,N,3-trimethylbenzamide, 2-(4-fluorophenyl)-N-[4-(2-{[2-methyl-4-(methylsulfonyl)phenyl]amino}[1,2,4]-triazolo[1,5-a]pyridin-6-yl)phenyl]acetamide, 2-(4-fluorophenyl)-N-[4-(2-{[2-methyl-4-(methylsulfinyl)phenyl]amino}[1,2,4]-triazolo[1,5-a]pyridin-6-yl)phenyl]acetamide, 2-(4-fluorophenyl)-N-{4-[2-({2-methyl-4-[(methylsulfonyl)amino]phenyl}amino)-[1,2,4]triazolo[1,5-a]pyridin-6-yl]phenyl}acetamide, 2-(4-fluorophenyl)-N-(4-{2-[(4-methoxy-2-methylphenyl)amino][1,2,4]triazolo[1,5-a]pyridin-6-yl}phenyl)acetamide, N-[4-(2-{[4-(dimethylamino)-2-methylphenyl]amino}[1,2,4]triazolo[1,5-a]pyridin-6-yl)phenyl]-2-(4-fluorophenyl)acetamide, N-ethyl-5-{[6-(4-{[(4-fluorophenyl)acetyl]amino}phenyl)[1,2,4]triazolo[1,5-a]pyridin-2-yl]amino}-4-methylpyridine-2-carboxamide, 5-{[6-(4-{[(4-fluorophenyl)acetyl]amino}phenyl)[1,2,4]triazolo[1,5-a]pyridin-2-yl]amino}-4-methyl-N-(2,2,2-trifluoroethyl)pyridine-2-carboxamide, N-[4-(2-{[2-fluoro-4-(methylsulfonyl)phenyl]amino}[1,2,4]triazolo[1,5-a]pyridin-6-yl)phenyl]-2-(4-fluorophenyl)acetamide, 2-(4-fluoro-3-methylphenyl)-N-[4-(2-{[2-methoxy-4-(methylsulfonyl)phenyl]-amino}[1,2,4]triazolo[1,5-a]pyridin-6-yl)phenyl]acetamide, 2-(4-chlorophenyl)-N-[4-(2-{[2-methoxy-4-(methylsulfonyl)phenyl]amino}-[1,2,4]triazolo[1,5-a]pyridin-6-yl)phenyl]acetamide, N-[4-(2-{[2-methoxy-4-(methylsulfonyl)phenyl]amino}[1,2,4]triazolo[1,5-a]pyridin-6-yl)phenyl]-2-phenylacetamide, 4-[(6-{4-[(4-fluorobenzyl)carbamoyl]phenyl}[1,2,4]triazolo[1,5-a]pyridin-2-yl)-amino]-3-methoxybenzamide, 4-[(6-{4-[(4-fluorobenzyl)carbamoyl]phenyl}[1,2,4]triazolo[1,5-a]pyridin-2-yl)-amino]-3-methoxy-N-(2-methoxyethyl)benzamide, 4-[(6-{4-[(4-fluorobenzyl)carbamoyl]phenyl}[1,2,4]triazolo[1,5-a]pyridin-2-yl)-amino]-N-(2-fluoroethyl)-3-methoxybenzamide, 4-[(6-{4-[(4-fluorobenzyl)carbamoyl]phenyl}[1,2,4]triazolo[1,5-a]pyridin-2-yl)-amino]-3-methoxy-N,N-dimethylbenzamide, N-(2,2-difluoroethyl)-4-[(6-{4-[(4-fluorobenzyl)carbamoyl]phenyl}[1,2,4]-triazolo[1,5-a]pyridin-2-yl)amino]-3-methoxybenzamide, N-[2-(dimethylamino)ethyl]-4-[(6-{4-[(4-fluorobenzyl)carbamoyl]phenyl}-[1,2,4]triazolo[1,5-a]pyridin-2-yl)amino]-3-methoxybenzamide, N-[2-(dimethylamino)ethyl]-4-[(6-{4-[(4-fluorobenzyl)carbamoyl]phenyl}-[1,2,4]triazolo[1,5-a]pyridin-2-yl)amino]-3-methoxy-N-methylbenzamide, 4-[(6-{4-[(4-fluorobenzyl)carbamoyl]phenyl}[1,2,4]triazolo[1,5-a]pyridin-2-yl)-amino]-N-(3-fluoropropyl)-3-methoxybenzamide, N-(4-fluorobenzyl)-4-(2-{[2-methoxy-4-(methylsulfinyl)phenyl]amino}[1,2,4]-triazolo[1,5-a]pyridin-6-yl)benzamide, 4-(2-{[4-(tert-butylsulfamoyl)-2-methoxyphenyl]amino}[1,2,4]triazolo[1,5-a]-pyridin-6-yl)-N-(4-fluorobenzyl)benzamide, N-(4-fluorobenzyl)-4-(2-{[4-(2-hydroxypropan-2-yl)-2-methoxyphenyl]amino}-[1,2,4]triazolo[1,5-a]pyridin-6-yl)benzamide, N-[2-(dimethylamino)ethyl]-3-ethoxy-4-[(6-{4-[(4-fluorobenzyl)carbamoyl]-phenyl}[1,2,4]triazolo[1,5-a]pyridin-2-yl)amino]benzamide, 3-ethoxy-N-ethyl-4-[(6-{4-[(4-fluorobenzyl)carbamoyl]phenyl}[1,2,4]triazolo[1,5-a]pyridin-2-yl)amino]-N-methylbenzamide, 3-ethoxy-4-[(6-{4-[(4-fluorobenzyl)carbamoyl]phenyl}[1,2,4]triazolo[1,5-a]pyridin-2-yl)amino]-N-(2-fluoroethyl)benzamide, N-[2-(dimethylamino)ethyl]-4-[(6-{4-[(4-fluorobenzyl)carbamoyl]phenyl}-[1,2,4]triazolo[1,5-a]pyridin-2-yl)amino]-3-(2,2,2-trifluoroethoxy)benzamide, 4-[(6-{4-[(4-fluorobenzyl)carbamoyl]phenyl}[1,2,4]triazolo[1,5-a]pyridin-2-yl)-amino]-N-(2-fluoroethyl)-3-(2,2,2-trifluoroethoxy)benzamide, 4-[(6-{4-[(4-fluorobenzyl)carbamoyl]phenyl}[1,2,4]triazolo[1,5-a]pyridin-2-yl)-amino]-3-(trifluoromethoxy)benzamide, 4-(2-{[2-(difluoromethoxy)-4-(ethylsulfonyl)phenyl]amino}[1,2,4]triazolo[1,5-a]-pyridin-6-yl)-N-(4-fluorobenzyl)benzamide, 4-(2-{[2-(difluoromethoxy)-4-(propan-2-ylsulfonyl)phenyl]amino}[1,2,4]triazolo[1,5-a]pyridin-6-yl)-N-(4-fluorobenzyl)benzamide, 4-(2-{[2-(difluoromethoxy)-4-fluorophenyl]amino}[1,2,4]triazolo[1,5-a]pyridin-6-yl)-N-(4-fluorobenzyl)benzamide, N-ethyl-4-[(6-{4-[(4-fluorobenzyl)carbamoyl]phenyl}[1,2,4]triazolo[1,5-a]pyridin-2-yl)amino]-3-methylbenzamide, 4-[(6-{4-[(4-fluorobenzyl)carbamoyl]phenyl}[1,2,4]triazolo[1,5-a]pyridin-2-yl)-amino]-3-methylbenzamide, 4-[(6-{4-[(4-fluorobenzyl)carbamoyl]phenyl}[1,2,4]triazolo[1,5-a]pyridin-2-yl)-amino]-3-methyl-N-(2,2,2-trifluoroethyl)benzamide, 4-[(6-{4-[(4-fluorobenzyl)carbamoyl]phenyl}[1,2,4]triazolo[1,5-a]pyridin-2-yl)-amino]-N-(2-fluoroethyl)-3-methylbenzamide, N-(4-fluorobenzyl)-4-(2-{[2-methyl-4-(methylsulfonyl)phenyl]amino}[1,2,4]-triazolo[1,5-a]pyridin-6-yl)benzamide, N-(4-fluorobenzyl)-4-(2-{[2-methyl-4-(methylsulfinyl)phenyl]amino}[1,2,4]-triazolo[1,5-a]pyridin-6-yl)benzamide, N-(4-fluorobenzyl)-4-[2-({2-methyl-4-[(methylsulfonyl)amino]phenyl}amino)[1,2,4]-triazolo[1,5-a]pyridin-6-yl]benzamide, N-(4-fluorobenzyl)-4-{2-[(4-methoxy-2-methylphenyl)amino][1,2,4]triazolo[1,5-a]pyridin-6-yl}benzamide, 4-[(6-{4-[(4-chlorobenzyl)carbamoyl]phenyl}[1,2,4]triazolo[1,5-a]pyridin-2-yl)-amino]-3-methoxy-N-(2,2,2-trifluoroethyl)benzamide, N-(4-chlorobenzyl)-4-(2-{[2-methoxy-4-(methylsulfonyl)phenyl]amino}[1,2,4]-triazolo[1,5-a]pyridin-6-yl)benzamide, N-(4-chlorobenzyl)-4-(2-{[2-methyl-4-(methylsulfonyl)phenyl]amino}[1,2,4]-triazolo[1,5-a]pyridin-6-yl)benzamide, N-(4-chlorobenzyl)-4-(2-{[2-methyl-4-(methylsulfinyl)phenyl]amino}[1,2,4]-triazolo[1,5-a]pyridin-6-yl)benzamide, 4-(2-{[2-methoxy-4-(methylsulfonyl)phenyl]amino}[1,2,4]triazolo[1,5-a]pyridin-6-yl)-N-(4-methylbenzyl)benzamide, N-(4-methylbenzyl)-4-(2-{[2-methyl-4-(methylsulfonyl)phenyl]amino}[1,2,4]-triazolo[1,5-a]pyridin-6-yl)benzamide, N-(4-methylbenzyl)-4-(2-{[2-methyl-4-(methylsulfinyl)phenyl]amino}[1,2,4]-triazolo[1,5-a]pyridin-6-yl)benzamide, 4-[(6-{4-[(2,4-difluorobenzyl)carbamoyl]phenyl}[1,2,4]triazolo[1,5-a]pyridin-2-yl)-amino]-3-methoxy-N-(2,2,2-trifluoroethyl)benzamide, N-(2,4-difluorobenzyl)-2-methyl-4-(2-{[4-(methylsulfonyl)-2-(2,2,2-trifluoroethoxy)-phenyl]amino}[1,2,4]triazolo[1,5-a]pyridin-6-yl)benzamide, N-(4-fluorobenzyl)-4-(2-{[4-(2-hydroxypropan-2-yl)-2-methoxyphenyl]amino}-[1,2,4]triazolo[1,5-a]pyridin-6-yl)-2-methoxybenzamide, 2-(4-fluorophenyl)-N-[4-(2-{[2-methoxy-4-(S-methylsulfonimidoyl)phenyl]amino}-[1,2,4]triazolo[1,5-a]pyridin-6-yl)phenyl]acetamide, N-(4-fluorobenzyl)-4-(2-{[2-methoxy-4-(S-methylsulfonimidoyl)phenyl]amino}-[1,2,4]triazolo[1,5-a]pyridin-6-yl)benzamide, 2-(4-fluorophenyl)-N-[4-(2-{[4-(hydroxymethyl)-2-methoxyphenyl]amino}[1,2,4]-triazolo[1,5-a]pyridin-6-yl)phenyl]acetamide, N-(4-fluorobenzyl)-4-(2-{[4-(hydroxymethyl)-2-methoxyphenyl]amino}[1,2,4]-triazolo[1,5-a]pyridin-6-yl)benzamide.

Biological Assay: Proliferation Assay

Cultivated tumor cells (MCF7, hormone dependent human mammary carcinoma cells, ATCC HTB22; NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multi-drug-resistant human cervical carcinoma cells, EPO-GmbH, Berlin; HeLa human cervical tumor cells, ATCC CCL-2; B16F10 mouse melanoma cells, ATCC CRL-6475) were plated at a density of 5000 cells/well (MCF7, DU145, HeLa-MaTu-ADR), 3000 cells/well (NCI-H460, HeLa-MaTu, HeLa), or 1000 cells/well (B16F10) in a 96-well multititer plate in 200 µl of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.01-30 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The IC50 values were determined by means of a 4 parameter fit using the company's own software. The compounds of the present invention are characterized by an $IC_{50}$ determined in a HeLa-MaTu-ADR cell proliferation assay (as described above) that is lower than 10 µM. The $IC_{50}$ of preferred compounds is even lower than 2.0 µM. The $IC_{50}$ of more preferred compounds is even lower than 500 nM. The $IC_{50}$ of even more preferred compounds is even lower than 250 nM. The $IC_{50}$ of most preferred compounds is even lower than 200 nM.

Mps-1 Kinase Assay with 10 µM ATP

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity. N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence biotin-Ahx-PWDPDDADITEILG (C-terminus in amide form, purchased from Biosynthan GmbH, Berlin) was used.

For the assay 50 nl of a 100-fold concentrated solution of the test compound in DMSO was pipetted into a black low volume 384 well microtiter plate (Greiner Bio-One, Frickenhausen, Germany), 2 µL of a solution of Mps-1 in assay buffer [0.1 mM sodium-ortho-vanadate, 10 mM $MgCl_2$, 2 mM DTT, 25 mM Hepes pH 7.7, 0.05% BSA (w/v), 0.001% Pluronic F-127] were added and the mixture was incubated for 15 min at 22° C. to allow pre-binding of the test compounds to Mps-1 before the start of the kinase reaction. Then the kinase reaction was started by the addition of 3 µL of a solution of 16.7 µM adenosine-tri-phosphate (ATP, 16.7 µM=> final conc. in the 5 µL assay volume is 10 µM) and peptide substrate (1.67 µM=> final conc. in the 5 µL assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 0.5 nM (final conc. in the 5 µL assay volume). The reaction was stopped by the addition of 5 µL of a solution of TR-FRET detection reagents (100 mM Hepes pH 7.4, 0.1% BSA, 40 mM EDTA, 140 nM Streptavidin-XLent [#61GSTXLB, Fa. Cis Biointernational, Marcoule, France], 1.5 nM anti-phospho(Ser/Thr)-Europium-antibody [#AD0180, PerkinElmer LAS, Rodgau-Jügesheim, Germany]. Instead of the 1.5 nM anti-phospho(Ser/Thr)-Europium-antibody a mixture of 2 nM unlabeled anti-phospho ser/thr-pro antibody MPM-2 [Millipore cat. #05-368] and 1 nM LANCE EU-W1024 labeled anti-mouse IgG antibody [Perkin-Elmer, product no. AD0077] can be used).

The resulting mixture was incubated 1 h at 22° C. to allow the binding of the phosphorylated peptide to the anti-phospho (Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheim, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Mps-1 Kinase Assay with 2 mM ATP

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity. N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence biotin-Ahx-PWDPDDADITEILG (C-terminus in amide form, purchased from Biosynthan GmbH, Berlin) was used.

For the assay 50 nl of a 100-fold concentrated solution of the test compound in DMSO was pipetted into a black low volume 384 well microtiter plate (Greiner Bio-One, Frickenhausen, Germany), 2 µL of a solution of Mps-1 in assay buffer [0.1 mM sodium-ortho-vanadate, 10 mM $MgCl_2$, 2 mM DTT, 25 mM Hepes pH 7.7, 0.05% BSA (w/v), 0.001% Pluronic F-127] were added and the mixture was incubated for 15 min at 22° C. to allow pre-binding of the test compounds to Mps-1 before the start of the kinase reaction. Then the kinase reaction was started by the addition of 3 µL of a solution of 3.33 mM adenosine-tri-phosphate (ATP, 3.3 mM=> final conc. in the 5 µL assay volume is 2 mM) and peptide substrate (1.67 µM=> final conc. in the 5 µL assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 0.5 nM (final conc. in the 5 µL assay volume). The reaction was stopped by the addition of 5 µL of a solution of TR-FRET detection reagents (100 mM Hepes pH 7.4, 0.1% BSA, 40 mM EDTA, 140 nM Streptavidin-XLent [#61GSTXLB, Fa. C is Biointernational, Marcoule, France], 1.5 nM anti-phospho(Ser/Thr)-Europium-antibody [#AD0180, PerkinElmer LAS, Rodgau-Jügesheim, Germany]. Instead of the 1.5 nM anti-phospho(Ser/Thr)-Europium-antibody a mixture of 2 nM unlabeled anti-phospho ser/thr-pro antibody MPM-2 [Millipore cat. #05-368] and 1 nM LANCE EU-W1024 labeled anti-mouse IgG antibody [Perkin-Elmer, product no. AD0077] can be used).

The resulting mixture was incubated 1 h at 22° C. to allow the binding of the phosphorylated peptide to the anti-phospho (Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheim, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumor cell line HeLa (ATCC CCL-2) were plated at a density of 2500 cells/well in a 384-well microtiter plate in 20 µl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 µl/well nocodazole at a final concentration of 0.1 µg/ml were added to cells. After 24 h incubation, cells were arrested at G2/M phase of the cell cycle progression. Test compounds solubilised in dimethyl sulfoxide (DMSO) were added at various concentrations (0 µM, as well as in the range of 0.005 µM-10 µM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 µl/well antibody solution (anti-phospho-histone H3 clone 3H10, FITC; Upstate, Cat#16-222; 1:200 dilution) was added to cells, which were incubated for 2 h at room temperature. Afterwards, cells were washed with PBS and 20 µl/well HOECHST 33342 dye solution (5 µg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the $IC_{50}$ value for each tested compound.

It will be apparent to persons skilled in the art that assays for other Mps kinases may be performed in analogy using the appropriate reagents.

Thus the compounds of the present invention effectively inhibit one or more Mps-1 kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

Determination of Metabolic Stability In Vitro (including calculation of hepatic in vivo blood clearance (CL) and of maximal oral bioavailability ($F_{max}$))

The metabolic stability of test compounds in vitro was determined by incubating them at 1 µM with a suspension liver microsomes in 100 mM phosphate buffer, pH7.4 ($NaH_2PO_4 \times H_2O + Na_2HPO_4 \times 2H_2O$) at a protein concentration of 0.5 mg/mL and at 37° C. The reaction was activated by adding a co-factor mix containing 1.2 mg NADP, 3 IU glucose-6-phosphate dehydrogenase, 14.6 mg glucose-6-phosphate and 4.9 mg $MgCl_2$ in phosphate buffer, pH 7.4. Organic solvent in the incubations was limited to <0.2% dimethylsulfoxide (DMSO) and <1% methanol. During incubation, the microsomal suspensions were continuously shaken and aliquots were taken at 2, 8, 16, 30, 45 and 60 min, to which equal volumes of cold methanol were immediately added. Samples were frozen at −20° C. over night, subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, specific liver weight and microsomal protein content the hepatic in vivo blood clearance (CL) and the maximal oral bioavailability ($F_{max}$) were calculated for the different species. The following parameter values were used: Liver blood flow—1.3 L/h/kg (human), 2.1 L/h/kg (dog), 4.2 L/h/kg (rat); specific liver weight—21 g/kg (human), 39 g/kg (dog), 32 g/kg (rat); microsomal protein content—40 mg/g.

With the described assay only phase-I metabolism of microsomes is reflected, e.g. typically oxidoreductive reactions by cytochrome P450 enzymes and flavin mono-oxygenases (FMO) and hydrolytic reactions by esterases (esters and amides).

Hydrolytic Stability Assay

The hydrolytic stability assay investigates the stability of a compound in an aqueous buffer system. Standard solution stability assay is run in 0.05 M Phosphate buffer at pH 7.4 (pH of blood plasma) at 37° C. As compounds in the GI tract are exposed to a wide variety of pHs any relevant pH (as pH 2 to simulate the acidic condition of the GI tract in the following experiment) can be chosen. Compounds are incubated in relevant solution at 37° C. and analyzed by HPLC immediately after incubation and after 1, 2 and 24 hrs. Degradation rate (decay in %) is calculated by relating peak areas after 1, 2 and 24 hrs to the time zero injection.

Compound is available as 10 mM in DMSO (solution 1). 2.5 µL of solution 1 is dissolved in 1 mL acetonitrile leading to solution 2. Poorly soluble compounds may demand another dilution step of solution 2 (1:5 and 1:10 respectively) in Acetonitrile). Solution 2 is incubated at 37° C. in a tempered HPLC autosampler. 1 mL buffer pH 2 is transferred into an HPLC vial. 100 µL of solution 2 is added to the buffer pH 2 solution and mixed thoroughly. Immediately after mixing the combined solution is injected into the HPLC to give the time zero injection. Injections are repeated after 1, 2 and 24 hrs.

The degredation rate (decay in %) is calculated using HPLC software Millennium and Excel respectively.

Surprisingly it was found, that the compounds of the present invention are characterized by an $IC_{50}$ lower than 2 nM (more potent than 2 nM) in an Mps-1 kinase assay with a concentration of 10 µM ATP, and an $IC_{50}$ lower than 30 nM (more potent than 30 nM) in an Mps-1 kinase assay with a concentration of 2 mM ATP, and a high hydrolytic stability, with less than 10% decay after 24 h at pH 2.

Preferred compounds of the present invention show even better performance. Preferred compounds of the present invention are characterized by:

an $IC_{50}$ lower than or equal to 1 nM (more potent than 1 nM) in an Mps-1 kinase assay with a concentration of 10 µM ATP, and an $IC_{50}$ lower than 10 nM (more potent than 10 nM) in an Mps-1 kinase assay with a concentration of 2 mM ATP, and a maximum oral bioavailability ($F_{max}$) in rat that is higher than 50% determined by means of rat liver microsomes as described below, and a maximum oral bioavailability ($F_{max}$) in dog that is higher than 45% determined by means of dog liver microsomes as described below, and a maximum oral bioavailability ($F_{max}$) in human that is higher than 45%, determined by means of human liver microsomes as described below, and an $IC_{50}$ lower than 600 nM in a HeLa cell proliferation assay as described below.

Said preferred compounds of the present invention are characterized by general formula (PC):

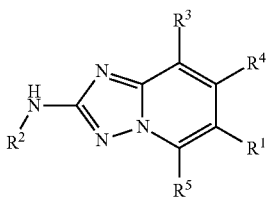

(PC)

in which:

R¹ represents

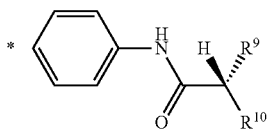

wherein * indicates the point of attachment of said group with the rest of the molecule;

R² represents

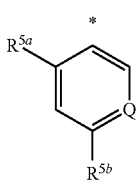

wherein * indicates the point of attachment of said group with the rest of the molecule;

R³ represents a hydrogen atom;
R⁴ represents a hydrogen atom;
R⁵ represents a hydrogen atom or a $C_1$-$C_3$-alkyl-group;
$R^{5a}$ represents a group selected from: $C_1$-$C_4$-alkoxy-, halo-$C_1$-$C_4$-alkoxy-, $C_1$-$C_4$-alkyl;
$R^{5b}$ represents a group selected from:
—C(=O)N(H)R⁸, —C(=O)NR⁸R⁷, —N(R⁷)C(=O)OR⁸, R⁷—S(=O)₂—;
R⁷ represents a $C_1$-$C_3$-alkyl- or a cyclopropyl-group;
R⁸ represents a hydrogen atom or a $C_1$-$C_6$-alkyl- or $C_3$-$C_6$-cycloalkyl-group; wherein said $C_1$-$C_6$-alkyl- or $C_3$-$C_6$-cycloalkyl-group is optionally substituted, one or more times, with a halogen atom;
or
R⁷ and R⁸, together with the molecular fragment they are attached to, represent a 4- to 6-membered heterocyclic ring, which is optionally substituted, one or more times, identically or differently, with a halogen atom, a $C_1$-$C_3$-alkyl-, halo-$C_1$-$C_3$-alkyl- or $C_1$-$C_3$-alkoxy-group;
R⁹ represents a group selected from: $C_1$-$C_3$-alkyl-, hydroxy-$C_1$-$C_3$-alkyl-, —N(H)R⁸; —N(R⁷)R⁸, N(H)(R⁸)—$C_1$-$C_3$-alkyl-, N(R⁷)(R⁸)—$C_1$-$C_3$-alkyl-;
R¹⁰ represents a

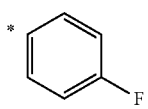

group;
wherein * indicates the point of attachment of said group with the rest of the molecule;

wherein said group is optionally substituted, one or more times, identically or differently, with a halogen atom or a methyl-group;
and
Q represents CH or N;
or a tautomer, an N-oxide, a hydrate, a solvate, or a salt thereof, or a mixture of same.

Most preferred compounds of the present invention are selected from:

(2R)-2-(4-fluorophenyl)-N-[4-(2-{[2-methoxy-4-(methylsulfonyl)phenyl]amino}-[1,2,4]triazolo[1,5-a]pyridin-6-yl)phenyl]propanamide, (2R)—N-[4-(2-{[2-ethoxy-4-(methylsulfonyl)phenyl]amino}[1,2,4]triazolo[1,5-a]pyridin-6-yl)phenyl]-2-(4-fluorophenyl)propanamide, (2R)-2-(4-fluorophenyl)-N-[4-(2-{[4-(methylsulfonyl)-2-(2,2,2-trifluoroethoxy)-phenyl]amino}[1,2,4]triazolo[1,5-a]pyridin-6-yl)phenyl]propanamide, 4-{[6-(4-{[(2R)-2-(4-fluorophenyl)propanoyl]amino}phenyl)[1,2,4]triazolo[1,5-a]pyridin-2-yl]amino}-3-methoxy-N-(2,2,2-trifluoroethyl)benzamide, 4-{[6-(4-{[(2R)-2-(4-fluorophenyl)propanoyl]amino}phenyl)[1,2,4]triazolo[1,5-a]-pyridin-2-yl]amino}-3-methoxybenzamide, 4-{[6-(4-{[(2R)-2-(4-fluorophenyl)propanoyl]amino}phenyl)[1,2,4]triazolo[1,5-a]-pyridin-2-yl]amino}-3-(2,2,2-trifluoroethoxy)benzamide, (2R)—N-{4-[2-({4-[(3-fluoroazetidin-1-yl)carbonyl]-2-methoxyphenyl}amino)-[1,2,4]triazolo[1,5-a]pyridin-6-yl]phenyl}-2-(4-fluorophenyl)propanamide, (2R)—N-[4-(2-{[4-(azetidin-1-ylcarbonyl)-2-methoxyphenyl]amino}[1,2,4]triazolo[1,5-a]pyridin-6-yl)phenyl]-2-(4-fluorophenyl)propanamide, (2R)-2-(4-fluorophenyl)-N-[4-(2-{[2-methoxy-4-(2-oxo-1,3-oxazolidin-3-yl)phenyl]-amino}[1,2,4]triazolo[1,5-a]pyridin-6-yl)phenyl]propanamide, (−)-2-(4-fluorophenyl)-3-hydroxy-N-[4-(2-{[4-(methylsulfonyl)-2-(2,2,2-tri-fluoroethoxy)phenyl]amino}[1,2,4]triazolo[1,5-a]pyridin-6-yl)phenyl]propanamide, (2R)-2-amino-2-(4-fluorophenyl)-N-[4-(2-{[2-methoxy-4-(methylsulfonyl)-phenyl]amino}[1,2,4]triazolo[1,5-a]pyridin-6-yl)phenyl]ethanamide, 4-{[6-(4-{[(2R)-2-(4-fluorophenyl)propanoyl]amino}phenyl)[1,2,4]triazolo[1,5-a]pyridin-2-yl]amino}-3-methoxy-N,N-dimethylbenzamide, (2R)-2-(4-fluorophenyl)-N-[4-(2-{[2-methoxy-4-(pyrrolidin-1-ylcarbonyl)phenyl]amino}[1,2,4]triazolo[1,5-a]pyridin-6-yl)phenyl]propanamide, (2R)—N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)propanamide, (2R)-2-(4-fluorophenyl)-N-{4-[2-({4-[(3-hydroxyazetidin-1-yl)carbonyl]-2-(2,2,2-trifluoroethoxy)phenyl}amino)[1,2,4]triazolo[1,5-a]pyridin-6-yl]phenyl}propanamide, (2R)-2-(4-fluorophenyl)-N-[4-(2-{[4-(pyrrolidin-1-ylcarbonyl)-2-(2,2,2-trifluoroethoxy)phenyl]amino}[1,2,4]triazolo[1,5-a]pyridin-6-yl)phenyl]propanamide, (2S)-2-(4-fluorophenyl)-3-hydroxy-N-[4-(2-{[2-methoxy-4-(methylsulfonyl)phenyl]amino}[1,2,4]triazolo[1,5-a]pyridin-6-yl)phenyl]propanamide, (2S)—N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)-3-hydroxypropanamide, (2R)-2-amino-2-(4-fluorophenyl)-N-[4-(2-{[4-(methylsulfonyl)-2-(2,2,2-trifluoroethoxy)phenyl]amino}[1,2,4]triazolo[1,5-a]pyridin-6-yl)phenyl]ethanamide, (2R)-2-amino-2-(4-fluorophenyl)-N-[4-(2-{[2-methoxy-4-(2-oxo-1,3-oxazolidin-3-yl)phenyl]amino}[1,2,4]triazolo[1,5-a]pyridin-6-yl)phenyl]ethanamide, (2R)-2-amino-N-{4-[2-({4-[(3-fluoroazetidin-1-yl)carbonyl]-2-methoxyphenyl}amino)[1,2,4]triazolo[1,5-a]pyridin-6-yl]phenyl}-2-(4-fluorophenyl)ethanamide, (2R)-2-amino-N-[4-(2-{[4-(azetidin-1-ylcarbonyl)-2-methoxyphenyl]amino}[1,2,4]triazolo[1,5-a]pyridin-6-yl)phenyl]-2-(4-fluorophenyl)ethanamide, (2R)-2-amino-2-(4-fluorophenyl)-N-[4-(2-{[2-methoxy-4-(pyrrolidin-1-ylcarbonyl)phenyl]amino}[1,2,4]triazolo[1,5-a]pyridin-6-yl)phenyl]ethanamide, (2R)-2-amino-N-{4-[2-({4-[(3-fluoroazetidin-1-yl)carbonyl]-2-(2,2,2-trifluoroethoxy)phenyl}amino)[1,2,4]triazolo[1,5-a]pyridin-6-yl]phenyl}-2-(4-fluorophenyl)ethanamide, and or a tautomer, an N-oxide, a hydrate, a solvate, or a salt thereof, or a mixture of same.

As mentioned supra, the compounds of the present invention have surprisingly been found to effectively inhibit Mps-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The invention claimed is:

1. Method for preparing a compound of formula (I):

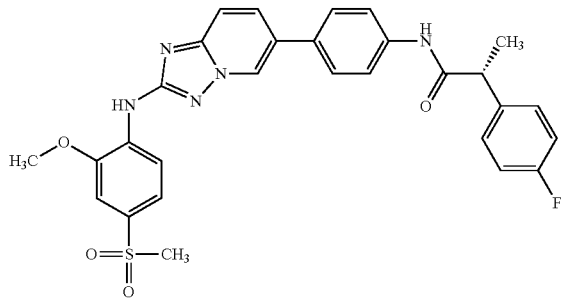 [SMILES: COc1cc(S(C)(=O)=O)ccc1Nc1nc2ccc(-c3ccc(NC(=O)[C@H](C)c4ccc(F)cc4)cc3)cn2n1]

comprising reacting a compound of formula (In1):

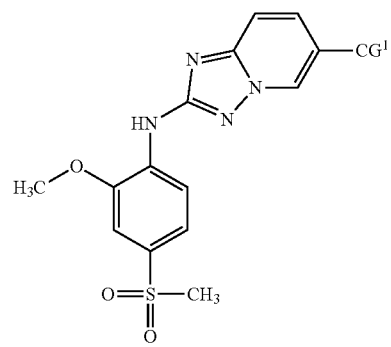

with a compound of formula (In5)

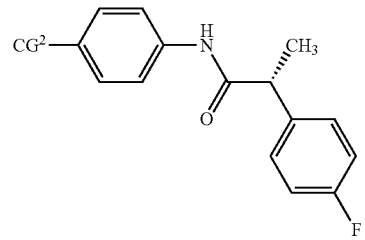

wherein one of the groups $CG^1$ and $CG^2$ represents chloro, bromo, iodo or trifluoromethylsulfonyloxy, and the other one of the groups $CG^1$ and $CG^2$ represents a boronic acid or an ester thereof, thus providing the compound of formula (I).

2. The method according to claim 1, wherein the compound of formula (In1) is 6-chloro-N-[2-methoxy-4-(methylsulfonyl)phenyl][1,2,4]triazolo[1,5-a]pyridin-2-amine and the compound of formula (In5) is (2R)-2-(4-fluorophenyl)-N-[4-(4,4,5,5-tetramethyl-1,3,2-dioxaborolan-2-yl)phenyl]propanamide.

3. The method according to claim 1, wherein the compound of formula (In1) is 6-chloro-N-[2-methoxy-4-(methylsulfonyl)phenyl][1,2,4]triazolo[1,5-a]pyridin-2-amine and the compound of formula (In5) is (4-{[(2R)-2-(4-fluorophenyl)propanoyl]amino}phenyl)boronic acid.

* * * * *